(12) United States Patent
Engel et al.

(10) Patent No.: US 10,913,897 B2
(45) Date of Patent: Feb. 9, 2021

(54) COMPOUNDS AND LIQUID-CRYSTALLINE MEDIUM

(71) Applicant: MERCK PATENT GMBH, Darmstadt (DE)

(72) Inventors: Martin Engel, Darmstadt (DE); Sabrina Maag, Pfungstadt (DE); Ingo Almeroth, Bensheim (DE); Rocco Fortte, Frankfurt Am Main (DE); Achim Goetz, Alsbach-Haehnlein (DE); Thorsten Kodek, Moerfelden-Walldorf (DE); Oliver Heppert, Weiterstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 15/883,976

(22) Filed: Jan. 30, 2018

(65) Prior Publication Data

US 2018/0216005 A1 Aug. 2, 2018

(30) Foreign Application Priority Data

Jan. 30, 2017 (DE) .......................... 10 2017 000 812

(51) Int. Cl.
*G02F 1/137* (2006.01)
*C09K 19/44* (2006.01)
(Continued)

(52) U.S. Cl.
CPC ............ *C09K 19/44* (2013.01); *C07D 401/14* (2013.01); *C09K 19/12* (2013.01);
(Continued)

(58) Field of Classification Search
CPC .... C09K 19/44; C09K 19/12; C09K 19/3003; C09K 19/3098; C09K 19/3405;
(Continued)

(56) References Cited

U.S. PATENT DOCUMENTS

| 4,813,770 A | 3/1989 | Clerc |
| 8,168,081 B2 | 5/2012 | Klasen-Memmer |

(Continued)

FOREIGN PATENT DOCUMENTS

| DE | 102016009485.0 | 8/2016 |
| EP | 0240379 A1 | 2/1987 |

(Continued)

*Primary Examiner* — Geraldina Visconti
(74) *Attorney, Agent, or Firm* — Millen White Zelano & Branigan

(57) ABSTRACT

Compounds of the formula I, and liquid-crystalline media, preferably having a nematic phase and negative dielectric anisotropy, comprising
a) one or more compounds of the formula I $$[R^{12}]_m - ZG - [Z^{14} - S^{12} - Z^{13} - X^{11} - [Z^{12} - S^{11} - Z^{11}]_o^{[R_{11}]} - \begin{pmatrix} Y^{11} \\ Y^{12} \\ N-H \\ Y^{14} Y^{13} \end{pmatrix}_p]_n \quad I$$

and one or more compounds selected from
b) one or more compounds of formula II $$R^{21} - \text{[cyclohexyl-cyclohexyl]} - R^{22} \quad II$$

and/or
c) one or more compounds selected from compounds of formulae III-1 to III-4 and formula B III-1, III-2, III-3, III-4, B structures with $R^{31}$, $R^{32}$, $R^{B1}$, $R^{B2}$, $L^{B1}$, $L^{B2}$ substituents.

Methods for making and using these liquid-crystalline media in electro-optical displays, particularly in active-matrix displays based on the VA, ECB, PALC, FFS or IPS effect and
(Continued)

the displays which contain these media. Methods for stabilizing liquid-crystalline media with compounds of formula I, where the liquid-crystalline media comprise one or more compounds of the formula II and one or more compounds selected from compounds of the formulae III-1 to III-4 and formula B.

18 Claims, No Drawings

(51) Int. Cl.
| | |
|---|---|
| *C09K 19/30* | (2006.01) |
| *C07D 401/14* | (2006.01) |
| *C09K 19/12* | (2006.01) |
| *C09K 19/34* | (2006.01) |
| *G02F 1/1333* | (2006.01) |
| *C09K 19/02* | (2006.01) |

(52) U.S. Cl.
CPC ...... *C09K 19/3003* (2013.01); *C09K 19/3098* (2013.01); *C09K 19/3405* (2013.01); *C09K 19/3483* (2013.01); *G02F 1/1333* (2013.01); C09K 19/0216 (2013.01); C09K 2019/122 (2013.01); C09K 2019/123 (2013.01); C09K 2019/301 (2013.01); C09K 2019/3004 (2013.01); C09K 2019/3009 (2013.01); C09K 2019/3016 (2013.01); C09K 2019/3027 (2013.01); C09K 2019/3408 (2013.01)

(58) Field of Classification Search
CPC ............ C09K 19/3483; C09K 19/0216; C09K 2019/122; C09K 2019/123; C09K 2019/3004; C09K 2019/3009; C09K 2019/301; C09K 2019/3016; C09K 2019/3027; C09K 2019/3408; G02F 1/137; G02F 1/1333; C07D 401/14

USPC ................................................... 252/299.61
See application file for complete search history.

(56) References Cited

U.S. PATENT DOCUMENTS

| | | | |
|---|---|---|---|
| 8,277,684 | B2 | 10/2012 | Klasen-Memmer |
| 9,434,882 | B2 | 9/2016 | Goebel |
| 9,441,162 | B2* | 9/2016 | Furusato ............ C09K 19/3483 |
| 9,920,248 | B2 | 3/2018 | Goebel |
| 2013/0258268 | A1 | 10/2013 | Goebel |
| 2016/0032188 | A1 | 2/2016 | Furusato |
| 2016/0060528 | A1 | 3/2016 | Goetz |
| 2016/0090533 | A1* | 3/2016 | Hirschmann ........ C07D 307/91 |
| | | | 252/299.61 |
| 2016/0122301 | A1 | 5/2016 | Furusato |
| 2017/0362506 | A1 | 12/2017 | Hirschmann |
| 2018/0037820 | A1 | 2/2018 | Goetz |

FOREIGN PATENT DOCUMENTS

| | | |
|---|---|---|
| EP | 0240379 A1 | 10/1987 |
| EP | 2182046 B1 | 3/2012 |
| EP | 2993216 A1 | 3/2016 |
| EP | 3015534 A1 | 5/2016 |
| EP | 2514800 B2 | 3/2018 |
| JP | S55-023169 A | 2/1980 |
| JP | H05-117324 A | 5/1993 |
| JP | 09-291282 A | 11/1997 |
| WO | 02/18515 A1 | 3/2002 |
| WO | 2008/009417 A1 | 1/2008 |
| WO | 2009/021671 A1 | 2/2009 |
| WO | 2009/115186 A1 | 9/2009 |
| WO | 2009/129911 A1 | 10/2009 |
| WO | 2012076104 A1 | 6/2012 |
| WO | 2012076105 A1 | 6/2012 |
| WO | 2016146245 A1 | 9/2016 |

* cited by examiner

COMPOUNDS AND LIQUID-CRYSTALLINE MEDIUM

The present invention relates to novel compounds, in particular for use in liquid-crystal media, but also to the use of these liquid-crystal media in liquid-crystal displays, and to these liquid-crystal displays, particularly liquid-crystal displays which use the ECB (electrically controlled birefringence) effect with dielectrically negative liquid crystals in a homeotropic initial alignment. The liquid-crystal media according to the invention are distinguished by a particularly short response time in the displays according to the invention at the same time as a high voltage holding ratio (VHR or also just HR for short).

The principle of electrically controlled birefringence, the ECB effect or DAP (deformation of aligned phases) effect, was described for the first time in 1971 (M. F. Schieckel and K. Fahrenschon, "Deformation of nematic liquid crystals with vertical orientation in electrical fields", Appl. Phys. Lett. 19 (1971), 3912). Papers by J. F. Kahn (Appl. Phys. Lett. 20 (1972), 1193) and G. Labrunie and J. Robert (J. Appl. Phys. 44 (1973), 4869) followed.

The papers by J. Robert and F. Clerc (SID 80 Digest Techn. Papers (1980), 30), J. Duchene (Displays 7 (1986), 3) and H. Schad (SID 82 Digest Techn. Papers (1982), 244) have shown that liquid-crystalline phases must have high values for the ratio between the elastic constants $K_3/K_1$, high values for the optical anisotropy $\Delta n$ and values for the dielectric anisotropy $\Delta\varepsilon$ of $\leq -0.5$ in order to be suitable for use for high-information display elements based on the ECB effect. Electro-optical display elements based on the ECB effect have a homeotropic edge alignment (VA technology=vertically aligned or also VAN=vertical aligned nematic). Dielectrically negative liquid-crystal media can also be used in displays which use the so-called IPS (in-plane switching) effect.

Industrial application of this effect in electro-optical display elements requires LC phases which have to meet a multiplicity of requirements. Particularly important here are chemical resistance to moisture, air and physical influences, such as heat, radiation in the infrared, visible and ultraviolet regions, and direct and alternating electric fields.

Furthermore, LC phases which can be used industrially are required to have a liquid-crystalline mesophase in a suitable temperature range and low viscosity.

None of the series of compounds having a liquid-crystalline mesophase that have been disclosed hitherto includes a single compound which meets all these requirements. Mixtures of two to 25, preferably three to 18, compounds are therefore generally prepared in order to obtain substances which can be used as LC phases.

Matrix liquid-crystal displays (MLC displays) are known. Non-linear elements which can be used for individual switching of the individual pixels are, for example, active elements (i.e. transistors). The term "active matrix" is then used, where in general use is made of thin-film transistors (TFTs), which are generally arranged on a glass plate as substrate.

A distinction is made between two technologies: TFTs comprising compound semiconductors, such as, for example, CdSe, or TFTs based on polycrystalline and, inter alia, amorphous silicon. The latter technology currently has the greatest commercial importance worldwide.

The TFT matrix is applied to the inside of one glass plate of the display, while the other glass plate carries the transparent counterelectrode on its inside. Compared with the size of the pixel electrode, the TFT is very small and has virtually no adverse effect on the image. This technology can also be extended to fully colour-capable displays, in which a mosaic of red, green and blue filters is arranged in such a way that a filter element is located opposite each switchable pixel.

The TFT displays most used hitherto usually operate with crossed polarisers in transmission and are backlit. For TV applications, IPS cells or ECB (or VAN) cells are used, whereas monitors usually use IPS cells or TN (twisted nematic) cells, and notebooks, laptops and mobile applications usually use TN cells.

The term MLC displays here encompasses any matrix display having integrated non-linear elements, i.e., besides the active matrix, also displays with passive elements, such as varistors or diodes (MIM=metal-insulator-metal).

MLC displays of this type are particularly suitable for TV applications, monitors and notebooks or for displays with a high information density, for example in automobile manufacture or aircraft construction. Besides problems regarding the angle dependence of the contrast and the response times, difficulties also arise in MLC displays due to insufficiently high specific resistance of the liquid-crystal mixtures [TOGASHI, S., SEKIGUCHI, K., TANABE, H., YAMAMOTO, E., SORIMACHI, K., TAJIMA, E., WATA-NABE, H., SHIMIZU, H., Proc. Eurodisplay 84, September 1984: A 210-288 Matrix LCD Controlled by Double Stage Diode Rings, pp. 141 ff., Paris; STROMER, M., Proc. Eurodisplay 84, September 1984: Design of Thin Film Transistors for Matrix Addressing of Television Liquid Crystal Displays, pp. 145 ff., Paris]. With decreasing resistance, the contrast of an MLC display deteriorates. Since the specific resistance of the liquid-crystal mixture generally drops over the life of an MLC display owing to interaction with the inside surfaces of the display, a high (initial) resistance is very important for displays that have to have acceptable resistance values over a long operating period.

Displays which use the ECB effect have become established as so-called VAN (vertically aligned nematic) displays, besides IPS displays (for example: Yeo, S. D., Paper 15.3: "An LC Display for the TV Application", SID 2004 International Symposium, Digest of Technical Papers, XXXV, Book II, pp. 758 and 759) and the long-known TN displays, as one of the three more recent types of liquid-crystal display that are currently the most important, in particular for television applications.

The most important designs which may be mentioned are: MVA (multi-domain vertical alignment, for example: Yoshide, H. et al., Paper 3.1: "MVA LCD for Notebook or Mobile PCs . . . ", SID 2004 International Symposium, Digest of Technical Papers, XXXV, Book I, pp. 6 to 9, and Liu, C. T. et al., Paper 15.1: "A 46-inch TFT-LCD HDTV Technology . . . ", SID 2004 International Symposium, Digest of Technical Papers, XXXV, Book II, pp. 750 to 753), PVA (patterned vertical alignment, for example: Kim, Sang Soo, Paper 15.4: "Super PVA Sets New State-of-the-Art for LCD-TV", SID 2004 International Symposium, Digest of Technical Papers, XXXV, Book II, pp. 760 to 763) and ASV (advanced super view, for example: Shigeta, Mitzuhiro and Fukuoka, Hirofumi, Paper 15.2: "Development of High Quality LCDTV", SID 2004 International Symposium, Digest of Technical Papers, XXXV, Book II, pp. 754 to 757).

In general form, the technologies are compared, for example, in Souk, Jun, SID Seminar 2004, Seminar M-6: "Recent Advances in LCD Technology", Seminar Lecture Notes, M-6/1 to M-6/26, and Miller, Ian, SID Seminar 2004, Seminar M-7: "LCD-Television", Seminar Lecture Notes, M-7/1 to M-7/32. Although the response times of modern ECB displays have already been significantly improved by addressing methods with overdrive, for example: Kim, Hyeon Kyeong et al., Paper 9.1: "A 57-in. Wide UXGA TFT-LCD for HDTV Application", SID 2004 International Symposium, Digest of Technical Papers, XXXV, Book I, pp. 106 to 109, the achievement of video-compatible response times, in particular in the switching of grey shades, is still a problem which has not yet been solved to a satisfactory extent.

ECB displays, like ASV displays, use liquid-crystalline media having negative dielectric anisotropy ($\Delta\varepsilon$), whereas TN and to date all conventional IPS displays use liquid-crystalline media having positive dielectric anisotropy.

In liquid-crystal displays of this type, the liquid crystals are used as dielectrics, whose optical properties change reversibly on application of an electrical voltage.

Since in displays in general, i.e. also in displays in accordance with these mentioned effects, the operating voltage should be as low as possible, use is made of liquid-crystal media which are generally predominantly composed of liquid-crystal compounds, all of which have the same sign of the dielectric anisotropy and have the highest possible value of the dielectric anisotropy. In general, at most relatively small proportions of neutral compounds and if possible no compounds having a sign of the dielectric anisotropy which is opposite to that of the medium are employed. In the case of liquid-crystal media having negative dielectric anisotropy for ECB displays, predominantly compounds having negative dielectric anisotropy are thus employed. The liquid-crystal media employed generally consist predominantly and usually even essentially of liquid-crystal compounds having negative dielectric anisotropy.

In the media used in accordance with the present application, at most significant amounts of dielectrically neutral liquid-crystal compounds and generally only very small amounts of dielectrically positive compounds or even none at all are typically employed, since in general the liquid-crystal displays are intended to have the lowest possible addressing voltages.

For many practical applications in liquid-crystal displays, the known liquid-crystal media are not sufficiently stable. In particular, their stability to irradiation with UV, but also even with conventional backlighting, results in an impairment, in particular, of the electrical properties. Thus, for example, the conductivity increases significantly.

The use of so-called "hindered amine light stabilisers", HALS for short, has already been proposed for the stabilisation of liquid-crystal mixtures.

Nematic liquid-crystal mixtures having negative dielectric anisotropy which comprise a small amount of TINU-VIN® 770, a compound of the formula

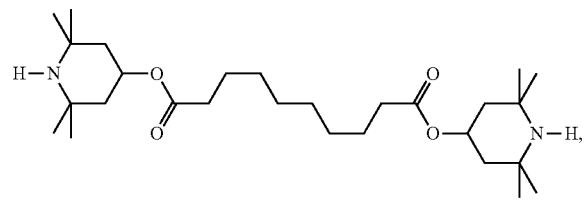

as stabilisers, are proposed, for example, in WO 2009/129911 A1 and in WO 2012/076105 A1. However, the corresponding liquid-crystal mixtures do not have adequate properties for some practical applications. Inter alia, they are not sufficiently stable to irradiation using typical CCFL (cold cathode fluorescent lamp) and in particular the typical, modern LED (light-emitting diode) backlighting.

Similar liquid-crystal mixtures are also known, for example, from EP 2 182 046 A1, WO 2008/009417 A1, WO 2009/021671 A1 and WO 2009/115186 A1. However, the use of stabilisers is not indicated therein.

According to the disclosure therein, these liquid-crystal mixtures may optionally also comprise stabilisers of various types, such as, for example, phenols and sterically hindered amines (hindered amine light stabilisers, HALS for short). However, these liquid-crystal mixtures are characterised by relatively high threshold voltages and by at best moderate stabilities. In particular, their voltage holding ratio drops after exposure. In addition, a yellowish discoloration often arises.

The use of various stabilisers in liquid-crystalline media is described, for example, in JP (S)55-023169 (A), JP (H)05-117324 (A), WO 02/18515 A1 and JP (H) 09-291282 (A).

WO 2009/129911 A1 proposes the compounds

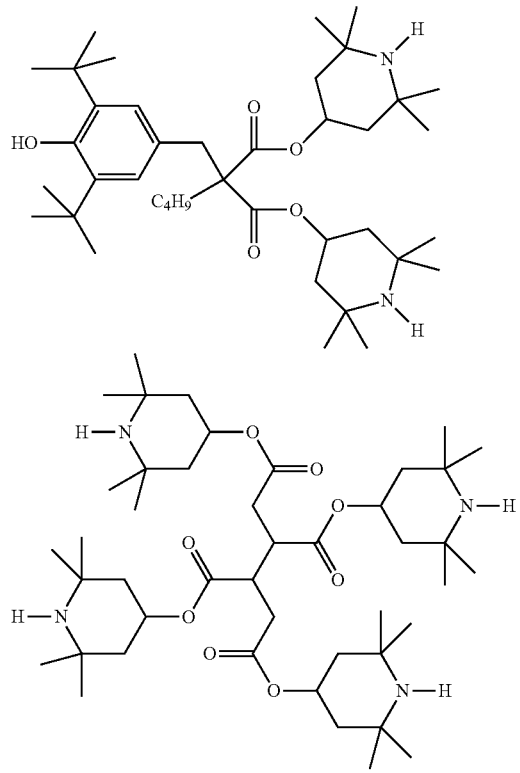

EP 2 993 216 A1 proposes, inter alia, the compound of the formula

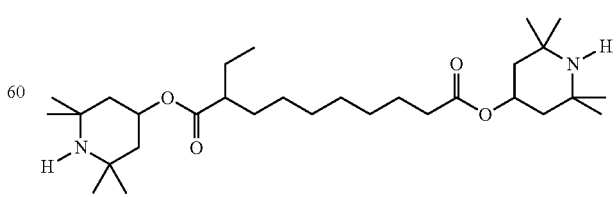

for the stabilisation of dielectrically positive liquid-crystal media.

WO 2009/129911 A1 proposes the compounds

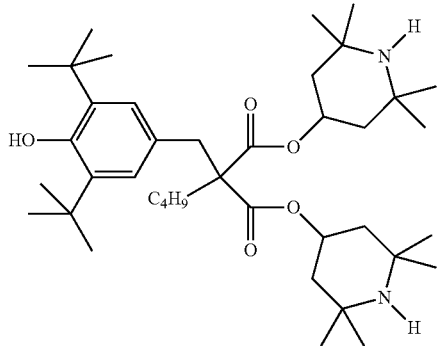

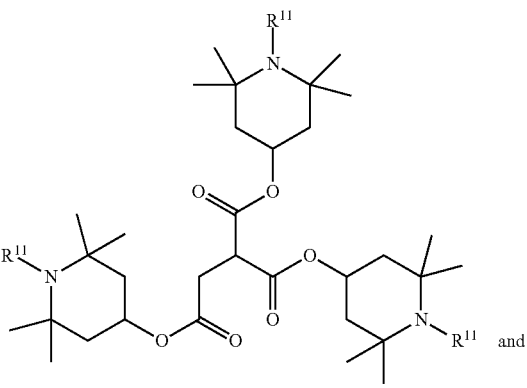

and

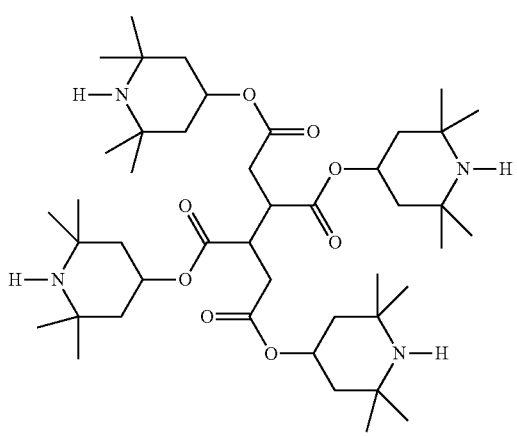

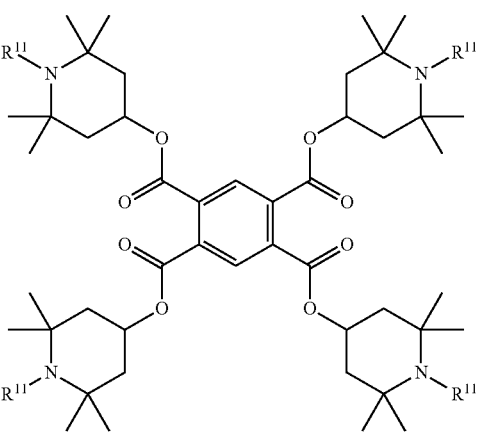

in which $R^{11}$, besides many other meanings, may also be H, for stabilisation purposes in liquid-crystal media. However, the chemical stability of these compounds with respect to hydrolysis and their solubility in liquid-crystal media are in most cases inadequate for practical use.

WO 2016/146245 A1 proposes the compound of the formula

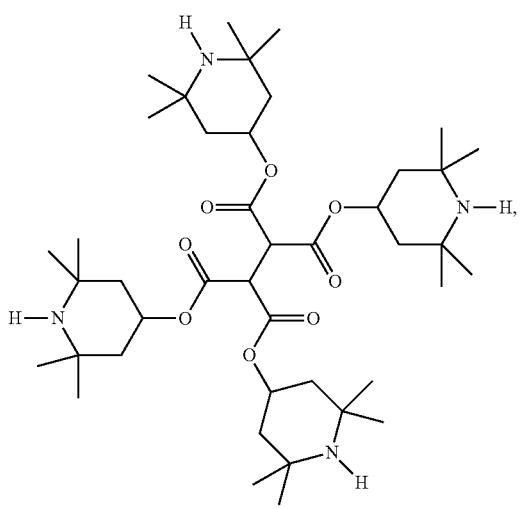

besides several others as second stabilisers besides nitrogen heterocycles for the stabilisation of dielectrically negative liquid-crystal media.

EP 2 514 800 A2 proposes the use of compounds of the formulae

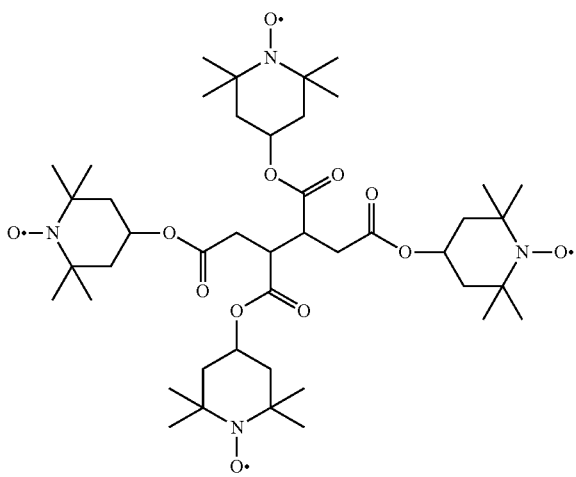

for stabilisation purposes in liquid-crystal media. This compound, as well as the compound

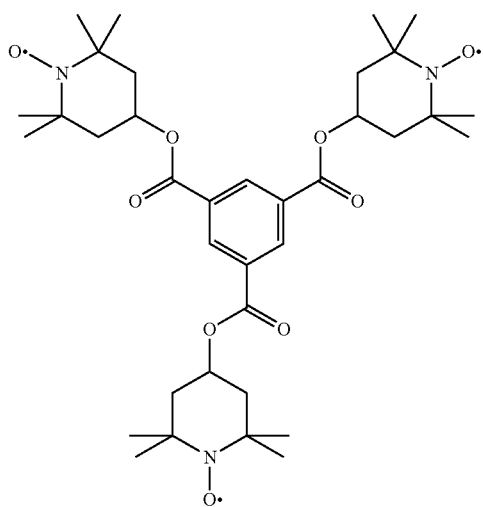

are also proposed in DE 2016 005 083 A1 for stabilisation purposes in liquid-crystal media. However, the chemical stability, particularly with respect to hydrolysis, and especially the solubility in liquid-crystal media in the case of these compounds is in most cases inadequate for practical use. In addition, they are significantly less effective than compounds of the formula I in accordance with present application in liquid-crystal cells with certain polyimides, such as, for example, AL-16301.

The ether-linked compounds of the formulae

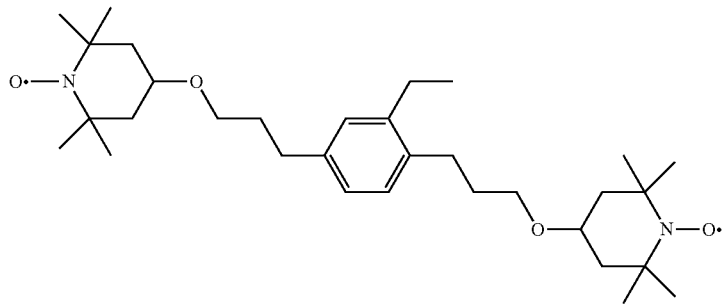

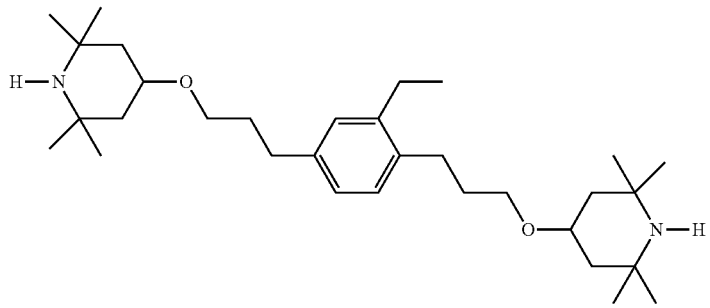

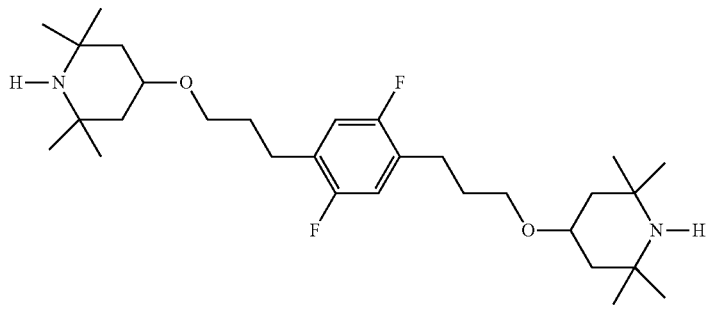

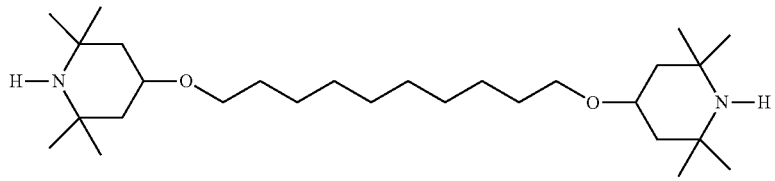

-continued

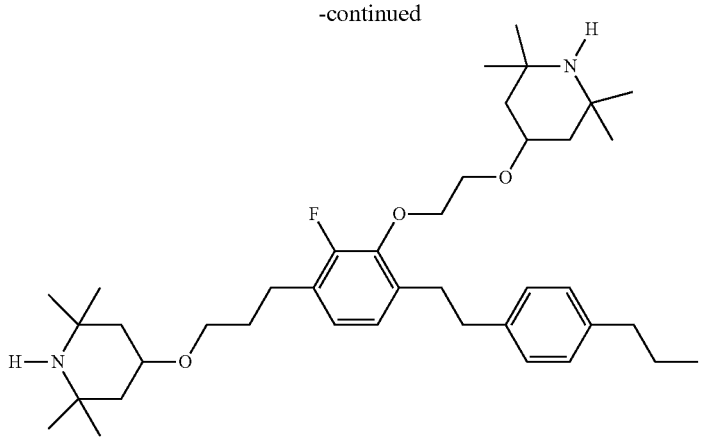

are proposed in the as yet unpublished application DE 10 2016 009485.0 for use as stabilisers for liquid-crystal mixtures.

The liquid-crystal media of the prior art having correspondingly low addressing voltages have relatively low electrical resistance values or a low VHR and often result in undesired flicker and/or inadequate transmission in the displays. In addition, they are not sufficiently stable to heating and/or UV exposure, at least if they have correspondingly high polarity, as is necessary for low addressing voltages.

On the other hand, the addressing voltage of the displays of the prior art which have a high VHR is often too high, in particular for displays which are not connected directly or not continuously to the power supply network, such as, for example, displays for mobile applications.

In addition, the phase range of the liquid-crystal mixture must be sufficiently broad for the intended application of the display. Thus, the low-temperature storage stability in the cell and preferably in bulk at −30° C. should be 240 h or more.

The response times of the liquid-crystal media in the displays must be improved, i.e. reduced. This is particularly important for displays for television or multimedia applications. In order to improve the response times, it has repeatedly been proposed in the past to optimise the rotational viscosity of the liquid-crystal media ($\gamma_1$), i.e. to achieve media having the lowest possible rotational viscosity. However, the results achieved here are inadequate for many applications and therefore make it appear desirable to find further optimisation approaches.

Adequate stability of the media to extreme loads, in particular to UV exposure and heating, is very particularly important. This is particularly difficult with simultaneous optimisation of the rotational viscosity. In particular in the case of applications in displays in mobile equipment, such as, for example, mobile telephones, this may be crucial, since, in particular in the case of these devices, relatively low addressing frequencies are preferably used.

The disadvantage of the MLC displays disclosed hitherto is due to their comparatively low contrast, the relatively high viewing-angle dependence and the difficulty in producing grey shades in these displays, as well as their inadequate VHR and their inadequate lifetime.

There thus continues to be a great demand for MLC displays having very high specific resistance at the same time as a large working-temperature range, short response times and a low threshold voltage, with the aid of which various grey shades can be produced and which have, in particular, a good and stable VHR.

The invention has an object, for example, of providing MLC displays, not only for monitor and TV applications, but also for mobile telephones and navigation systems, which are based on the ECB effect, the IPS effect or on the FFS (fringe field switching) effect, as described in Lee, S. H., Lee, S. L. and Kim, H. Y. "Electro-optical characteristics and switching principle of nematic liquid crystal cell controlled by fringe-field switching", Appl. Phys. Letts., Vol. 73, No. 20, pp. 2881-2883 (1998), do not have the disadvantages indicated above, or only do so to a lesser extent, and at the same time have very high specific resistance values. In particular, it must be ensured for mobile telephones and navigation systems that they also work at extremely high and extremely low temperatures.

Surprisingly, it has been found that it is possible to achieve liquid-crystal displays which have, in particular in FFS displays, a low threshold voltage with short response times and at the same time a sufficiently broad nematic phase, favourable, relatively low birefringence (Δn), good stability to decomposition by heating and by exposure to UV, good solubility in the LC media and a stable, high VHR if use is made in these display elements of nematic liquid-crystal mixtures which comprise at least one compound of the formula I and in each case at least one compound of the formula II, preferably of the sub-formula II-1, and/or at least one compound selected from the group of the compounds of the formulae III-1 to III-4, preferably of the formula III-2, and/or of formula B.

Media of this type can be used, in particular, for electro-optical displays having active-matrix addressing based on the ECB effect and for IPS displays and for FFS displays.

The invention thus relates to a liquid-crystalline medium based on a mixture of polar compounds which comprises at least one compound of the formula I and at least one other compound which contains one or more compounds of the formula II and/or, preferably in addition, one or more compounds selected from the group of the compounds of the formulae III-1 to III-4, and/or of the formula B.

The mixtures according to the invention exhibit very broad nematic phase ranges with clearing points ≥70° C., very favourable values for the capacitive threshold, relatively high values for the holding ratio and at the same time good low-temperature stabilities at −20° C. and −30° C., as well as very low rotational viscosities. The mixtures according to the invention are furthermore distinguished by a good ratio of clearing point and rotational viscosity and by a high negative dielectric anisotropy.

Surprisingly, it has now been found that it is possible to achieve liquid-crystalline media having a suitably high Δε, a suitable phase range and Δn which do not have the disadvantages of the prior-art materials, or at least only do so to a considerably reduced extent.

Surprisingly, it has been found here that the compounds of the formula I, even when used alone without additional heat stabilisers, result in considerable, in many cases adequate, stabilisation of liquid-crystal mixtures both to UV exposure and also to heating. This is the case, in particular, in most cases in which the parameter p in the compounds of the formula I used denotes 2 and n*p denotes 4, 6 or 8. The compounds of the formula I in which p denotes 2 and n denotes 2, 3 or 4 are therefore particularly preferred, and the use of precisely these compounds in the liquid-crystal mixtures according to the invention is particularly preferred. This also applies to the compounds of the formula I in which the group $—Z^{11}—S^{11}—Z^{12}—$ denotes ω-bisoxyalkylene, i.e. $—O—S^{11}—O—$.

However, adequate stabilisation of liquid-crystal mixtures both against UV exposure and against heating can also be achieved, in particular, if one or more further compounds, preferably phenolic stabilisers, are present in the liquid-crystal mixture in addition to the compound of the formula I, or the compounds of the formula I. These further compounds are suitable as heat stabilisers.

The invention thus relates to compounds of the formula I, and to a liquid-crystalline medium having a nematic phase and negative dielectric anisotropy which comprises one or more compounds of the formula I and one or more other compounds of the formula II and/or formulae III-1 to III-4 or formula B. Thus, the medium comprises:

a) one or more compounds of the formula I, preferably in a concentration in the range from 1 ppm to 2500 ppm, preferably to 2000 ppm, preferably to 1500 ppm, particularly preferably to 1000 ppm,

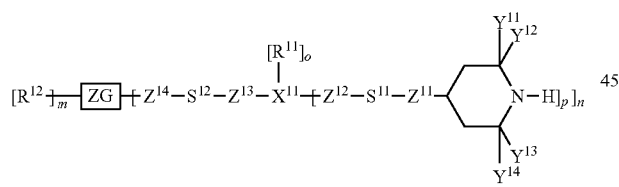

I in which $R^{11}$ on each occurrence, independently of one another, denotes H, F, a straight-chain or branched alkyl chain having 1-20 C atoms, in which one $—CH_2—$ group or, if present, a plurality of $—CH_2—$ groups may be replaced by $—O—$ or $—C(=O)—$, but two adjacent $—CH_2—$ groups cannot be replaced by $—O—$, and one or, if present, a plurality of $—CH_2—$ groups may be replaced by $—CH=CH—$ or $—C≡C—$, and in which one H atom or a plurality of H atoms may be replaced by F, $OR^{13}$, $N(R^{13})(R^{14})$ or $R^{15}$, $R^{11}$ preferably denotes H or alkyl, particularly preferably alkyl, especially preferably n-alkyl and very particularly preferably n-butyl, $R^{12}$ on each occurrence, independently of one another, denotes H, a straight-chain or branched alkyl chain having 1-20 C atoms, in which one $—CH_2—$ group or a plurality of $—CH_2—$ groups may be replaced by $—O—$ or $—C(=O)—$, but two adjacent $—CH_2—$ groups cannot be replaced by $—O—$, a hydrocarbon radical which contains a cycloalkyl or alkylcycloalkyl unit and in which one $—CH_2—$ group or a plurality of $—CH_2—$ groups may be replaced by $—O—$ or $—C(=O)—$, but two adjacent $—CH_2—$ groups cannot be replaced by $—O—$, and in which one H atom or a plurality of H atoms may be replaced by F, $OR^{13}$, $N(R^{13})(R^{14})$ or $R^{15}$, or an aromatic or heteroaromatic hydrocarbon radical, in which one H atom or a plurality of H atoms may be replaced by F, $OR^{13}$, $N(R^{13})(R^{14})$ or $R^{15}$, $R^{12}$ preferably denotes H, unbranched alkyl or branched alkyl, particularly preferably H or unbranched alkyl, $R^{13}$ on each occurrence, independently of one another, denotes H, a straight-chain or branched alkyl or acyl group having 1 to 10 C atoms, preferably n-alkyl, or an aromatic hydrocarbon or carboxylic acid radical having 6-12 C atoms, $R^{14}$ on each occurrence, independently of one another, denotes H, a straight-chain or branched alkyl or acyl group having 1 to 10 C atoms, preferably n-alkyl, or an aromatic hydrocarbon or carboxylic acid radical having 6-12 C atoms, preferably where $R^{14}$ contains an acyl group, $R^{15}$ on each occurrence, independently of one another, denotes a straight-chain or branched alkyl group having 1 to 10 C atoms, in which one $—CH_2—$ group or a plurality of $—CH_2—$ groups may be replaced by $—O—$ or $—C(=O)—$, but two adjacent $—CH_2—$ groups cannot be replaced by $—O—$, $S^{11}$ and $S^{12}$ on each occurrence, independently of one another, denote an alkylene group having 1 to 20 C atoms, which is branched or, preferably, straight-chain, preferably $—(CH_2—)_n$ having 1-20 C atoms, preferably 1-10 C atoms, particularly preferably having 1 to 8 C atoms, in which one $—CH_2—$ group or, if present, a plurality of $—CH_2—$ groups may be replaced by $—O—$ or $—C(=O)—$, but two adjacent $—CH_2—$ groups cannot be replaced by $—O—$, and one or, if present, a plurality of $—CH_2—$ groups may be replaced by $—CH=CH—$ or $—C≡C—$ and in which one H atom or a plurality of H atoms may be replaced by F, $OR^{13}$, $N(R^{13})(R^{14})$ or $R^{15}$, or denote a single bond, $X^{11}$ denotes C, $Y^{11}$ to $Y^{14}$ each, independently of one another, denote methyl or ethyl, particularly preferably all denote either methyl or ethyl and very particularly preferably methyl, $Z^{11}$ to $Z^{14}$ on each occurrence, independently of one another, denote $—O—$, $—(C=O)—$, $—O—(C=O)—$, $—(C=O)—O—$, $—O—(C=O)—O—$, $—(N—R^{13})—$, or $—N—R^{13}—(C=O)—$, or may additionally be a single bond if $S^{11}$ is a single bond, with the proviso that both $Z^{11}$ and $Z^{12}$ do not simultaneously denote $—O—$, and, with the proviso that, if $S^{12}$ is a single bond, both $Z^{13}$ and $Z^{14}$ do not simultaneously denote $—O—$, and, however, if $—X^{11}[—R^{11}]_o—$ is a single bond, both $Z^{12}$ and $Z^{13}$ are not simultaneously $—O—$, $Z^{11}$ preferably denotes $—O—$, $Z^{13}$ preferably denotes a single bond, n*p denotes an integer from 3 to 10, preferably 3 to 8, p denotes 1 or 2, o denotes (3-p), in the case where p=1, n denotes an integer from 3 to 10, preferably 3, 4, 5, 6 or 8, particularly preferably 4, 6 or 8, very particularly preferably 4 or 6, and m denotes (10-n), and In the case where p=2, n denotes an integer from 2 to 4, preferably 2 or 3, particularly preferably 3, and m denotes (4-n),

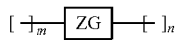

denotes an organic radical having (m+n) bonding sites, preferably having up to 4 bonding sites, preferably an alkanediyl, alkanetriyl or alkanetetrayl unit having 1 to 30 C atoms, in which, in addition to the m groups $R^{12}$ present in the molecule, but independently thereof, a further H atom may be replaced by $R^{12}$ or a plurality of further H atoms may be replaced by $R^{12}$, preferably an alkanetetrayl unit having one or two valences on each of the terminal C atoms, in which one —CH$_2$— group or a plurality of —CH$_2$— groups may be replaced by —O— or —(C=O)— in such a way that two O atoms are not bonded directly to one another, or a substituted or unsubstituted aromatic or heteroaromatic hydrocarbon radical having up to 10 valences, in which, in addition to the m groups $R^{12}$ present in the molecule, but independently thereof, a further H atom may be replaced by $R^{12}$ or a plurality of further H atoms may be replaced by $R^{12}$, and, in the case where p=1, —$X^{11}$[—$R^{11}$]$_o$— may alternatively also denote a single bond, and b) one or more compounds of the formula II

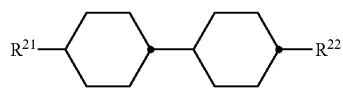

II in which $R^{21}$ denotes an unsubstituted alkyl radical having 1 to 7 C atoms or an unsubstituted alkenyl radical having 2 to 7 C atoms, preferably an n-alkyl radical, particularly preferably having 3, 4 or 5 C atoms, and $R^{22}$ denotes an unsubstituted alkenyl radical having 2 to 7 C atoms, preferably having 2, 3 or 4 C atoms, more preferably a vinyl radical or a 1-propenyl radical and in particular a vinyl radical, and/or c) one or more compounds selected from the group of the formulae III-1 to III-4, preferably of the formula III-2, and formula B,

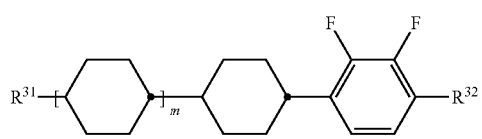

III-1

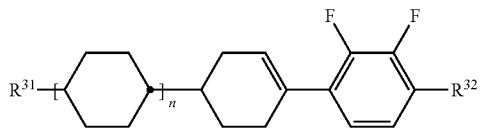

III-2

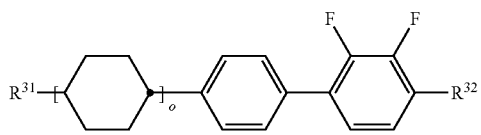

III-3

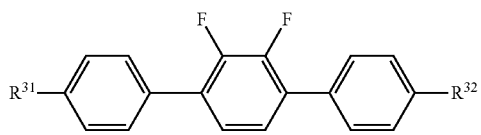

III-4

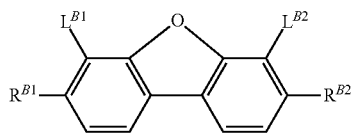

B in which $R^{31}$ denotes an unsubstituted alkyl radical having 1 to 7 C atoms, preferably an n-alkyl radical, particularly preferably having 2 to 5 C atoms, $R^{32}$ denotes an unsubstituted alkyl radical having 1 to 7 C atoms, preferably having 2 to 5 C atoms, or an unsubstituted alkoxy radical having 1 to 6 C atoms, preferably having 2, 3 or 4 C atoms, and m, n and o each, independently of one another, denote 0 or 1, $R^{B1}$ and $R^{B2}$ each, independently of one another, denote an unsubstituted alkyl radical, alkoxy radical, oxaalkyl radical or alkoxyalkyl radical having 1 to 7 C atoms, or an alkenyl radical or alkenyloxy radical having 2 to 7 C atoms, and $L^{B1}$ and $L^{B2}$ each, independently of one another, denote F or Cl, preferably F.

In the compounds of the formula I, the groups $N(R^{13})(R^{14})$ may preferably also be primary or secondary amines.

Preference is given to the following embodiments, independently:

P is 2,

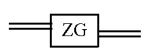

is an organic radical having 4 bonding sites, preferably an alkanetetrayl unit having 1 to 30 C atoms, in which, in addition to the m groups $R^{12}$ present in the molecule, but independently thereof, a further H atom may be replaced by $R^{12}$ or a plurality of further H atoms may be replaced by $R^{12}$, preferably an alkanetetrayl unit having one or two valences on each of the two terminal C atoms, in which one —CH$_2$— group or a plurality of —CH$_2$— groups may be replaced by —O— or —(C=O)— in such a way that two O atoms are not bonded directly to one another, or a substituted or unsubstituted aromatic or heteroaromatic hydrocarbon radical having up to 8 valences, in which, in addition to the m groups $R^{12}$ present in the molecule, but independently thereof, a further H atom may be replaced by $R^{12}$ or a plurality of further H atoms may be replaced by $R^{12}$,

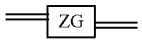

denotes

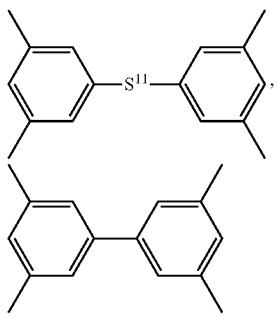

(biphenyl-1,1',3,3'-tetrayl),

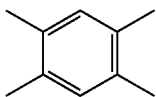

(benzene-1,2,4,5-tetrayl), or —CH$_2$—(CH—)—[CH$_2$]$_q$—(CH—)—CH$_2$— (where q∈{0, 1, 2, 3, to 16}) or >CH—[CH$_2$]$_r$—CH< (where r∈{0, 1, 2, 3, 4, 5 to 18}),

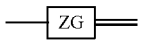

denotes

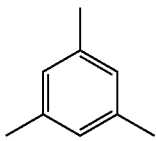

(benzene-1,3,5-triyl),

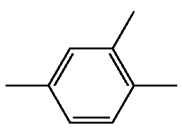

(benzene-1,2,4-triyl) or >CH—[CH$_2$]$_r$—CH$_2$— (where r∈{0, 1, 2, 3, 4, 5 to 18}) or

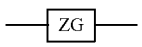

denotes —CH$_2$—[CH$_2$]$_r$—CH$_2$— (where r∈{0, 1, 2, 3, 4, 5 to 18}), octane-1,8-diyl, heptane-1,7-diyl, hexane-1,6-diyl, pentane-1,5-diyl, butane-1,4-diyl, propane-1,3-diyl, ethane-1,2-diyl, or

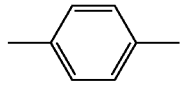

(1,4-phenylene),

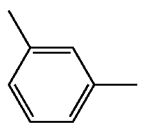

(1,3-phenylene),

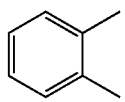

(1,2-phenylene) or

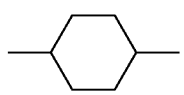

(1,4-cyclohexylene).

In the above and below embodiments where the ZG group has less than 4 groups bonded thereto, this means that there are a number of [$R^{12}$]$_m$— groups being H which make up the proper total for m and n, i.e., where p=1, m+n=10 and where p=2, m+n=4, In the present application, the elements all include their respective isotopes. In particular, one or more H in the compounds may be replaced by D, and this is also particularly preferred in some embodiments. A correspondingly high degree of deuteration of the corresponding compounds enables, for example, detection and recognition of the compounds. This is very helpful in some cases, in particular in the case of the compounds of the formula I.

In the present application, alkyl particularly preferably denotes straight-chain alkyl, in particular CH$_3$—, C$_2$H$_5$—, n-C$_3$H$_7$—, n-C$_4$H$_9$— or n-C$_5$H$_{11}$—, and alkenyl particularly preferably denotes CH$_2$=CH—, E-CH$_3$—CH=CH—, CH$_2$=CH—CH$_2$—CH$_2$—, E-CH$_3$—CH=CH—CH$_2$—CH$_2$— or E-(n-C$_3$H$_7$)—CH=CH—.

The liquid-crystalline media in accordance with the present application preferably comprise in total 1 ppm to 2500 ppm, preferably 1 ppm to 1500 ppm, preferably 1 to 600 ppm, even more preferably 1 to 250 ppm, preferably to 200 ppm, and very particularly preferably 1 ppm to 100 ppm, of compounds of the formula I.

In a preferred embodiment of the present invention, in the compounds of the formula I,

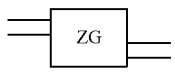

denotes

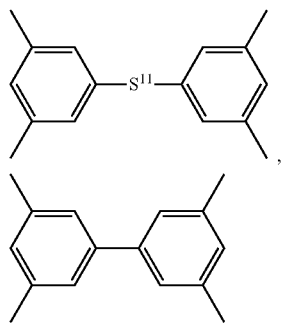

(biphenyl-1,1',3,3'-tetrayl) or

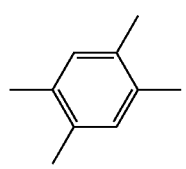

(benzene-1,2,4,5-tetrayl)

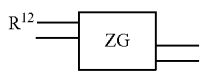

denotes

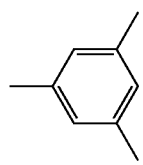

(benzene-1,3,5-triyl) or

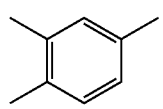

(benzene-1,2,4-triyl),

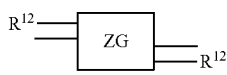

denotes —(CH$_2$—)$_2$, —(CH$_2$—)$_3$, —(CH$_2$—)$_4$, —(CH$_2$—)$_5$, —(CH$_2$—)$_6$, —(CH$_2$—)$_7$, —(CH$_2$—)$_8$, i.e.

ethane-1,2-diyl, propane-1,3-diyl, butane-1,4-diyl, pentane-1,5-diyl, hexane-1,6-diyl, heptane-1,7-diyl, octane-1,8-diyl,

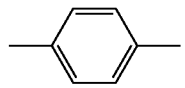

(1,4-phenylene),

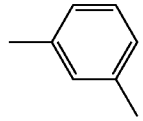

(1,3-phenylene),

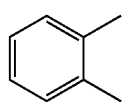

(1,2-phenylene) or

(trans-1,4-cyclohexylene) and/or

—Z$^{12}$—S$^{11}$—Z$^{11}$— on each occurrence, independently of one another, denotes —O—, —S$^{11}$—O—, —O—S$^{11}$—O—, —(C=O)—O—S$^{11}$—O—, —O—(C=O)—S$^{11}$—O—, —O—(C=O)—S$^{11}$—(C=O)—O—, —O—S$^{11}$—(C=O)—O—, —(C=O)—O—S$^{11}$—(C=O)—O—, or —(N—R$^{13}$)—S$^{11}$—O—, —N—R$^{13}$—(C=O)—S$^{11}$—(C=O)—O— or a single bond, preferably —O—, —S$^{11}$—O—, —O—S$^{11}$—O—, —(C=O)—O—S$^{11}$—O—, —O—(C=O)—S$^{11}$—O— or —O—S$^{11}$—(C=O)—O—, and/or R$^{11}$, if present, denotes alkyl, alkoxy or H, preferably H or alkyl, and/or R$^{12}$ denotes H, methyl, ethyl, propyl, isopropyl or 3-heptyl, or cyclohexyl.

In a preferred embodiment of the present application, in the compounds of the formula I,

denotes a group selected from the group of the formulae

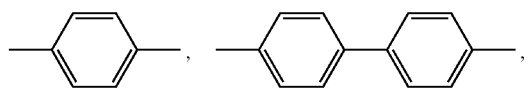

-continued

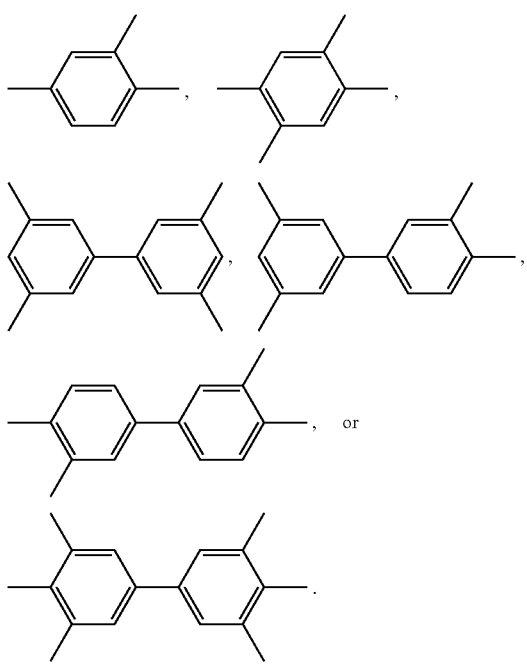

In a preferred embodiment of the present application, in the compounds of the formula I,

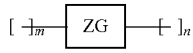

denotes a group selected from the group of the formulae

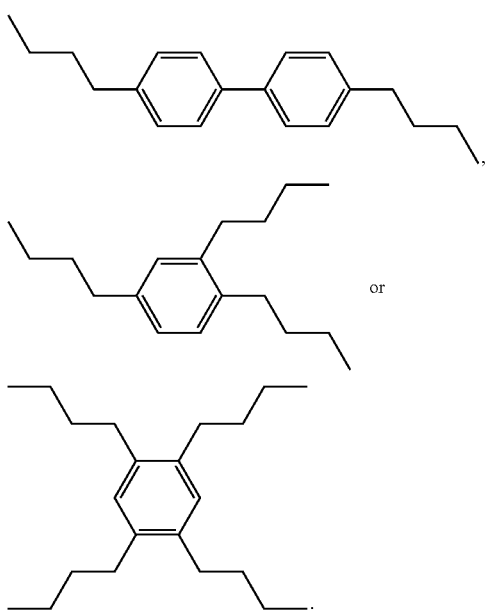

in a preferred embodiment of the present application, in the compounds of the formula I in which p preferably denotes 1,

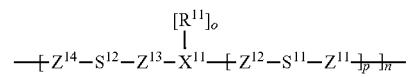

$-Z^{12}-S^{11}-Z^{11}-$, preferably $-O-S^{11}-O-$, $-S^{11}-O-$ or $-O-S^{11}-$, particularly preferably $-O-S^{11}-O-$.

In a preferred embodiment of the present application, in the compounds of the formula I, the group

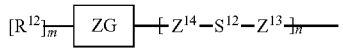

preferably denotes a group selected from the group of the formulae

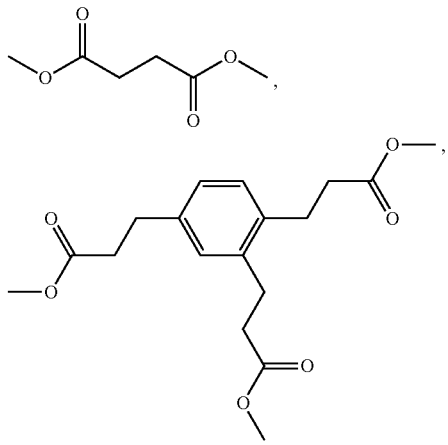

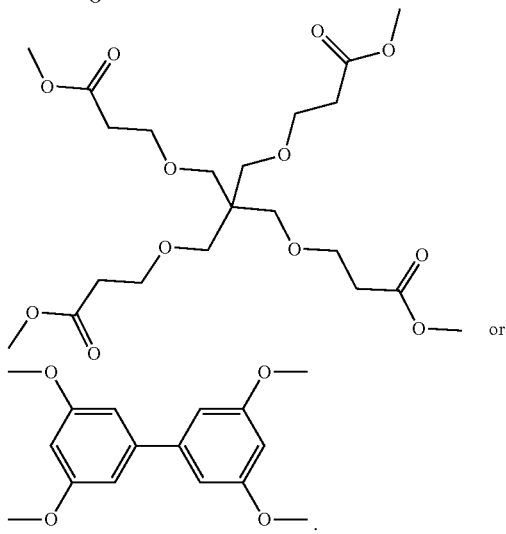

In a further preferred embodiment of the present application, which may be identical to or different from those described above, in the compounds of the formula I,

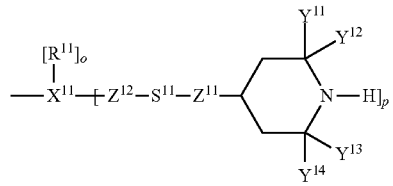

preferably denotes a group selected from the group of the formulae

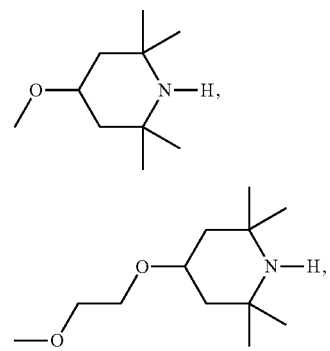

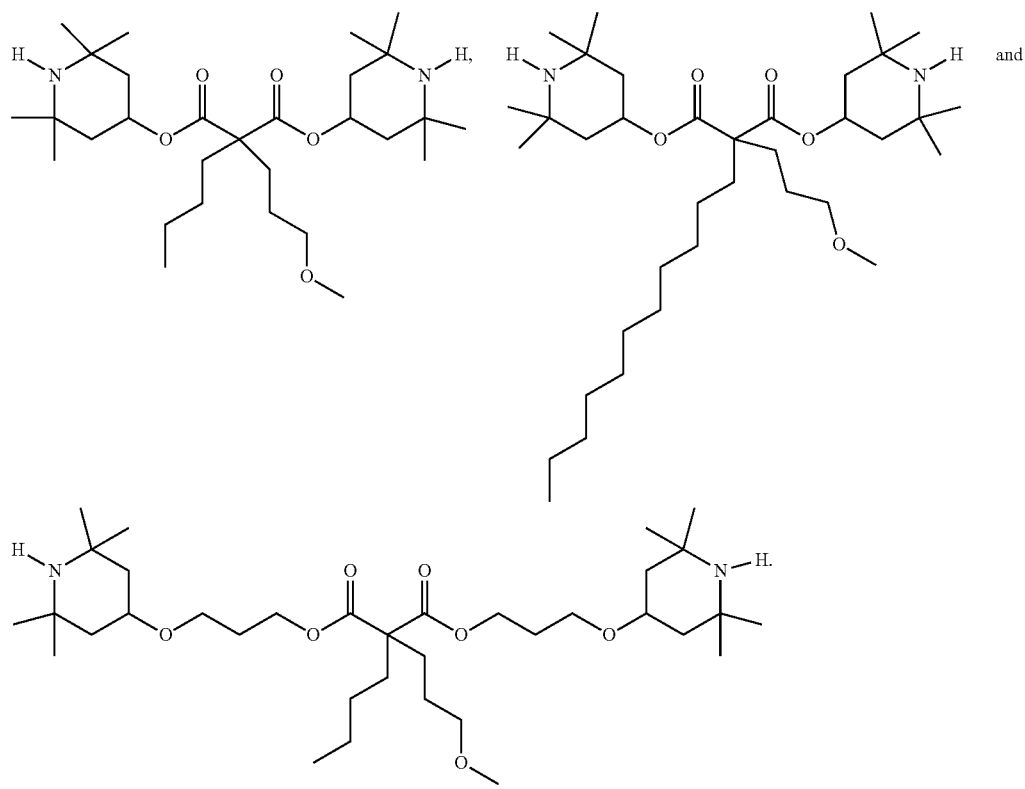

In a further preferred embodiment of the present invention, which may be identical to or different from those described above, in the compounds of the formula I, the group

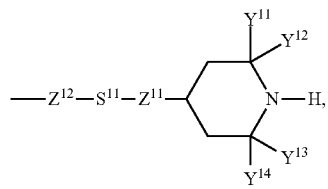

on each occurrence, independently of one another, denotes

-continued

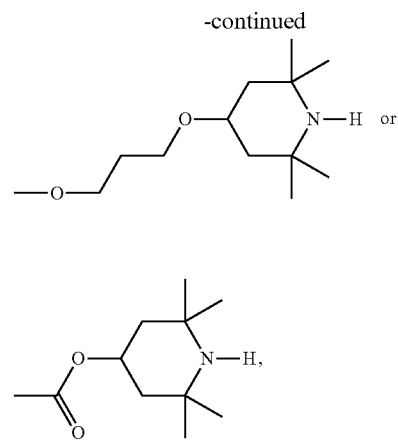

preferably

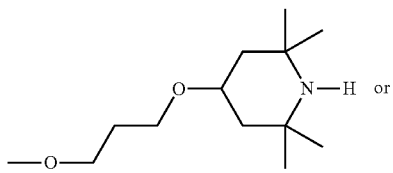

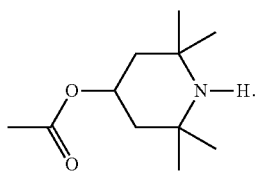

In a particularly preferred embodiment of the present invention, in the compounds of the formula I, all groups

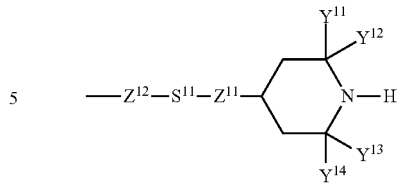

present have the same meaning.

These compounds are highly suitable as stabilisers in liquid-crystal mixtures. In particular, they stabilise the VHR of the mixtures against UV exposure.

In a preferred embodiment of the present invention, the media according to the invention comprise in each case one or more compounds of the formula I selected from the following group of the compounds of the formulae I-1 to I-13, preferably selected from the group of the compounds of the formulae I-3, I-5, I-6, I-7, I-8, I-9, I-10, I-12 and I-13, particularly preferably selected from the group of the compounds of the formulae I-6 to I-9 and very particularly preferably of the formula I-9,

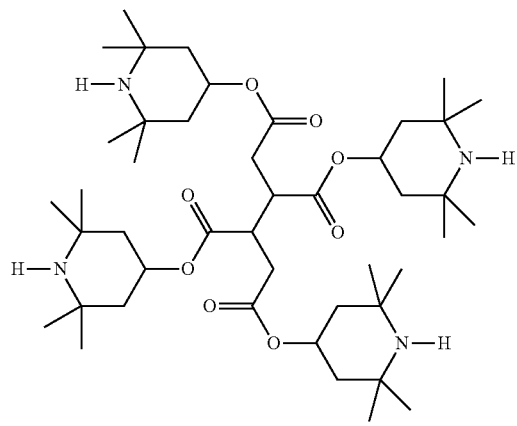

I-1

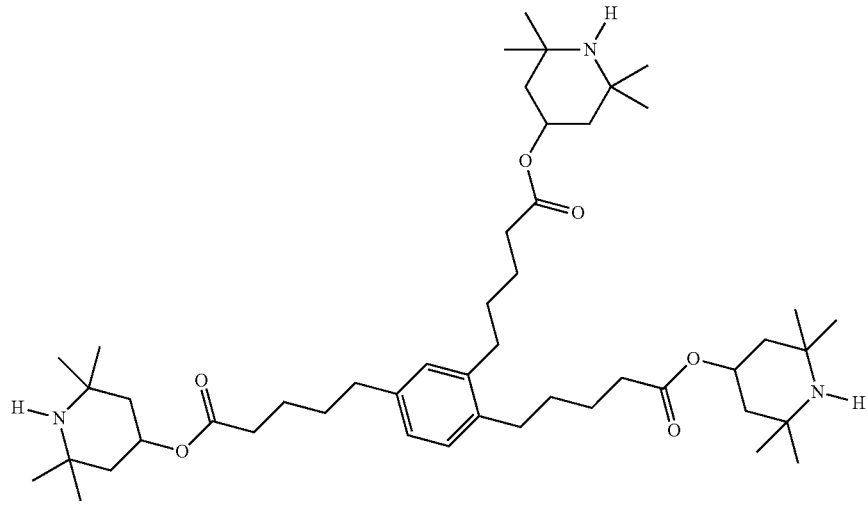

I-2

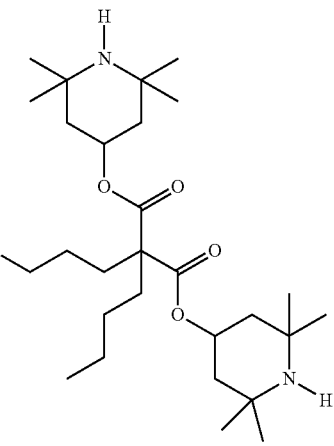
I-3
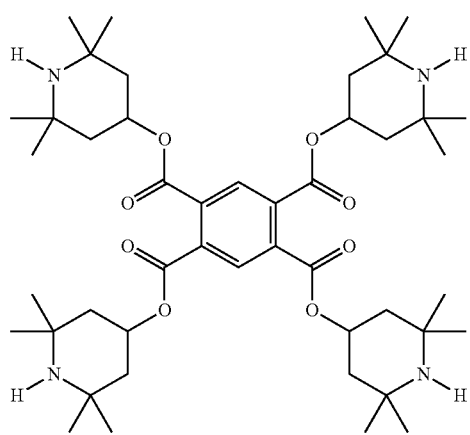
I-4

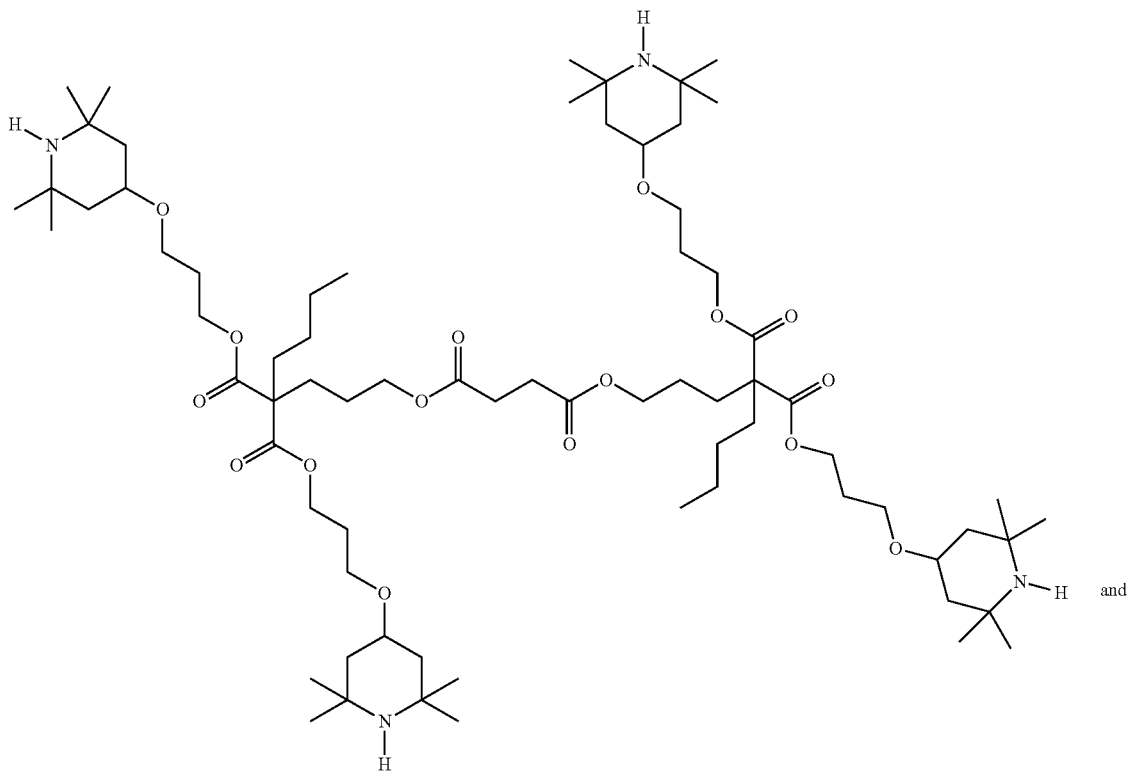
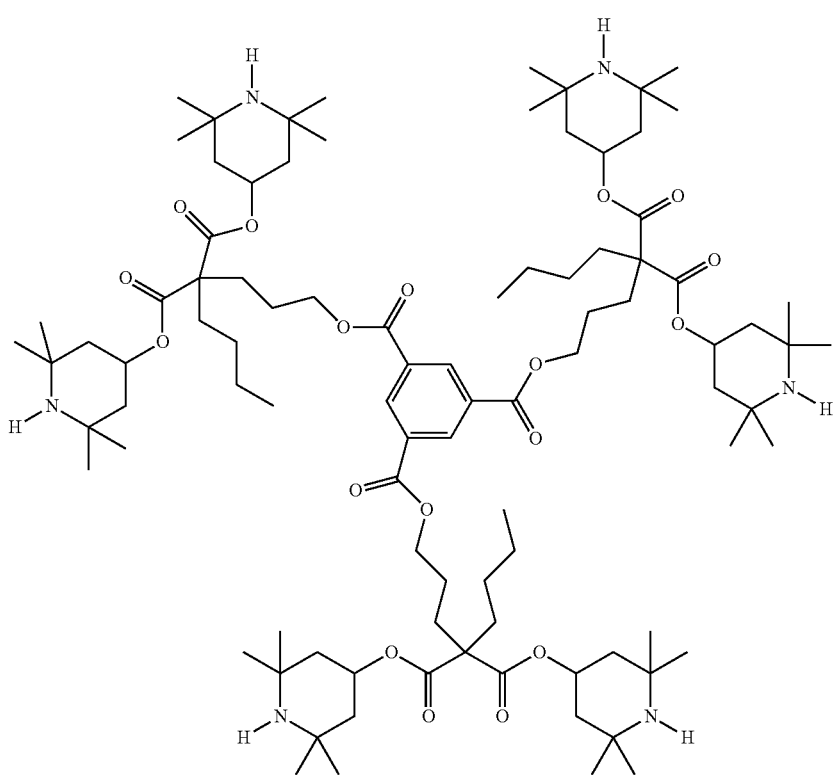

I-7
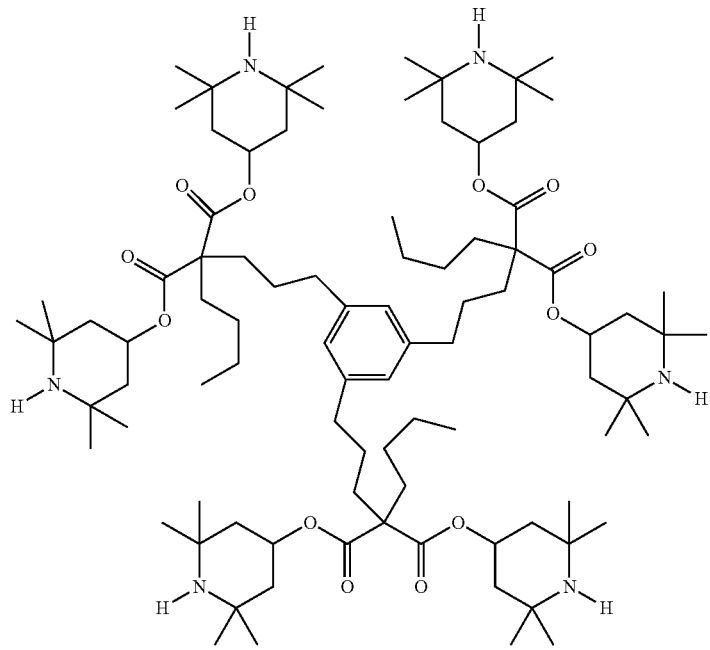
I-8
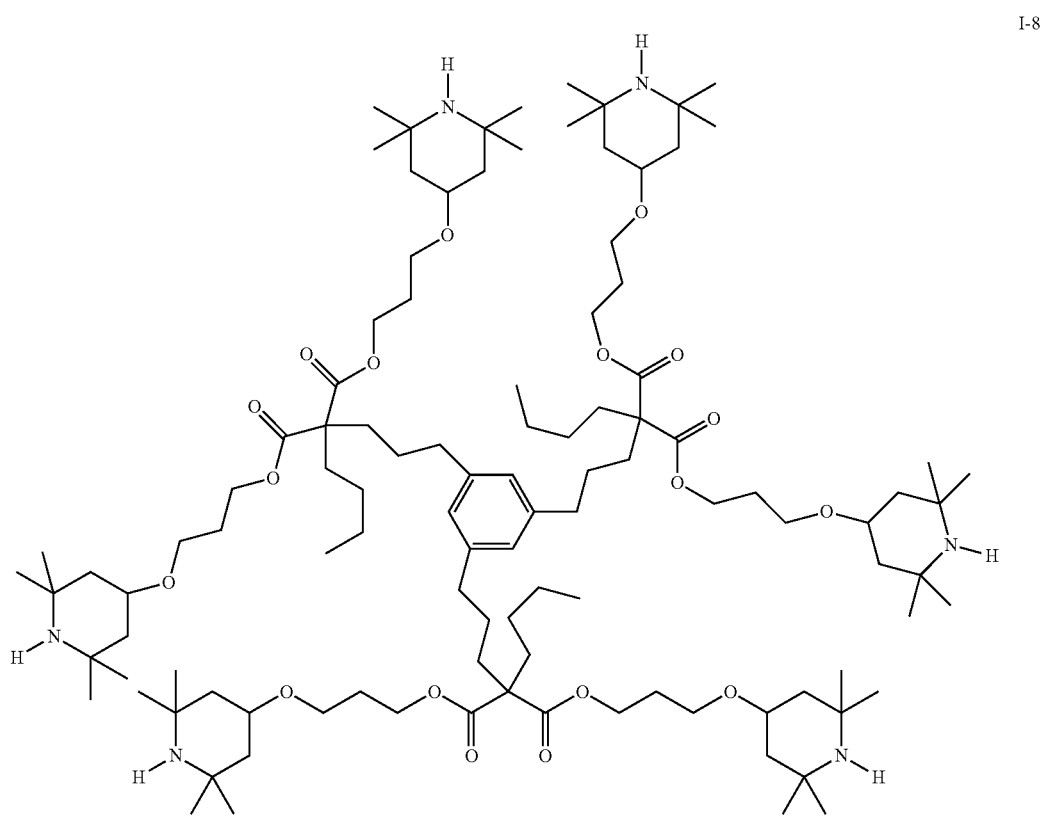

I-9
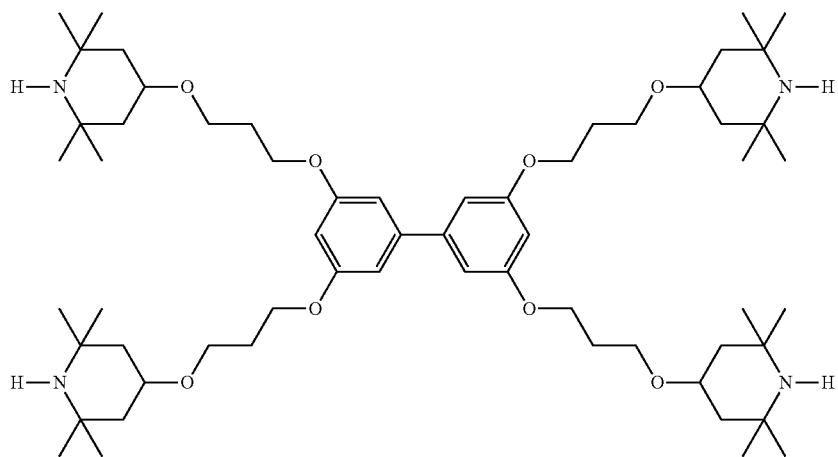
I-10
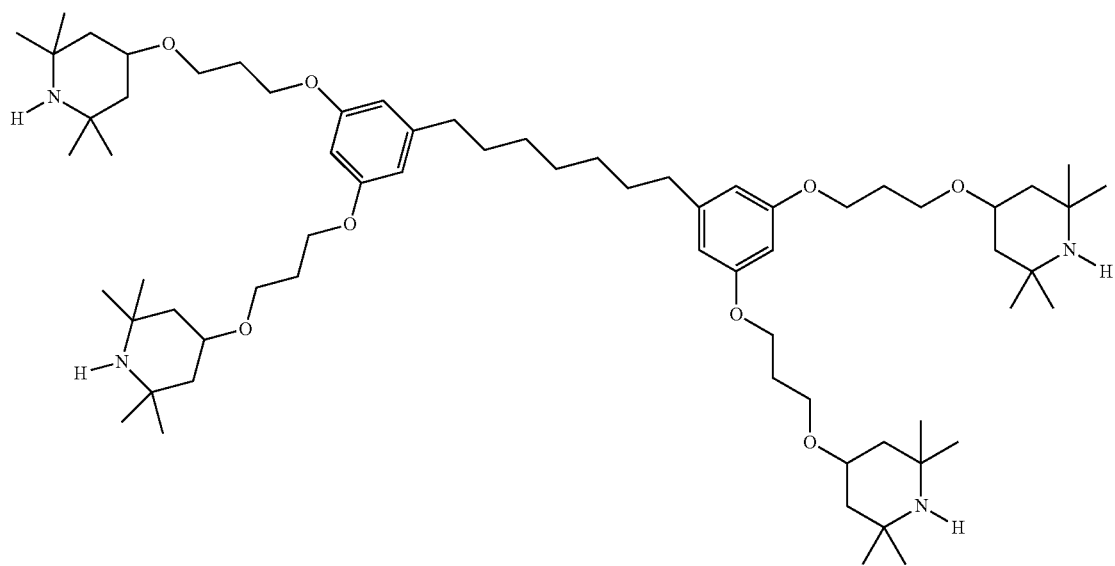
I-11
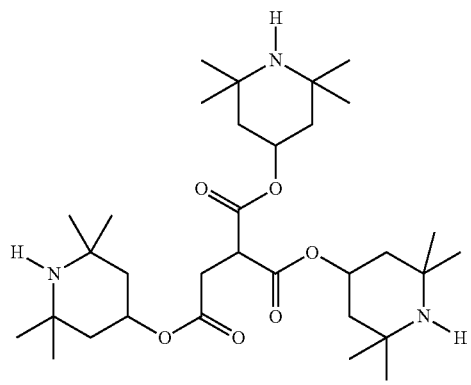

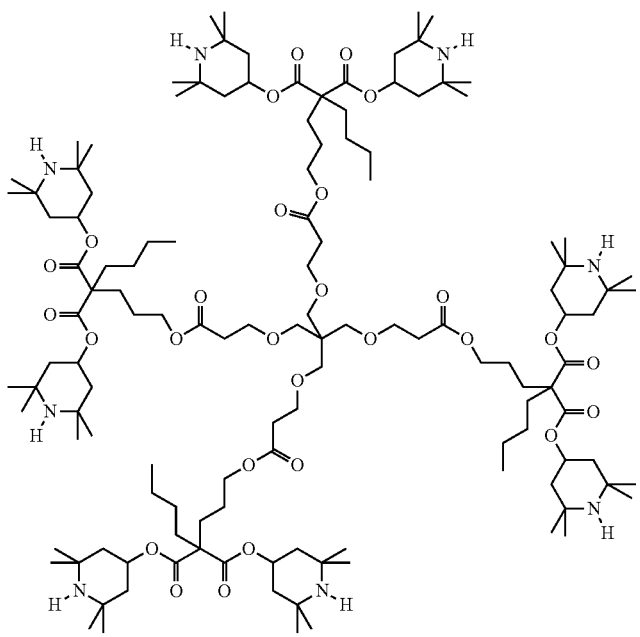

I-12

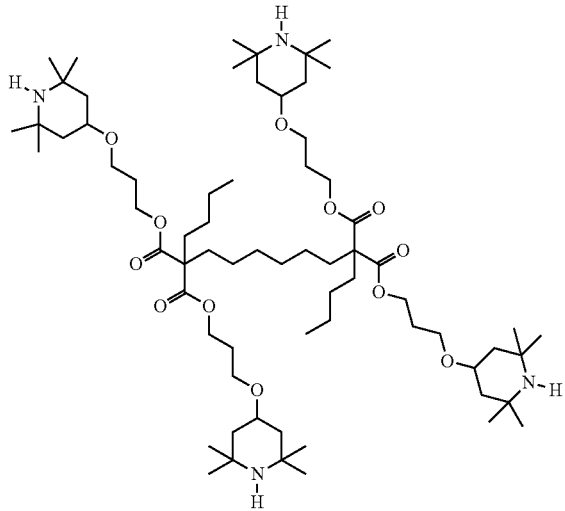

I-13

In an even more preferred embodiment of the present invention, the media according to the invention comprise in each case one or more compounds of the formula I selected from the group of the following compounds of the formulae I-1 and/or I-3 to I-7 and/or I-8 and/or I-9.

In an even more preferred embodiment of the present invention, the media according to the invention comprise in each case one or more compounds of the formula I selected from the group of the following compounds of the formulae I-8 and/or I-9.

In addition to the compounds of the formula I or the preferred sub-formulae thereof, the media in accordance with the present invention preferably comprise one or more dielectrically neutral compounds of the formula II in a total concentration in the range from 5% or more to 90% or less, preferably from 10% or more to 80% or less, particularly preferably from 20% or more to 70% or less.

The medium according to the invention preferably comprises one or more compounds selected from the group of the formulae III-1 to III-4 in a total concentration in the range from 10% or more to 80% or less, preferably from 15% or more to 70% or less, particularly preferably from 20% or more to 60% or less.

The medium according to the invention particularly preferably comprises one or more compounds of the formula III-1 in a total concentration in the range from 5% or more to 30% or less, one or more compounds of the formula III-2 in a total concentration in the range from 3% or more to 30% or less, one or more compounds of the formula III-3 in a total concentration in the range from 5% or more to 30% or less, one or more compounds of the formula III-4 in a total concentration in the range from 1% or more to 30% or less.

Preferred compounds of the formula II are the compounds selected from the group of the compounds of the formulae II-1 and II-2, preferably of the formula II-1,

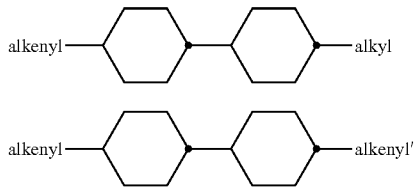

in which
alkyl denotes an alkyl radical having 1 to 7 C atoms, preferably having 2 to 5 C atoms,
alkenyl denotes an alkenyl radical having 2 to 5 C atoms, preferably having 2 to 4 C atoms, particularly preferably 2 C atoms,
alkenyl' denotes an alkenyl radical having 2 to 5 C atoms, preferably having 2 to 4 C atoms, particularly preferably having 2 to 3 C atoms.

In a preferred embodiment of the present invention, the media according to the invention comprise one or more compounds of the formula B, preferably in a concentration of 1 to 20%, particularly preferably 2 to 15% and very particularly preferably 3 to 9%,

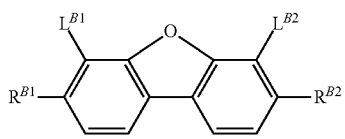

in which
$R^{B1}$ and $R^{B2}$ in each case, independently of one another, denote an unsubstituted alkyl radical, alkoxy radical, oxaalkyl radical or alkoxyalkyl radical having 1 to 7 C atoms, or an alkenyl radical or alkenyloxy radical having 2 to 7 C atoms, preferably both denote an alkoxy radical, and
$L^{B1}$ and $L^{B2}$ in each case, independently of one another, denote F or Cl, preferably F.

The media according to invention preferably comprise one or more compounds of the formula III-1, preferably one or more compounds selected from the group of the compounds of the formulae III-1-1 and III-1-2,

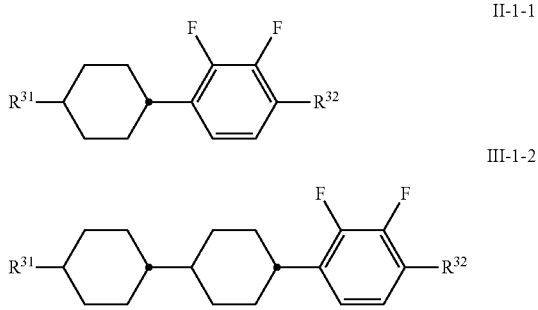

in which the parameters have the meanings given above in the case of formula III-1 and preferably $R^{31}$ denotes an alkyl radical having 2 to 5 C atoms, preferably having 3 to 5 C atoms, and
$R^{32}$ denotes an alkyl or alkoxy radical having 2 to 5 C atoms, preferably einen alkoxy radical having 2 to 4 C atoms, or an alkenyloxy radical having 2 to 4 C atoms.

The media according to the invention preferably comprise one or more compounds of the formula III-2, preferably one or more compounds selected from the group of the compounds of the formulae III-2-1 and III-2-2,

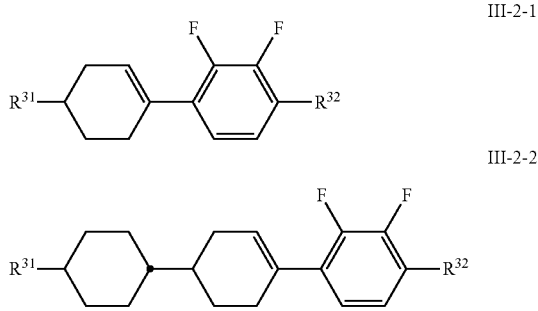

in which the parameters have the meanings given above in the case of formula III-2 and preferably
$R^{31}$ denotes an alkyl radical having 2 to 5 C atoms, preferably having 3 to 5 C atoms, and
$R^{32}$ denotes an alkyl or alkoxy radical having 2 to 5 C atoms, preferably an alkoxy radical having 2 to 4 C atoms, or an alkenyloxy radical having 2 to 4 C atoms.

The media according to the invention preferably comprise one or more compounds of the formula III-3, preferably one or more compounds selected from the group of the compounds of the formulae III-3-1 and III-3-2,

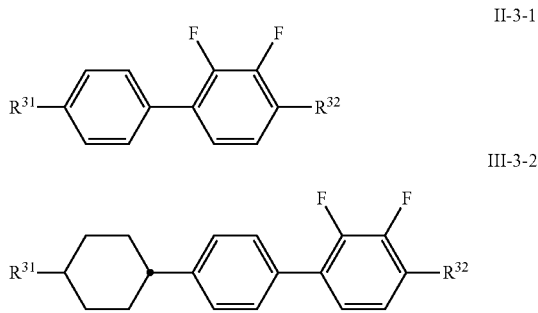

in which the parameters have the meanings given above in the case of formula III-3, preferably
$R^{31}$ denotes an alkyl radical having 2 to 5 C atoms, preferably having 3 to 5 C atoms, and
$R^{32}$ denotes an alkyl or alkoxy radical having 2 to 5 C atoms, preferably an alkoxy radical having 2 to 4 C atoms, or an alkenyloxy radical having 2 to 4 C atoms.

In a preferred embodiment, the media according to the invention comprise one or more compounds of the formula II selected from the group of the compounds of the formulae II-1 and II-2.

In a different preferred embodiment, the media according to the invention comprise no compounds of the formula II.

The media according to the invention preferably comprise the following compounds in the total concentrations indicated:

10-60% by weight of one or more compounds selected from the group of the compounds of the formulae III-1 to III-4 and/or 30-80% by weight of one or more compounds of the formulae IV and/or V, described below, where the total content of all compounds in the medium is 100%.

In a particularly preferred embodiment, the media according to the invention comprise one or more compounds selected from the group of the compounds of the formulae OH-1 to OH-6,

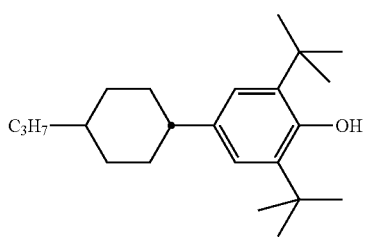

OH-1

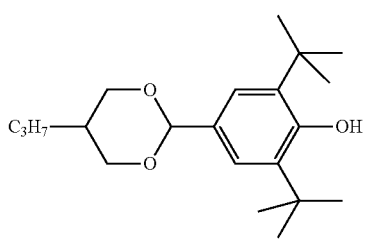

OH-2

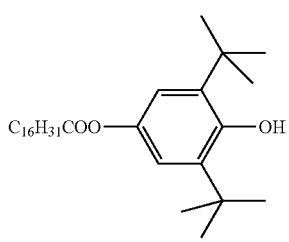

OH-3

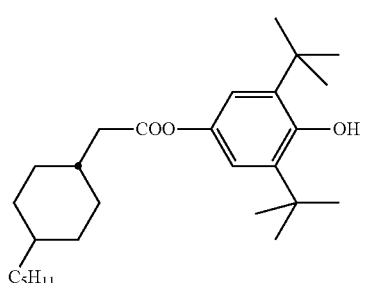

OH-4

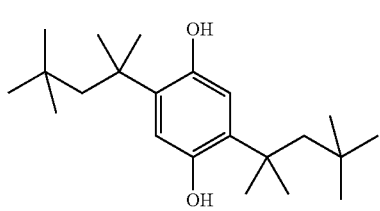

OH-5

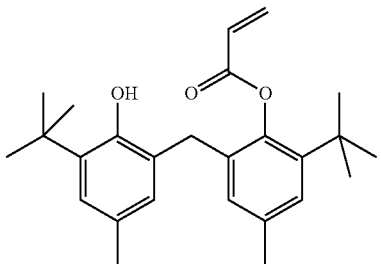

OH-6

These compounds are highly suitable for the stabilisation of the media against thermal loads.

In another preferred embodiment of the present invention, in which the media according to the invention comprise, in particular, one or more compounds of the formula I in which p denotes 2 and n denotes 2, 3 or 4, preferably 2 or 3, particularly preferably 3, these media have excellent stability.

In a further preferred embodiment of the present invention, the media according to the invention comprise at least in each case one or more compounds of the formula I in which p denotes 1 and n denotes 3, 4, 5 or 6, preferably 4, and the groups —$Z^{11}$—$S^{11}Z^{12}$— denote ω-bisoxyalkylene, i.e. —O—$S^{11}$—O—, these media have excellent stability.

The present invention also relates to electro-optical displays or electro-optical components which contain liquid-crystalline media according to the invention. Preference is given to electro-optical displays which are based on the IPS, FFS, VA or ECB effect preferably on the IPS or FFS effect, and in particular those which are addressed by means of an active-matrix addressing device.

Accordingly, the present invention likewise relates to the use of a liquid-crystalline medium according to the invention in an electro-optical display or in an electro-optical component, and to a process for the preparation of the liquid-crystalline media according to the invention, characterised in that one or more compounds of the formula I are mixed with one or more compounds of the formula II, preferably with one or more compounds of the sub-formula II-1, and with one or more further compounds, preferably selected from the group of the compounds of the formulae III-1 to III-4 and IV and V.

In addition, the present invention relates to a process for the stabilisation of a liquid-crystalline medium which comprises one or more compounds of the formula II and one or more compounds selected from the group of the compounds of the formulae III-1 to III-4, characterised in that one or more compounds of the formula I are added to the medium.

In a further preferred embodiment, the medium comprises one or more compounds of the formula IV,

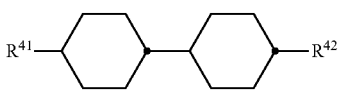

IV wherein $R^{41}$ denotes alkyl having 1 to 7 C atoms, preferably having 2 to 5 C atoms, and $R^{42}$ denotes alkyl having 1 to 7 C atoms or alkoxy having 1 to 6 C atoms, both preferably having 2 to 5 C atoms.

In a further preferred embodiment, the medium comprises one or more compounds of the formula IV, selected from the group of the compounds of the formulae IV-1 and IV-2,

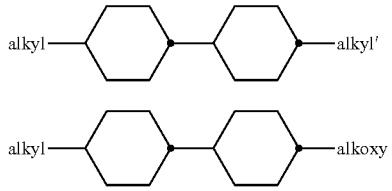

in which
alkyl and alkyl', independently of one another, denote alkyl having 1 to 7 C atoms, preferably having 2 to 5 C atoms,
alkoxy denotes alkoxy having 1 to 5 C atoms, preferably having 2 to 4 C atoms.

In a further preferred embodiment, the medium comprises one or more compounds of the formula V,

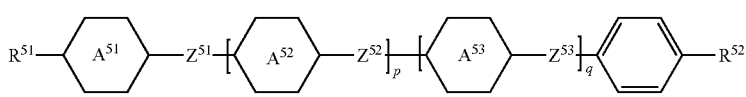

V in which
$R^{51}$ and $R^{52}$, independently of one another, have one of the meanings given for $R^{21}$ and $R^{22}$ and preferably denote alkyl having 1 to 7 C atoms, preferably n-alkyl, particularly preferably n-alkyl having 1 to 5 C atoms, alkoxy having 1 to 7 C atoms, preferably n-alkoxy, particularly preferably n-alkoxy having 2 to 5 C atoms, alkoxyalkyl, alkenyl or alkenyloxy having 2 to 7 C atoms, preferably having 2 to 4 C atoms, preferably alkenyloxy,

to

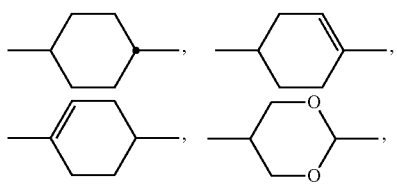

if present, in each case, independently of one another, denote

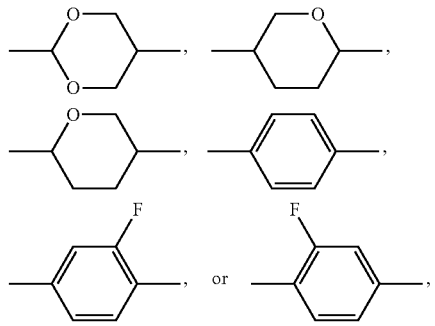

preferably

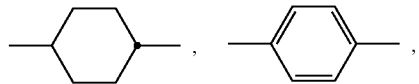

-continued

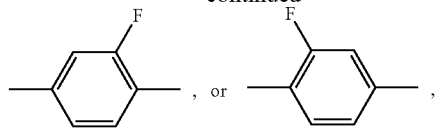

preferably

denotes

and, if present,

preferably denotes

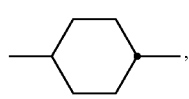

$Z^{51}$ to $Z^{53}$ each, independently of one another, denote —CH$_2$—CH$_2$—, —CH$_2$—O—, —CH=CH—, —C≡C—, —COO— or a single bond, preferably —CH$_2$—CH$_2$—, —CH$_2$—O— or a single bond and particularly preferably a single bond, p and q of formula V each, independently of one another, denote 0 or 1, (p+q) for formula V preferably denotes 0 or 1.

In a further preferred embodiment, the medium comprises one or more compounds of the formula V selected from the group of the compounds of the formulae V-1 to V-10, preferably selected from the group of the compounds of the formulae V-1 to V-5,

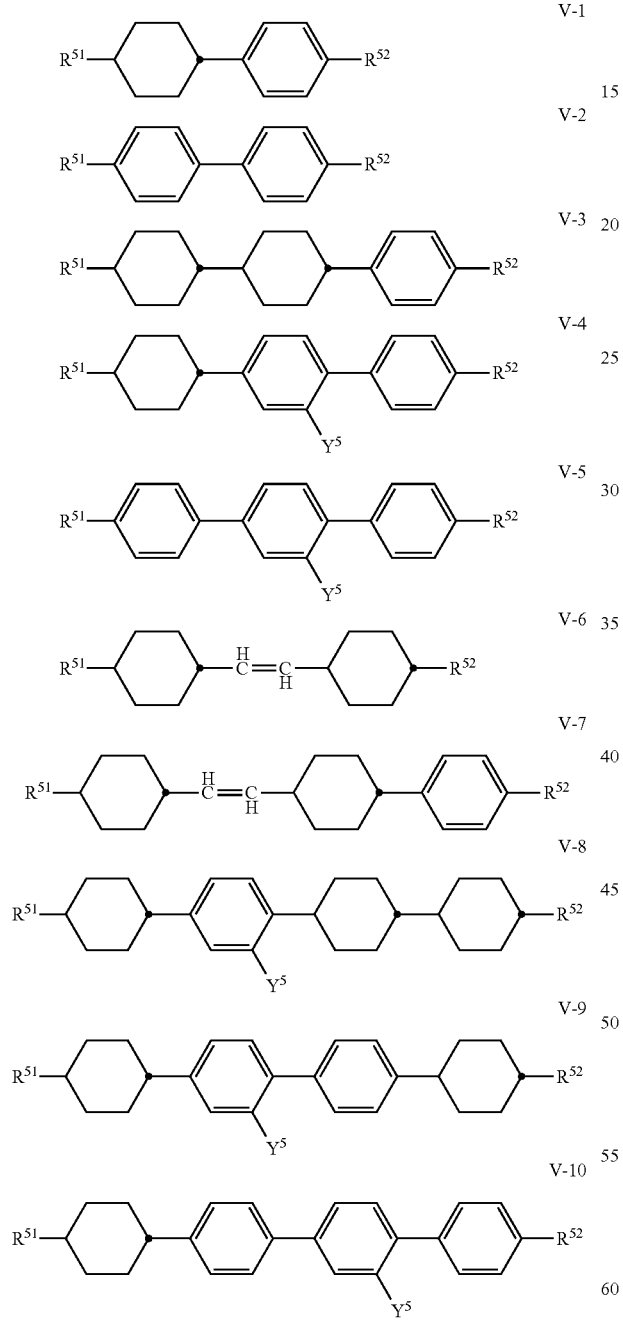

in which the parameters R$^{51}$ and R$^{52}$ have the meanings given above under formula V, and Y$^5$ denotes H or F, and preferably R$^{51}$ denotes alkyl having 1 to 7 C atoms or alkenyl having 2 to 7 C atoms, and R$^{52}$ denotes alkyl having 1 to 7 C atoms, alkenyl having 2 to 7 C atoms or alkoxy having 1 to 6 C atoms, preferably alkyl or alkenyl, particularly preferably alkenyl.

In a further preferred embodiment, the medium comprises one or more compounds of the formula V-1 selected from the group of the compounds of the formulae V-1a and V-1 b, preferably of the formula V-1 b,

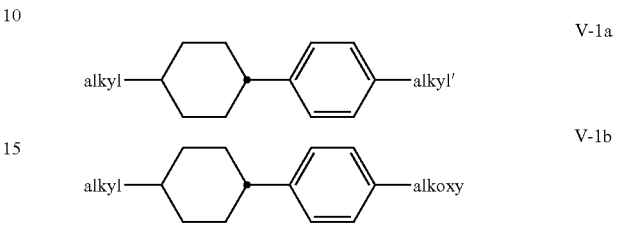

in which alkyl and alkyl', independently of one another, denote alkyl having 1 to 7 C atoms, preferably having 2 to 5 C atoms, alkoxy denotes alkoxy having 1 to 5 C atoms, preferably having 2 to 4 C atoms.

In a further preferred embodiment, the medium comprises one or more compounds of the formula V-3 selected from the group of the compounds of the formulae V-3a and V-3b,

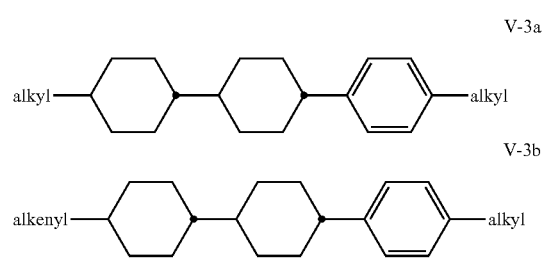

in which alkyl and alkyl', independently of one another, denote alkyl having 1 to 7 C atoms, preferably having 2 to 5 C atoms, and alkenyl denotes alkenyl having 2 to 7 C atoms, preferably having 2 to 5 C atoms.

In a further preferred embodiment, the medium comprises one or more compounds of the formula V-4 selected from the group of the compounds of the formulae V-4a and V-4b,

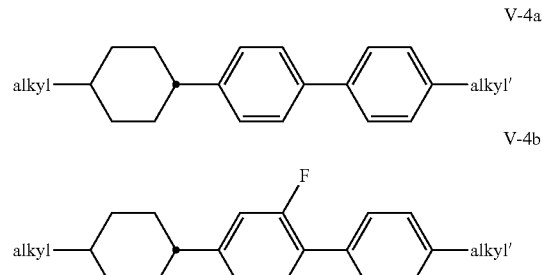

in which alkyl and alkyl', independently of one another, denote alkyl having 1 to 7 C atoms, preferably having 2 to 5 C atoms.

In a further preferred embodiment, the medium comprises one or more compounds of the formula III-4, preferably of the formula III-4-a,

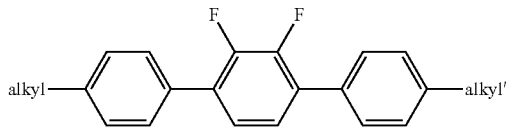

III-4-a in which
alkyl and alkyl', independently of one another, denote alkyl having 1 to 7 C atoms, preferably having 2 to 5 C atoms.

The liquid-crystal media in accordance with the present invention may comprise one or more chiral compounds.

Particularly preferred embodiments of the present invention meet one or more of the following conditions, where the acronyms (abbreviations) are explained in Tables A to C and illustrated by examples in Table D.

i. The liquid-crystalline medium has a birefringence of 0.060 or more, particularly preferably 0.070 or more.
ii. The liquid-crystalline medium has a birefringence of 0.130 or less, particularly preferably 0.120 or less.
iii. The liquid-crystalline medium has a birefringence in the range from 0.090 or more to 0.120 or less.
iv. The liquid-crystalline medium has a negative dielectric anisotropy having a value of 2.0 or more, particularly preferably 3.0 or more.
v. The liquid-crystalline medium has a negative dielectric anisotropy having a value of 5.5 or less, particularly preferably 5.0 or less.
vi. The liquid-crystalline medium has a negative dielectric anisotropy having a value in the range from 3.6 or more to 5.2 or less.
vii. The liquid-crystalline medium comprises one or more particularly preferred compounds of the formula II selected from the sub-formulae given below:

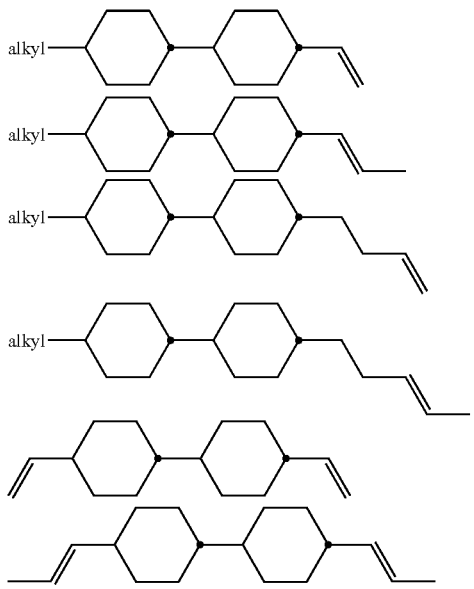

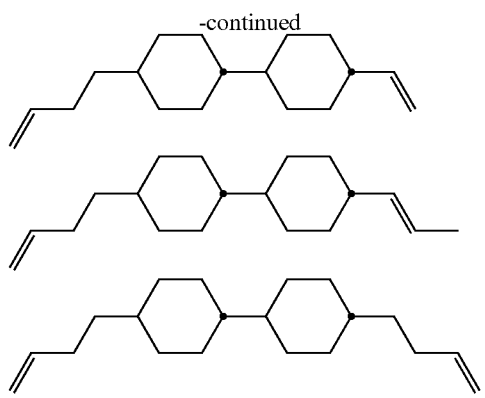

in which alkyl has the meaning given above and preferably, in each case independently of one another, denotes alkyl having 1 to 6, preferably having 2 to 5, C atoms and particularly preferably n-alkyl.

viii. The total concentration of the compounds of the formula II in the mixture as a whole is 25% or more, preferably 30% or more, and is preferably in the range from 25% or more to 49% or less, particularly preferably in the range from 29% or more to 47% or less, and very particularly preferably in the range from 37% or more to 44% or less.
ix. The liquid-crystalline medium comprises one or more compounds of the formula II selected from the group of the compounds of the following formulae: CC-n-V and/or CC-n-Vm, particularly preferably CC-3-V, preferably in a concentration of up to 50% or less, particularly preferably up to 42% or less, and optionally additionally CC-3-V1, preferably in a concentration of up to 15% or less, and/or CC-4-V, preferably in a concentration of up to 20% or less, particularly preferably up to 10% or less.
x. The total concentration of the compounds of the formula CC-3-V in the mixture as a whole is 20% or more, preferably 25% or more.
xi. The proportion of compounds of the formulae III-1 to III-4 in the mixture as a whole is 50% or more and preferably 75% or less.
xii. The liquid-crystalline medium essentially consists of compounds of the formulae I, II, III-1 to III-4, IV and V, preferably of compounds of the formulae I, II and III-1 to III-4.
xiii. The liquid-crystalline medium comprises one or more compounds of the formula IV, preferably in a total concentration of 5% or more, in particular 10% or more, and very particularly preferably 15% or more to 40% or less.

The invention furthermore relates to an electro-optical display having active-matrix addressing based on the VA or ECB effect, characterised in that it contains, as dielectric, a liquid-crystalline medium in accordance with the present invention.

The liquid-crystal mixture preferably has a nematic phase range having a width of at least 80 degrees and a flow viscosity $v_{20}$ of at most 30 mm$^2 \cdot$s$^{-1}$ at 20° C.

The liquid-crystal mixture according to the invention has a $\Delta\varepsilon$ of $-0.5$ to $-8.0$, in particular $-1.5$ to $-6.0$, and very particularly preferably $-2.0$ to $-5.0$, where $\Delta\varepsilon$ denotes the dielectric anisotropy.

The rotational viscosity $\gamma_1$ is preferably 150 mPa·s or less, in particular 120 mPa·s or less and very particularly preferably 120 mPa·s or less.

The mixtures according to the invention are suitable for all IPS and FFS-TFT applications. They are furthermore suitable for all VA applications, such as, for example, VAN, MVA, (S)-PVA and ASV applications, and PALC applications having negative Δε.

The nematic liquid-crystal mixtures in the displays according to the invention generally comprise two components A and B, which themselves consist of one or more individual compounds.

The liquid-crystalline media according to the invention preferably comprise 4 to 15, in particular 5 to 12, and particularly preferably 10 or less, compounds. These are preferably selected from the group of the compounds of the formulae I, II and III-1 to III-4, and/or IV and/or V.

The liquid-crystalline media according to the invention may optionally also comprise more than 18 compounds. In this case, they preferably comprise 18 to 25 compounds.

Besides compounds of the formulae I to V, other constituents may also be present, for example in an amount of up to 45%, but preferably up to 35%, in particular up to 10%, of the mixture as a whole.

The media according to the invention may optionally also comprise a dielectrically positive component, whose total concentration is preferably 10% or less, based on the entire medium.

In a preferred embodiment, the liquid-crystal media according to the invention comprise in total, based on the mixture as a whole, 100 ppm or more to 2500 ppm or less, preferably 300 ppm or more to 2000 ppm or less, particularly preferably 500 ppm or more to 1500 ppm or less and very particularly preferably 700 ppm or more to 1200 ppm or less, of the compound of the formula I, 20% or more to 60% or less, preferably 25% or more to 50% or less, particularly preferably 30% or more to 45% or less, of compounds of the formula II, and 50% or more to 70% or less of compounds of the formulae III-1 to III-4 and/or B.

In a preferred embodiment, the liquid-crystal media according to the invention comprise compounds selected from the group of the compounds of the formulae I, II, III-1 to III-4, IV and V, preferably selected from the group of the compounds of the formulae I, II and III-1 to III-4 and/or B; they preferably consist predominantly, particularly preferably essentially and very particularly preferably virtually completely of the compounds of the said formulae.

The liquid-crystal media according to the invention preferably have a nematic phase from in each case at least −20° C. or less to 70° C. or more, particularly preferably from −30° C. or less to 80° C. or more, very particularly preferably from −40° C. or less to 85° C. or more and most preferably from −40° C. or less to 90° C. or more.

The expression "have a nematic phase" here means on the one hand that no smectic phase and no crystallisation are observed at low temperatures at the corresponding temperature and on the other hand that no clearing occurs on heating out of the nematic phase. The investigation at low temperatures is carried out in a flow viscometer at the corresponding temperature and checked by storage in test cells having a cell thickness corresponding to the electro-optical application for at least 100 hours. If the storage stability at a temperature of −20° C. in a corresponding test cell is 1000 h or more, the medium is regarded as stable at this temperature. At temperatures of −30° C. and −40° C., the corresponding times are 500 h and 250 h respectively. At high temperatures, the clearing point is measured in capillaries by conventional methods. In addition, the shelf life at low temperatures in bulk (1 ml of sample) is determined in glass vials at temperatures of −20° C. or −30° C. At these temperatures, preferably at −30° C., the stable shelf lives are preferably 120 h or more, particularly preferably 240 h more.

In a preferred embodiment, the liquid-crystal media according to the invention are characterised by optical anisotropy values in the moderate to low range. The birefringence values are preferably in the range from 0.065 or more to 0.130 or less, particularly preferably in the range from 0.080 or more to 0.120 or less and very particularly preferably in the range from 0.085 or more to 0.110 or less.

In this embodiment, the liquid-crystal media according to the invention have negative dielectric anisotropy and relatively high absolute values of the dielectric anisotropy (|Δε|) which are preferably in the range from 2.7 or more to 5.3 or less, preferably to 4.5 or less, preferably from 2.9 or more to 4.5 or less, particularly preferably from 3.0 or more to 4.0 or less and very particularly preferably from 3.5 or more to 3.9 or less.

The liquid-crystal media according to the invention have relatively low values for the threshold voltage ($V_0$) in the range from 1.7 V or more to 2.5 V or less, preferably from 1.8 V or more to 2.4 V or less, particularly preferably from 1.9 V or more to 2.3 V or less and very particularly preferably from 1.95 V or more to 2.1 V or less.

In a further preferred embodiment, the liquid-crystal media according to the invention preferably have relatively low values of the average dielectric anisotropy ($\varepsilon_{av.} \equiv (\varepsilon_\| + 2\varepsilon_\perp)/3$) which are preferably in the range from 5.0 or more to 7.0 or less, preferably from 5.5 or more to 6.5 or less, still more preferably from 5.7 or more to 6.4 or less, particularly preferably from 5.8 or more to 6.2 or less and very particularly preferably from 5.9 or more to 6.1 or less.

In addition, the liquid-crystal media according to the invention have high values for the VHR in liquid-crystal cells.

In freshly filled cells at 20° C. in the cells, the VHR values are preferably greater than or equal to 95%, preferably greater than or equal to 97%, particularly preferably greater than or equal to 98% and very particularly preferably greater than or equal to 99%, and after 5 minutes in the oven at 100° C. in the cells, these are greater than or equal to 90%, preferably greater than or equal to 93%, particularly preferably greater than or equal to 96% and very particularly preferably greater than or equal to 98%.

In general, liquid-crystal media having a low addressing voltage or threshold voltage here have a lower VHR than those having a higher addressing voltage or threshold voltage, and vice versa.

These preferred values for the individual physical properties are preferably also in each case maintained by the media according to the invention in combination with one another.

In the present application, the term "compounds", also written as "compound(s)", means both one and also a plurality of compounds, unless explicitly indicated otherwise.

Unless indicated otherwise, the individual compounds are generally employed in the mixtures in concentrations in each case from 1% or more to 30% or less, preferably from 2% or more to 30% or less and particularly preferably from 3% or more to 16% or less.

In a preferred embodiment, the liquid-crystalline media according to the invention comprise
the compound of the formula I,
one or more compounds of the formula II, preferably selected from the group of the compounds of the formulae CC-n-V and CC-n-Vm, preferably CC-3-V, CC-3-V1, CC-4-V and CC-5-V, particularly preferably selected from the group of the compounds CC-3-V, CC-3-V1 and CC-4-V, very particularly preferably the compound CC-3-V, and optionally additionally the compound(s) CC-4-V and/or CC-3-V1, one or more compounds of the formula III-1-1, preferably of the formula CY-n-Om, selected from the group of the compounds of the formulae CY-3-O2, CY-3-O4, CY-5-O2 and CY-5-O4, one or more compounds of the formula III-1-2, preferably selected from the group of the compounds of the formulae CCY-n-m and CCY-n-Om, preferably of the formula CCY-n-Om, preferably selected from the group of the compounds of the formulae CCY-3-O2, CCY-2-O2, CCY-3-O1, CCY-3-O3, CCY-4-O2, CCY-3-O2 and CCY-5-O2, optionally, preferably obligatorily, one or more compounds of the formula III-2-2, preferably of the formula CLY-n-Om, preferably selected from the group of the compounds of the formulae CLY-2-O4, CLY-3-O2, CLY-3-O3, one or more compounds of the formula III-3-2, preferably of the formula CPY-n-Om, preferably selected from the group of the compounds of the formulae CPY-2-O2 and CPY-3-O2, CPY-4-O2 and CPY-5-O2, one or more compounds of the formula III-4, preferably of the formula PYP-n-m, preferably selected from the group of the compounds of the formulae PYP-2-3 and PYP-2-4.

The compounds of the formula I according to the invention, or the compounds of the formula I to be employed in accordance with the invention, can advantageously be prepared in accordance with the following reaction schemes.

Synthesis Scheme 1

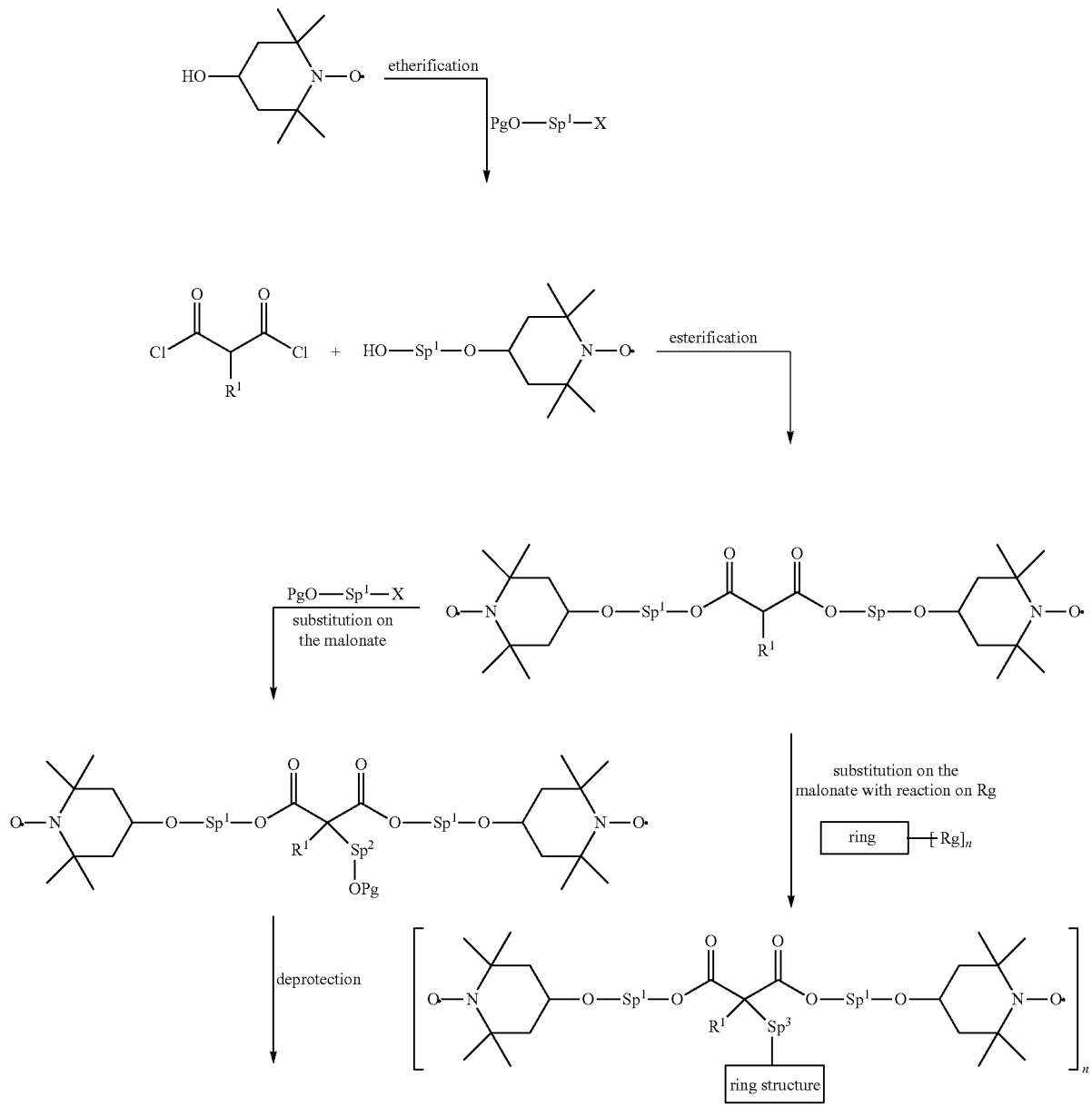

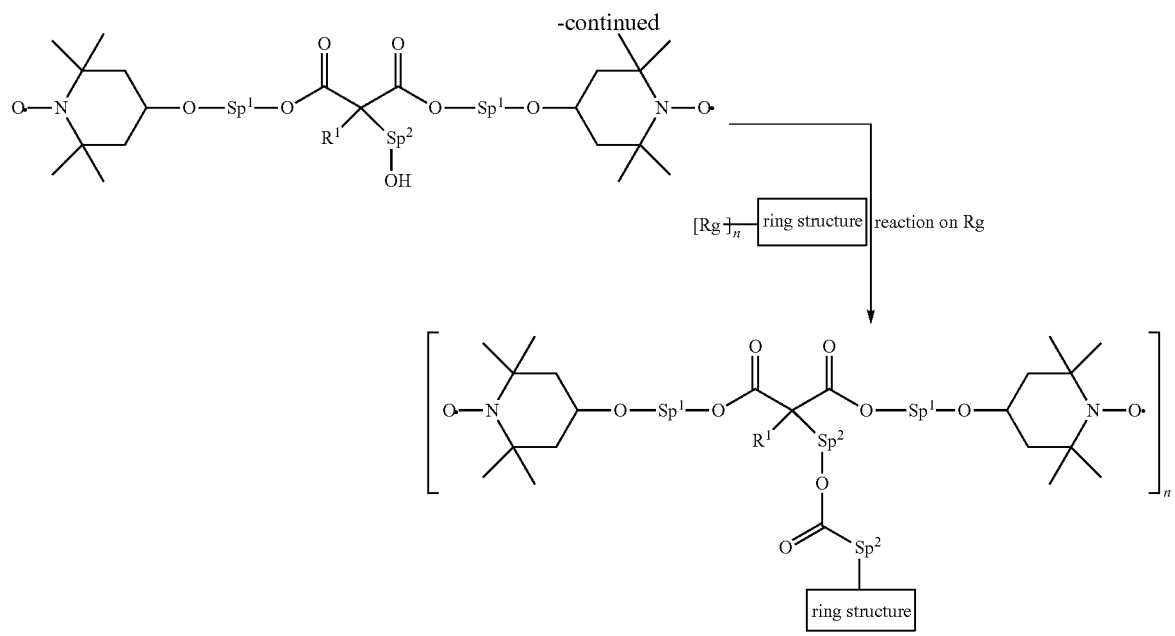
in which n preferably denotes 2, 3 or 4, particularly preferably 3 or 4.
Synthesis Scheme 2
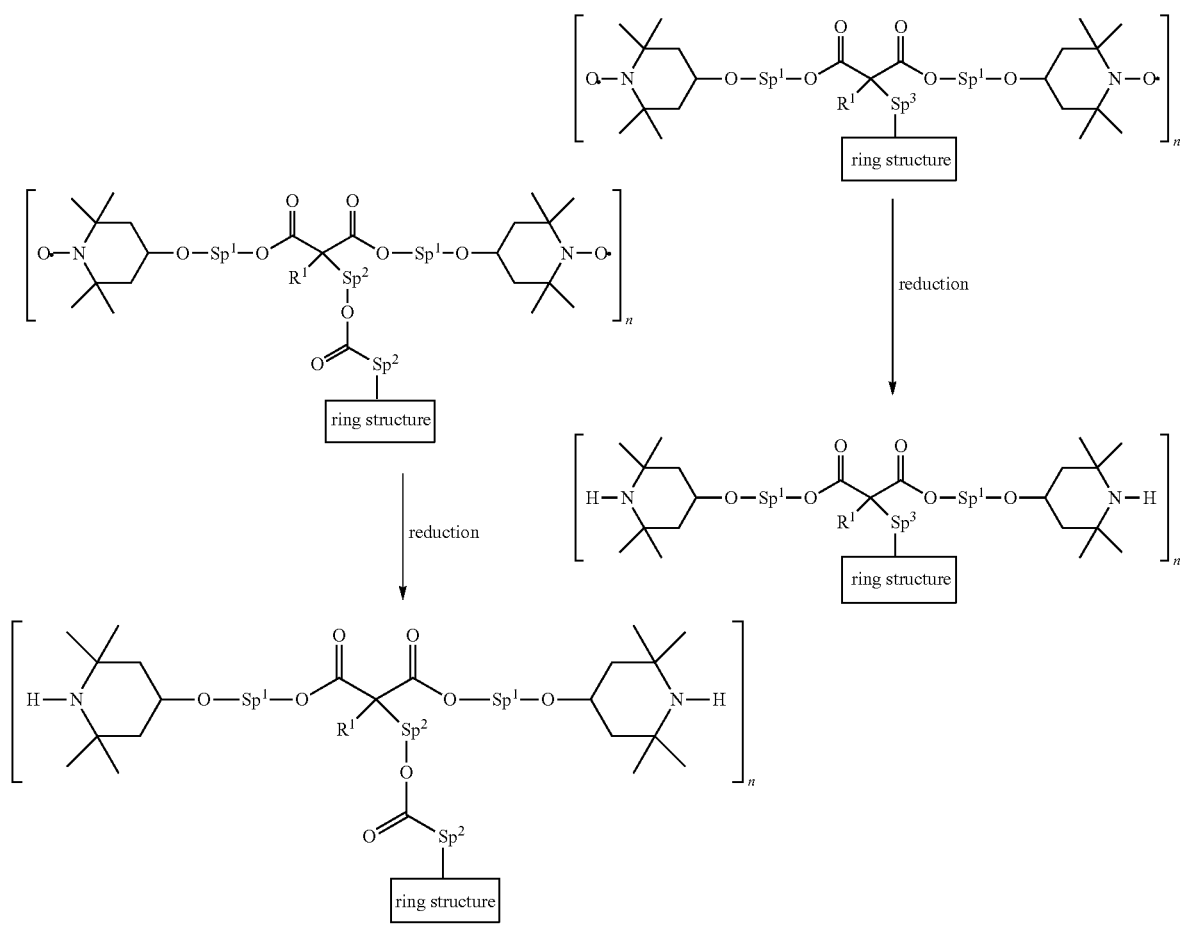

in which n preferably denotes 2, 3 or 4, particularly preferably 3 or 4.

Synthesis Scheme 3

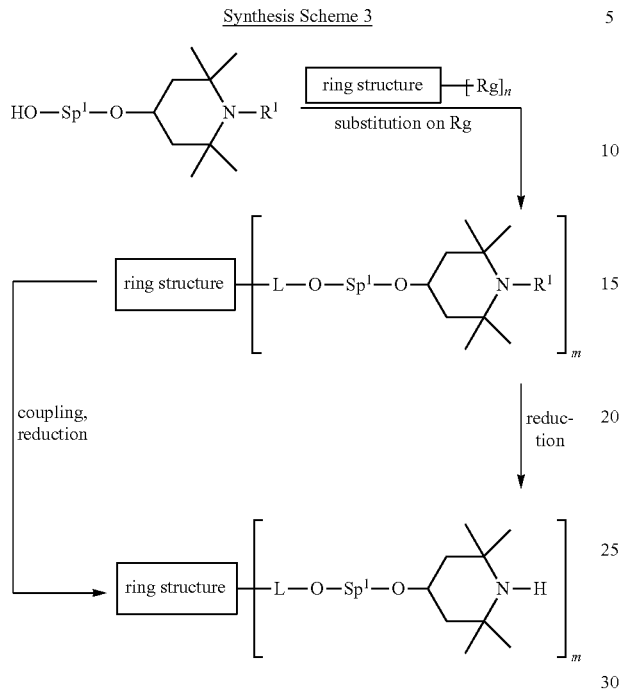

in which m denotes an integer from 3 to 6, particularly preferably 4 or 6.

In the reaction schemes above, Pg denotes a protecting group and Rg denotes a leaving group and the parameter n has the meaning given in the case of formula I, L denotes a linker unit, furthermore $R^1$ has the meaning benzyl or O radical, "ring structure" has the meanings given for ZG in the case of formula I, $Sp^1$ and $Sp^2$ have the meanings given for $S^{11}$ and $S^{12}$ respectively in the case of formula I, and preferably n denotes 2 or 3, L denotes a single bond, "ring structure" denotes an aromatic or aliphatic radical, $Sp^1$ and $Sp^2$ denote a single bond or an alkylene radical having 1 to 8 C atoms and $R^1$ denotes benzyl or an O radical.

For the present invention, the following definitions apply in connection with the specification of the constituents of the compositions, unless indicated otherwise in individual cases:

"comprise": has its conventional meaning; however, the concentration of the constituents in question in the composition is preferably 5% or more, particularly preferably 10% or more, very particularly preferably 20% or more, and in relation to the concentration of an individual compound relative to the medium as a whole, the term "comprise" means: the concentration of the compound in question is preferably 1% or more, particularly preferably 2% or more, very particularly preferably 4% or more.

"predominantly consist of": the concentration of the constituents in question in the composition is preferably 50% or more, particularly preferably 55% or more and very particularly preferably 60% or more, "essentially consist of": the concentration of the constituents in question in the composition is preferably 80% or more, particularly preferably 90% or more and very particularly preferably 95% or more, and "virtually completely consist of": the concentration of the constituents in question in the composition is preferably 98% or more, particularly preferably 99% or more and very particularly preferably 100.0%.

This applies both to the media as compositions with their constituents, which can be components and compounds, and also to the components with their constituents, the compounds.

For the present invention, "≤" means less than or equal to, preferably less than, and "≥" means greater than or equal to, preferably greater than.

For the present invention,

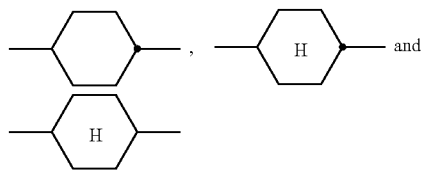

denote trans-1,4-cyclohexylene, and

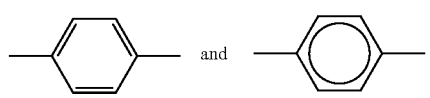

denote 1,4-phenylene.

For the present invention, the expression "dielectrically positive compounds" means compounds having a Δε of >1.5, the expression "dielectrically neutral compounds" means those where −1.5≤Δε≤1.5 and the expression "dielectrically negative compounds" means those where Δε<−1.5. The dielectric anisotropy of the compounds is determined here by dissolving 10% of the compounds in a liquid-crystalline host and determining the capacitance of the resultant mixture in each case in at least one test cell having a cell thickness of 20 μm with homeotropic and with homogeneous surface alignment at 1 kHz. The measurement voltage is typically 0.5 V to 1.0 V, but is always lower than the capacitive threshold of the respective liquid-crystal mixture investigated.

The host mixture used for dielectrically positive and dielectrically neutral compounds is ZLI-4792 and that used for dielectrically negative compounds is ZLI-2857, both from Merck KGaA, Germany. The values for the respective compounds to be investigated are obtained from the change in the dielectric constant of the host mixture after addition of the compound to be investigated and extrapolation to 100% of the compound employed. The compound to be investigated is dissolved in the host mixture in an amount of 10%. If the solubility of the substance is too low for this purpose, the concentration is halved in steps until the investigation can be carried out at the desired temperature.

The liquid-crystal media according to the invention may, if necessary, also comprise further additives, such as, for example, stabilisers and/or pleo-chroic dyes and/or chiral dopants in the usual amounts. The amount of these additives employed is preferably in total 0% or more to 10% or less, based on the amount of the entire mixture, particularly preferably 0.1% or more to 6% or less. The concentration of the individual compounds employed is preferably 0.1% or more to 3% or less. The concentration of these and similar additives is generally not taken into account when specifying the concentrations and concentration ranges of the liquid-crystal compounds in the liquid-crystal media.

In a preferred embodiment, the liquid-crystal media according to the invention comprise a polymer precursor which comprises one or more reactive compounds, preferably reactive mesogens, and, if necessary, also further additives, such as, for example, polymerisation initiators and/or polymerisation moderators, in the usual amounts. The amount of these additives employed is in total 0% or more to 10% or less, based on the amount of the entire mixture, preferably 0.1% or more to 2% or less. The concentration of these and similar additives is not taken into account when specifying the concentrations and concentration ranges of the liquid-crystal compounds in the liquid-crystal media.

The compositions consist of a plurality of compounds, preferably 3 or more to 30 or fewer, particularly preferably 6 or more to 20 or fewer and very particularly preferably 10 or more to 16 or fewer compounds, which are mixed in a conventional manner. In general, the desired amount of the components used in lesser amount is dissolved in the components making up the principal constituent of the mixture. This is advantageously carried out at elevated temperature. If the selected temperature is above the clearing point of the principal constituent, completion of the dissolution operation is particularly easy to observe. However, it is also possible to prepare the liquid-crystal mixtures in other conventional ways, for example using pre-mixes or from a so-called "multibottle system".

The mixtures according to the invention exhibit very broad nematic phase ranges having clearing points of 65° C. or more, very favourable values for the capacitive threshold, relatively high values for the holding ratio and at the same time very good low-temperature stabilities at −30° C. and −40° C. Furthermore, the mixtures according to the invention are distinguished by low rotational viscosities $\gamma_1$.

It goes without saying to the person skilled in the art that the media according to the invention for use in VA, IPS, FFS or PALC displays may also comprise compounds in which, for example, H, N, O, Cl, F have been replaced by the corresponding isotopes.

The structure of the liquid-crystal displays according to the invention corresponds to the usual geometry, as described, for example, in EP-A 0 240 379.

The liquid-crystal phases according to the invention can be modified by means of suitable additives in such a way that they can be employed in any type of, for example, ECB, VAN, IPS, GH or ASM-VA LCD display that has been disclosed to date.

Table E below indicates possible dopants which can be added to the mixtures according to the invention. If the mixtures comprise one or more dopants, it is (they are) employed in amounts of 0.01 to 4%, preferably 0.1 to 1.0%.

Stabilisers which can be added, for example, to the mixtures according to the invention, preferably in amounts of 0.01 to 6%, in particular 0.1 to 3%, are shown below in Table F.

For the purposes of the present invention, all concentrations are, unless explicitly noted otherwise, indicated in percent by weight and relate to the corresponding mixture or mixture component, unless explicitly indicated otherwise.

All temperature values indicated in the present application, such as, for example, the melting point T(C,N), the smectic (S) to nematic (N) phase transition T(S,N) and the clearing point T(N,I), are indicated in degrees Celsius (° C.) and all temperature differences are correspondingly indicated in differential degrees (° or degrees), unless explicitly indicated otherwise.

For the present invention, the term "threshold voltage" relates to the capacitive threshold ($V_0$), also known as the Freedericks threshold, unless explicitly indicated otherwise.

All physical properties are and have been determined in accordance with "Merck Liquid Crystals, Physical Properties of Liquid Crystals", status November 1997, Merck KGaA, Germany, and apply for a temperature of 20° C., and $\Delta n$ is determined at 589 nm and $\Delta \varepsilon$ at 1 kHz, unless explicitly indicated otherwise in each case.

The electro-optical properties, for example the threshold voltage ($V_0$) (capacitive measurement), are, as is the switching behaviour, determined in test cells produced at Merck Japan. The measurement cells have soda-lime glass substrates and are constructed in an ECB or VA configuration with polyimide alignment layers (SE-1211 with diluent **26 (mixing ratio 1:1), both from Nissan Chemicals, Japan), which have been rubbed perpendicularly to one another and effect homeotropic alignment of the liquid crystals. The surface area of the transparent, virtually square ITO electrodes is 1 cm$^2$.

Unless indicated otherwise, a chiral dopant is not added to the liquid-crystal mixtures used, but the latter are also particularly suitable for applications in which doping of this type is necessary.

The VHR is determined in test cells produced at Merck Japan. The measurement cells have soda-lime glass substrates and are constructed with polyimide alignment layers (for example AL-3046 from Japan Synthetic Rubber, Japan, unless indicated otherwise) with a layer thickness of 50 nm or with the alignment layers described in the examples, which have been rubbed perpendicularly to one another. The layer thickness is a uniform 6.0 μm. The surface area of the transparent ITO electrodes is 1 cm$^2$.

The VHR is determined at 20° C. (VHR$_{20}$) and after 5 minutes in an oven at 100° C. (VHR$_{100}$) in a commercially available instrument from Autronic Melchers, Germany. The voltage used has a frequency of 60 Hz, or the conditions indicated in the examples.

The accuracy of the VHR measurement values depends on the respective value of the VHR. The accuracy decreases with decreasing values. The deviations generally observed in the case of values in the various magnitude ranges are compiled in their order of magnitude in the following table.

| VHR range VHR values | | Deviation (relative) $\Delta_G$VHR/VHR/% |
|---|---|---|
| from | to | Approx. |
| 99.6% | 100% | +/−0.1 |
| 99.0% | 99.6% | +/−0.2 |
| 98% | 99% | +/−0.3 |
| 95% | 98% | +/−0.5 |
| 90% | 95% | +/−1 |
| 80% | 90% | +/−2 |
| 60% | 80% | +/−4 |
| 40% | 60% | +/−8 |
| 20% | 40% | +/−10 |
| 10% | 20% | +/−20 |

The stability to UV irradiation is investigated in a "Suntest CPS", a commercial instrument from Heraeus, Germany. The sealed test cells are irradiated for 2.0 hours without additional heating. The irradiation power in the wavelength range from 300 nm to 800 nm is 765 W/m$^2$ V, or the conditions indicated in the examples. A UV "cut-off" filter having an edge wavelength of 310 nm is used in order to simulate the so-called window glass mode. In each series of experiments, at least four test cells are investigated for each condition, and the respective results are indicated as averages of the corresponding individual measurements.

The decrease in the voltage holding ratio (ΔVHR) usually caused by the exposure, for example by UV irradiation by LCD backlighting, is determined in accordance with the following equation (1):

$$\Delta VHR(t) = VHR(t) - VHR(t=0) \tag{1}$$

The relative stability ($S_{rel}$) of an LC mixture to a load for a time t is determined in accordance with the following equation, Equation (2):

$$S_{rel}(t) = \frac{VHRref(t=0) - VHRref(t)}{VHR(t=0) - VHR(t)}, \tag{2}$$

where "ref" stands for the corresponding unstabilised mixture.

A further characteristic quantity which, besides the VHR, can characterise the conductivity of the liquid-crystal mixtures is the ion density. High values of the ion density often result in the occurrence of display faults, such as image sticking and flickering. The ion density is preferably determined in test cells produced at Merck Japan Ltd. The test cells have substrates made from soda-lime glass and are designed with polyimide alignment layers (for example AL-3046 from Japan Synthetic Rubber, Japan, unless indicated otherwise) having a polyimide layer thickness of 40 nm. The layer thickness of the liquid-crystal mixture is a uniform 5.8 μm. The area of the circular, transparent ITO electrodes, which are additionally fitted with a guard ring, is 1 cm². The accuracy of the measurement method is about ±15%. The cells are dried overnight in an oven at 120° C. before filling with the relevant liquid-crystal mixture.

The ion density is measured using a commercially available instrument from TOYO, Japan. The measurement method is essentially a measurement method which is analogous to cyclic voltammetry, as described in M. Inoue, "Recent Measurement of Liquid Crystal Material Characteristics", Proceedings IDW 2006, LCT-7-1,647. In this method, an applied direct voltage is varied between a positive and negative maximum value in accordance with a pre-specified triangular profile. A complete run through the profile thus forms one measurement cycle. If the applied voltage is sufficiently large that the ions in the field are able to move to the respective electrode, an ion current forms due to discharge of the ions. The amount of charge transferred here is typically in the range from a few pC to a few nC. This makes highly sensitive detection necessary, which is ensured by the above-mentioned instrument. The results are depicted in a current/voltage curve. The ion current here is evident from the occurrence of a peak at voltages which are smaller than the threshold voltage of the liquid-crystal mixture. Integration of the peak area gives the value for the ion density of the mixture investigated. Four test cells are measured per mixture. The repetition frequency of the triangular voltage is 0.033 Hz, the measurement temperature is 60° C., the maximum voltage is ±3 V to ±10 V, depending on the magnitude of the dielectric anisotropy of the relevant mixture.

The rotational viscosity is determined using the rotating permanent magnet method and the flow viscosity in a modified Ubbelohde viscometer. For liquid-crystal mixtures ZLI-2293, ZLI-4792 and MLC-6608, all products from Merck KGaA, Darmstadt, Germany, the rotational viscosity values determined at 20° C. are 161 mPa·s, 133 mPa·s and 186 mPa·s respectively, and the flow viscosity values (ν) are 21 mm²·s⁻¹, 14 mm²·s⁻¹ and 27 mm²·s⁻¹ respectively.

The following symbols are used, unless explicitly indicated otherwise:

$V_0$ threshold voltage, capacitive [V] at 20° C.,
$n_e$ extraordinary refractive index measured at 20° C. and 589 nm,
$n_o$ ordinary refractive index measured at 20° C. and 589 nm,
Δn optical anisotropy measured at 20° C. and 589 nm,
$\varepsilon_\perp$ dielectric susceptibility perpendicular to the director at 20° C. and 1 kHz,
$\varepsilon_\parallel$ dielectric susceptibility parallel to the director at 20° C. and 1 kHz,
Δε dielectric anisotropy at 20° C. and 1 kHz,
cl.p. or
T(N,I) clearing point [° C.],
ν flow viscosity measured at 20° C. [mm²·s⁻¹],
$\gamma_1$ rotational viscosity measured at 20° C. [mPa·s],
$K_1$ elastic constant, "splay" deformation at 20° C. [pN],
$K_2$ elastic constant, "twist" deformation at 20° C. [pN],
$K_3$ elastic constant, "bend" deformation at 20° C. [pN], and
LTS low-temperature stability of the phase, determined in test cells,
VHR voltage holding ratio,
ΔVHR decrease in the voltage holding ratio,
$S_{rel}$ relative stability of the VHR.

The following examples explain the present invention without limiting it. However, they show the person skilled in the art preferred mixture concepts with compounds preferably to be employed and the respective concentrations thereof and combinations thereof with one another. In addition, the examples illustrate the properties and property combinations that are accessible.

For the present invention and in the following examples, the structures of the liquid-crystal compounds are indicated by means of acronyms, with the transformation into chemical formulae taking place in accordance with Tables A to C below. All radicals $C_nH_{2n+1}$, $C_mH_{2m+1}$ and $C_lH_{2l+1}$ or $C_nH_{2n}$, $C_mH_{2m}$ and $C_lH_{2l}$ are straight-chain alkyl radicals or alkylene radicals, in each case having n, m and l C atoms respectively. Table A shows the codes for the ring elements of the nuclei of the compound, Table B lists the bridging units, and Table C lists the meanings of the symbols for the left- and right-hand end groups of the molecules. The acronyms are composed of the codes for the ring elements with optional linking groups, followed by a first hyphen and the codes for the left-hand end group, and a second hyphen and the codes for the right-hand end group. Table D shows illustrative structures of compounds together with their respective abbreviations.

TABLE A

Ring elements

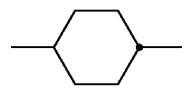

C

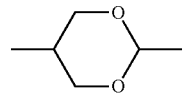

D

TABLE A-continued
| Ring elements | |
|---|---|
| 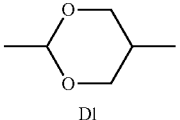 Dl | 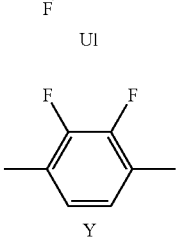 P(F,Cl)Y |
| 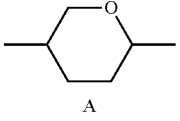 A | 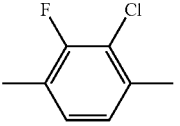 P(Cl,F)Y |
| 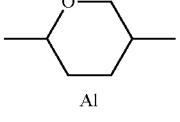 Al | 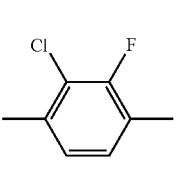 np |
| 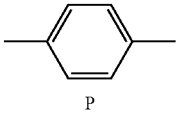 P | 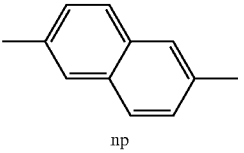 n3f |
| 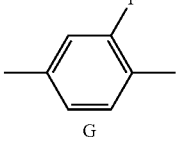 G | 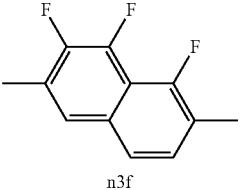 nN3fl |
| 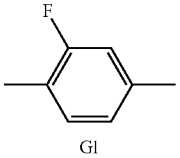 Gl | 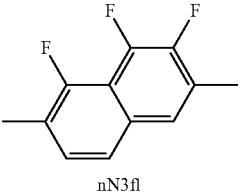 th |
| 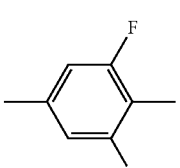 U | 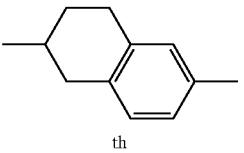 thl |
| 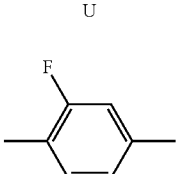 Ul | 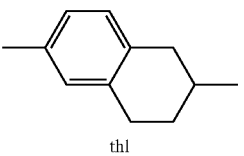 tH2f |
| 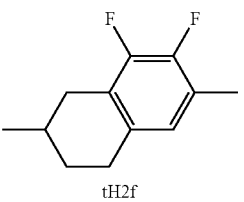 Y | |

TABLE A-continued

Ring elements

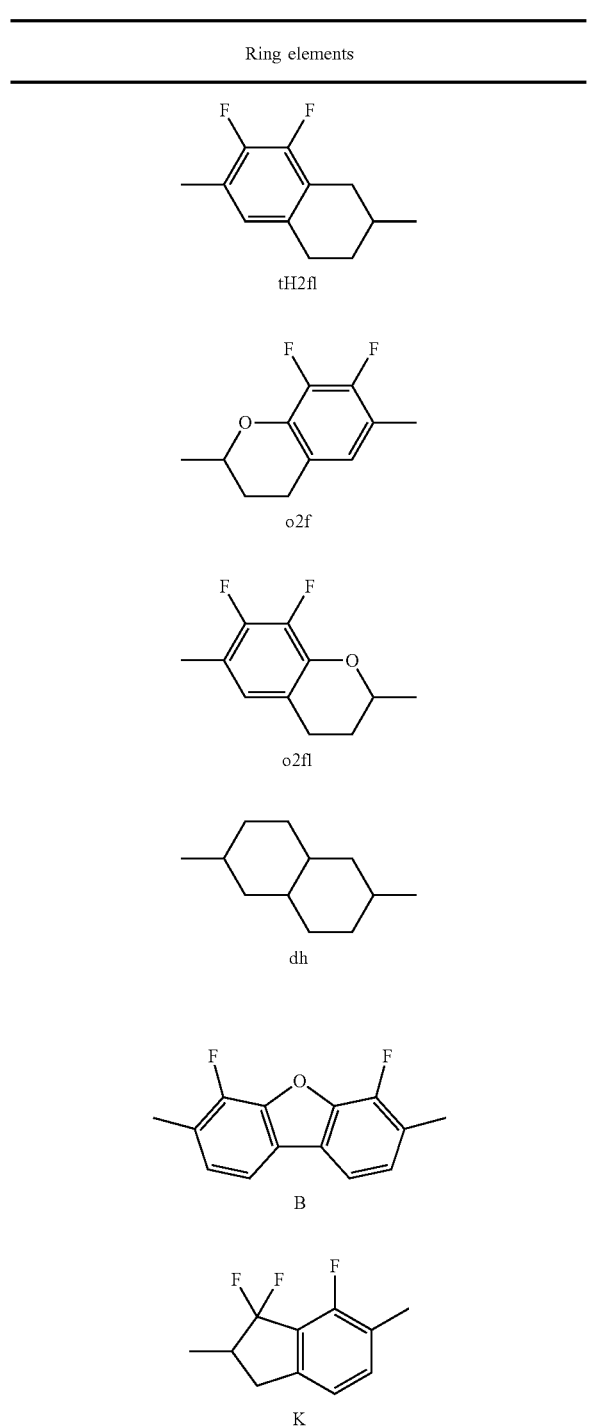

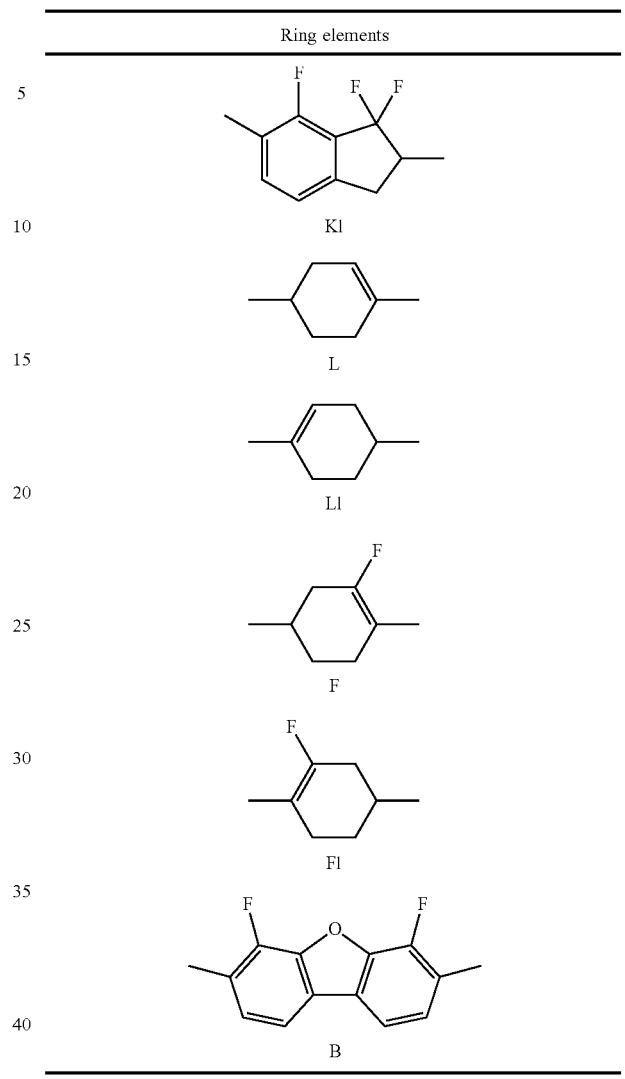

TABLE B

| | Bridging units | | |
|---|---|---|---|
| E | —CH$_2$—CH$_2$— | | |
| V | —CH=CH— | | |
| T | —C≡C— | | |
| W | —CF$_2$—CF$_2$— | | |
| B | —CF=CF— | | |
| Z | —CO—O— | ZI | —O—CO— |
| X | —CF=CH— | XI | —CH=CF— |
| O | —CH$_2$—O— | OI | —O—CH$_2$— |
| Q | —CF$_2$—O— | QI | —O—CF$_2$— |

TABLE C

| End groups | | | |
|---|---|---|---|
| On the left individually or in combination | | On the right individually or in combination | |
| -n- | C$_n$H$_{2n+1}$— | -n | —C$_n$H$_{2n+1}$ |
| -nO- | C$_n$H$_{2n+1}$—O— | -nO | —O—C$_n$H$_{2n+1}$ |
| -V- | CH$_2$=CH— | -V | —CH=CH$_2$ |
| -nV- | C$_n$H$_{2n+1}$—CH=CH— | -nV | —C$_n$H$_{2n}$—CH=CH$_2$ |
| -Vn- | CH$_2$=CH—C$_n$H$_{2n}$— | -Vn | —CH=CH—C$_n$H$_{2n+1}$ |

TABLE C-continued

| End groups | | | |
|---|---|---|---|
| -nVm- | $C_nH_{2n+1}$—CH=CH—$C_mH_{2m}$— | -nVm | —$C_nH_{2n}$—CH=CH—$C_mH_{2m+1}$ |
| -N- | N≡C— | -N | —C≡N |
| -S- | S=C=N— | -S | —N=C=S |
| -F- | F— | -F | —F |
| -CL- | Cl— | -CL | —Cl |
| -M- | $CFH_2$— | -M | —$CFH_2$ |
| -D- | $CF_2H$— | -D | —$CF_2H$ |
| -T- | $CF_3$— | -T | —$CF_3$ |
| -MO- | $CFH_2O$— | -OM | —$OCFH_2$ |
| -DO- | $CF_2HO$— | -OD | —$OCF_2H$ |
| -TO- | $CF_3O$— | -OT | —$OCF_3$ |
| -A- | H—C≡C— | -A | —C≡C—H |
| -nA- | $C_nH_{2n+1}$—C≡C— | -An | —C≡C—$C_nH_{2n+1}$ |
| -NA- | N≡C—C≡C— | -AN | —C≡C—C≡N |

| On the left only in combination | | On the right only in combination | |
|---|---|---|---|
| -...n...- | —$C_nH_{2n}$— | -...n... | —$C_nH_{2n}$— |
| -...M...- | —CFH— | -...M... | —CFH— |
| -...D...- | —$CF_2$— | -...D... | —$CF_2$— |
| -...V...- | —CH=CH— | -...V... | —CH=CH— |
| -...Z...- | —CO—O— | -...Z... | —CO—O— |
| -...ZI...- | —O—CO— | -...ZI... | —O—CO— |
| -...K...- | —CO— | -...K... | —CO— |
| -...W...- | —CF=CF— | -...W... | —CF=CF— | in which n and m are each integers, and the three dots "..." are placeholders for other abbreviations from this table.

Besides the compounds of the formula I, the mixtures according to the invention preferably comprise one or more compounds of the compounds mentioned below.

The following abbreviations are used:
(n, m and z are, independently of one another, each an integer, preferably 1 to 6)

TABLE D

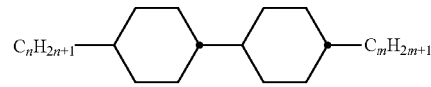

CC-n-m

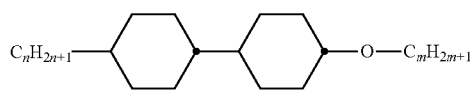

CC-n-Om

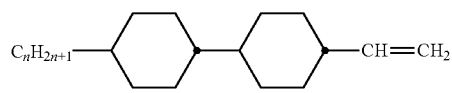

CC-n-V

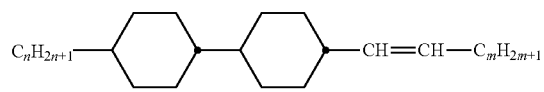

CC-n-Vm

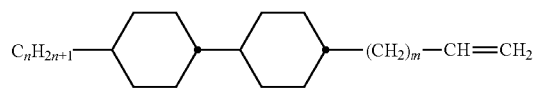

CC-n-mV

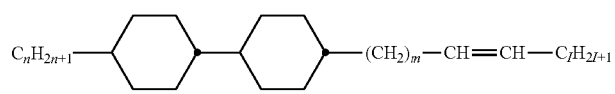

CC-n-mVl

TABLE D-continued
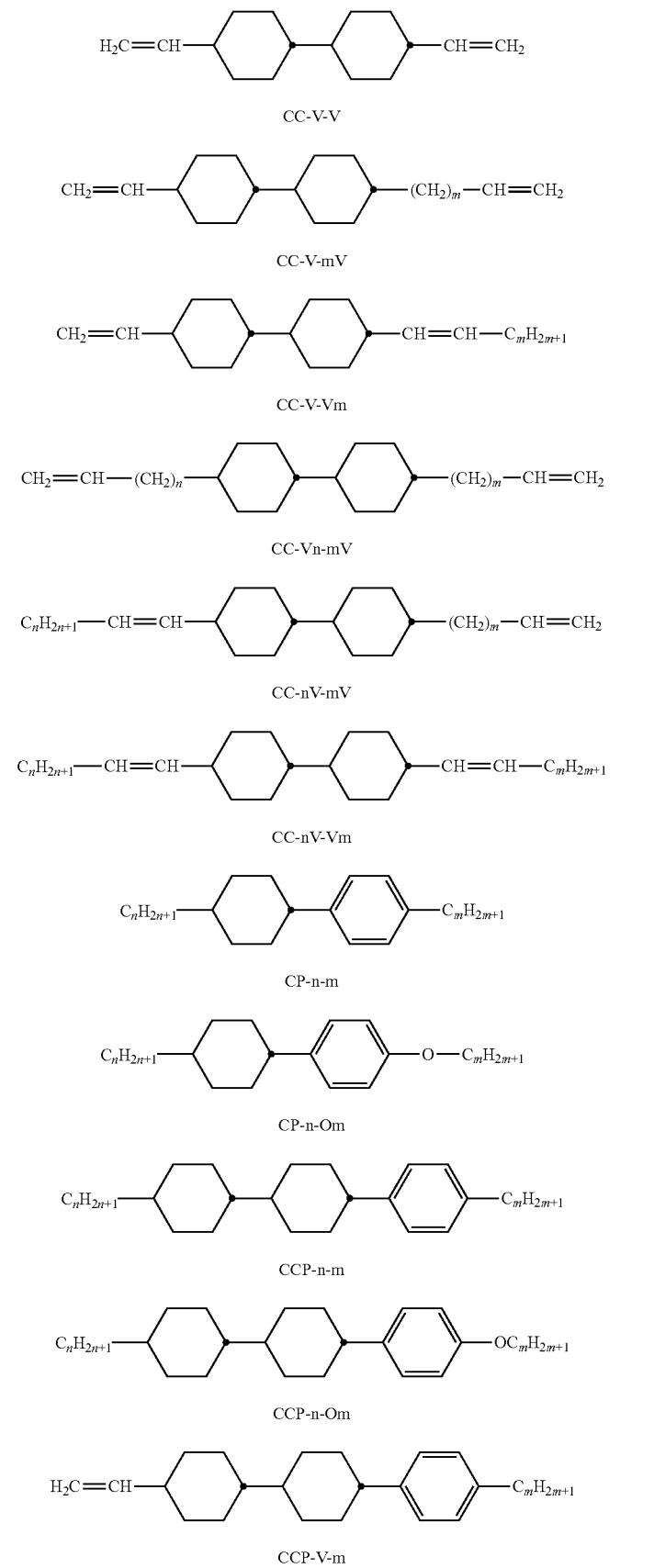

TABLE D-continued
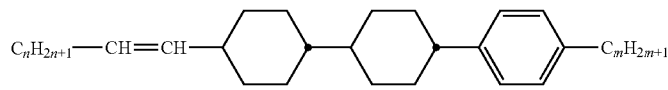
CCP-nV-m
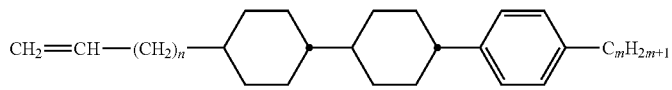
CCP-Vn-m
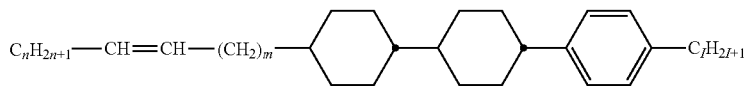
CCP-nVm-l
CPP-n-m
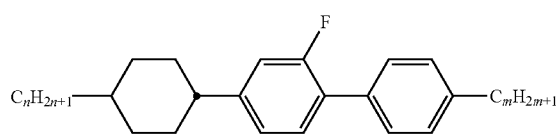
CGP-n-m
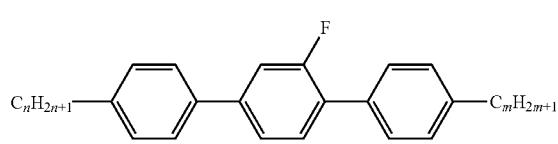
PGP-n-m
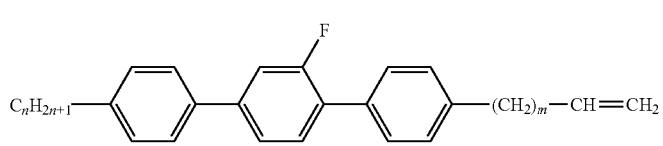
PGP-n-mV
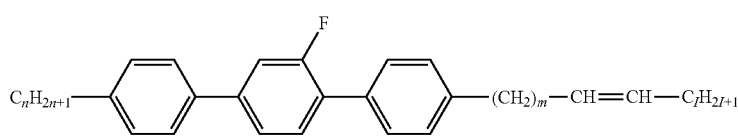
PGP-n-mVl
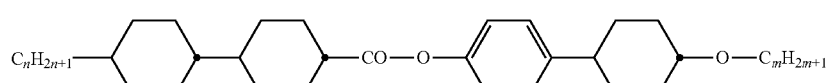
CCZPC-n-m
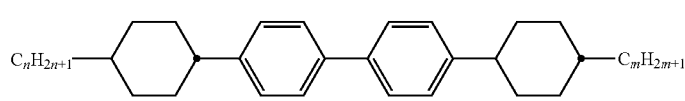
CPPC-n-m TABLE D-continued
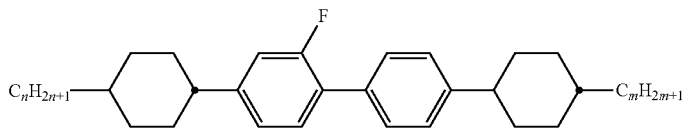
CGPC-n-m
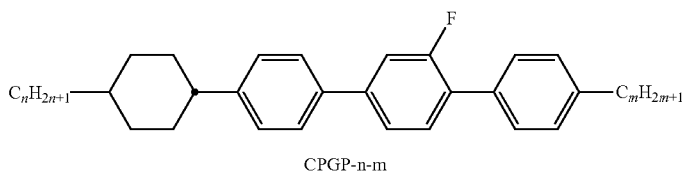
CPGP-n-m
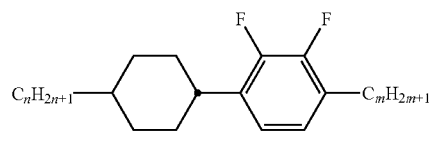
CY-n-m
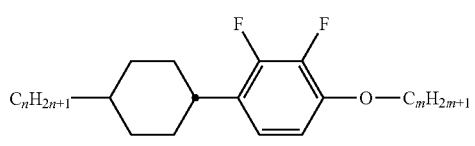
CY-n-Om
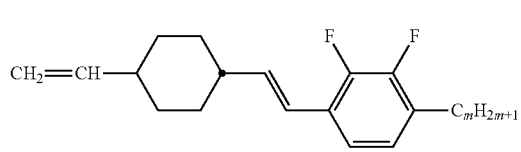
CVY-n-m
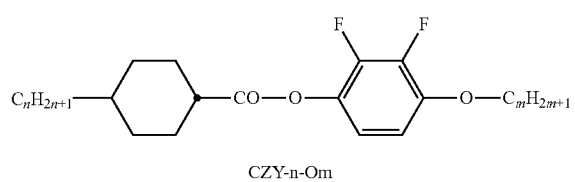
CZY-n-Om
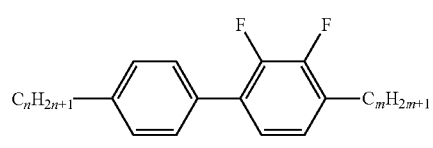
PY-n-m
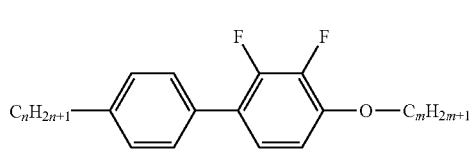
PY-n-Om
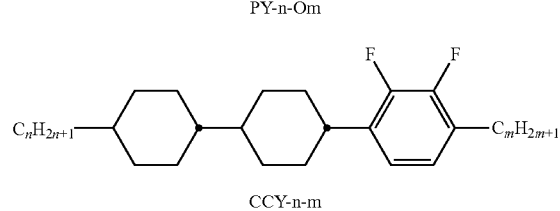
CCY-n-m TABLE D-continued
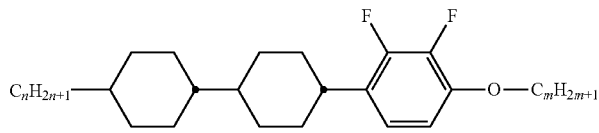
CCY-n-Om
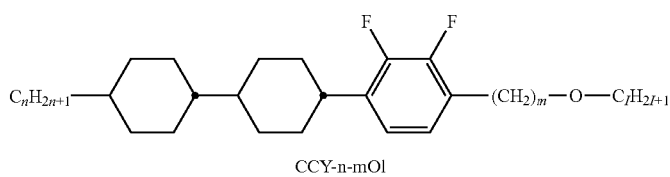
CCY-n-mOl
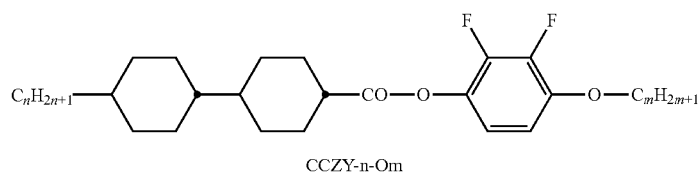
CCZY-n-Om
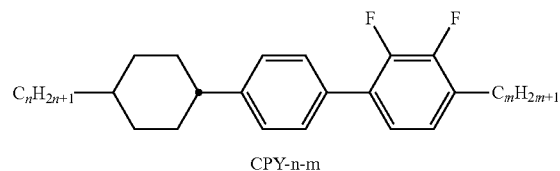
CPY-n-m
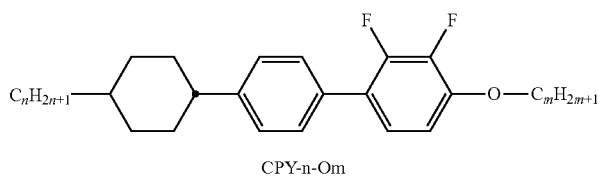
CPY-n-Om
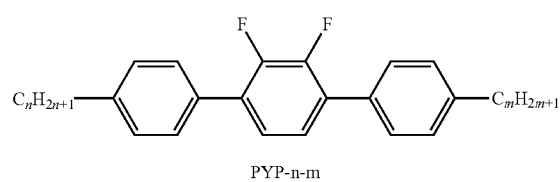
PYP-n-m
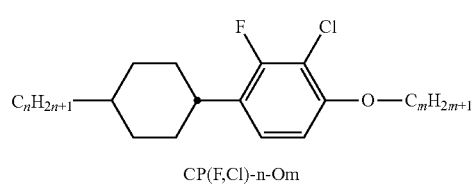
CP(F,Cl)-n-Om
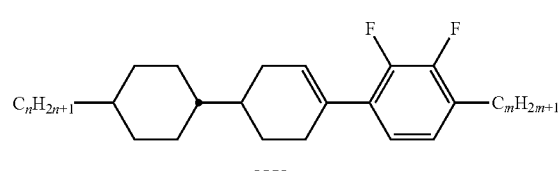
CLY-n-m
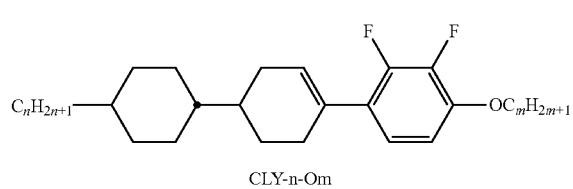
CLY-n-Om TABLE D-continued
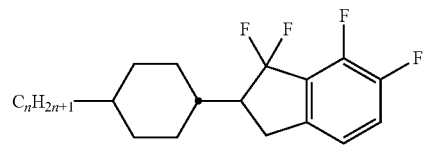
CK-n-F
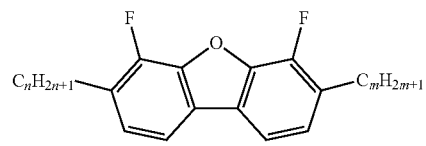
B-n-m
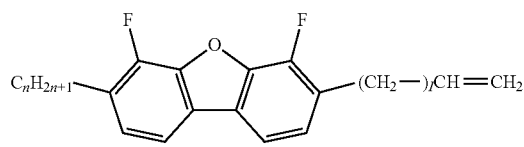
B-n-lV
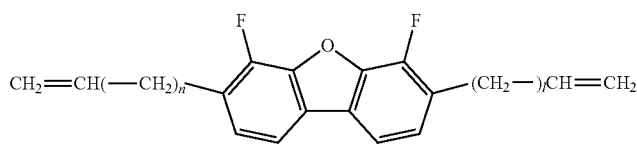
B-Vn-lV
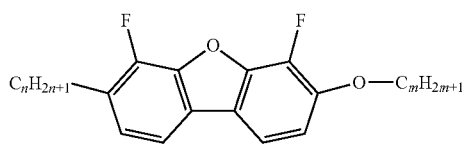
B-n-Om
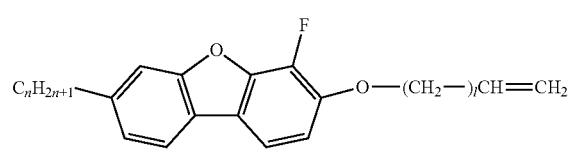
B-n-OlV
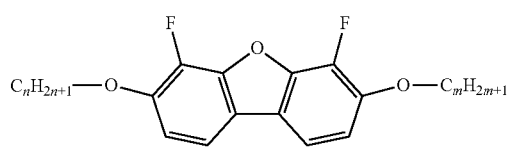
B-nO-Om
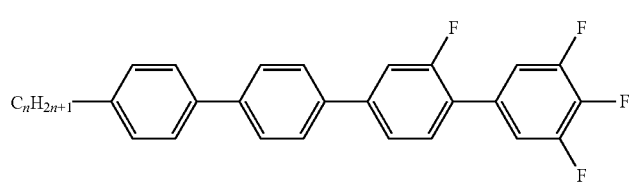
PPGU-n Table E shows chiral dopants which are preferably employed in the mixtures according to the invention.
TABLE E
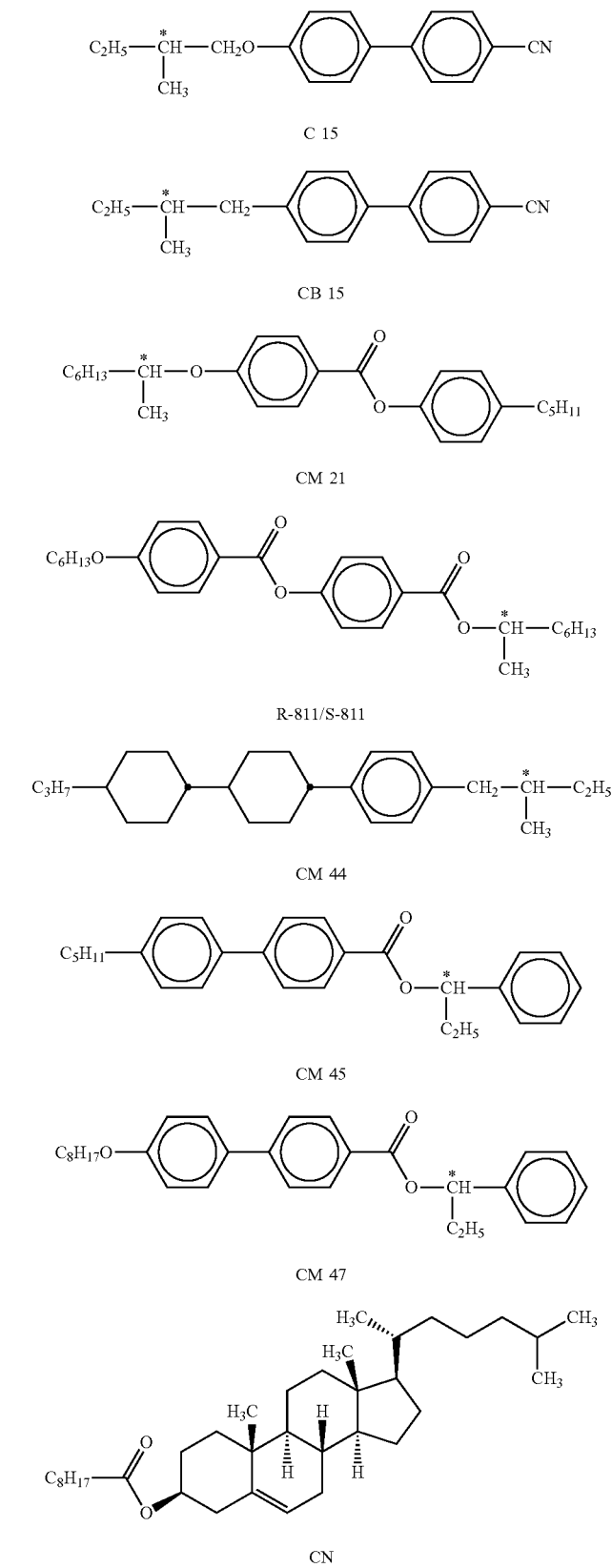

TABLE E-continued

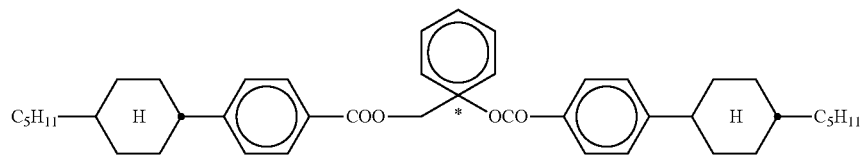

R-1011/S-1011

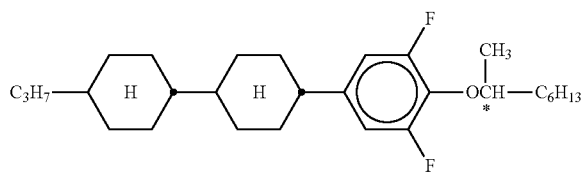

R-2011/S-2011

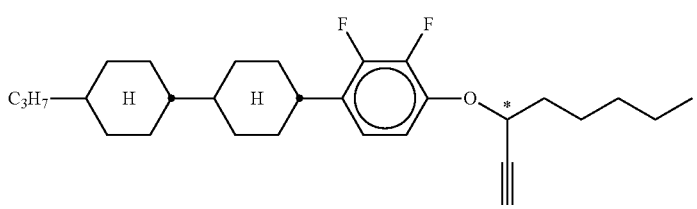

R-3011/S-3011

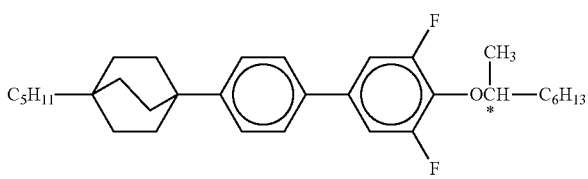

R-4011/S-4011

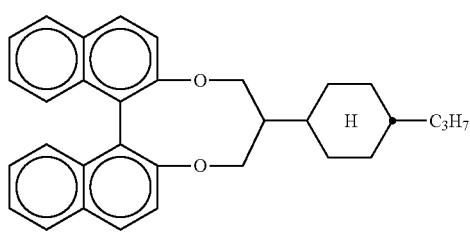

R-5011/S-5011

In a preferred embodiment of the present invention, the media according to the invention comprise one or more compounds selected from the group of the compounds from Table E.

Table F shows stabilisers which can preferably be employed in the mixtures according to the invention in addition to the compounds of the formula I. The parameter n here denotes an integer in the range from 1 to 12. In particular, the phenol derivatives shown can be employed as additional stabilisers since they act as antioxidants.

TABLE F

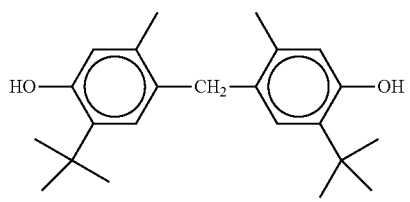

TABLE F-continued
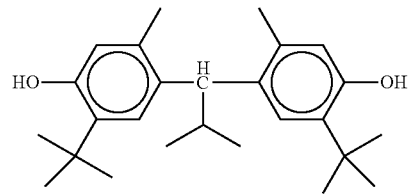
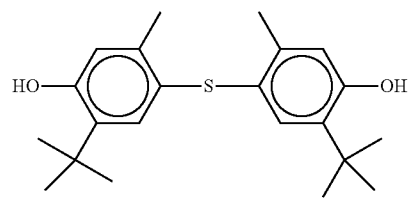
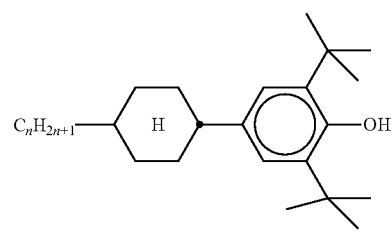
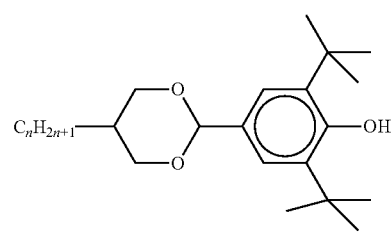
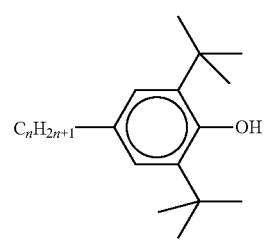
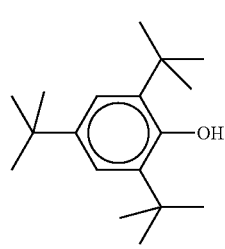
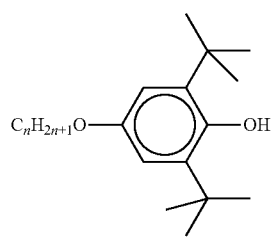

TABLE F-continued
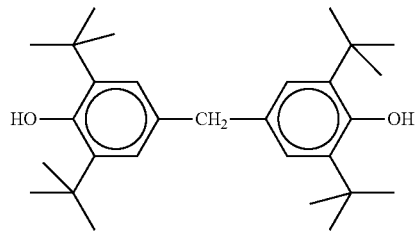
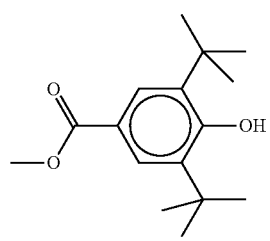
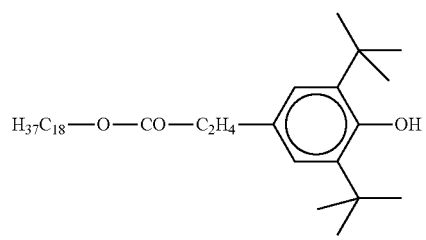
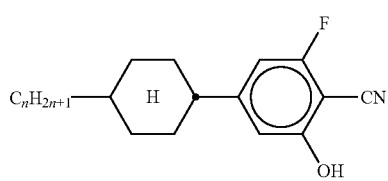
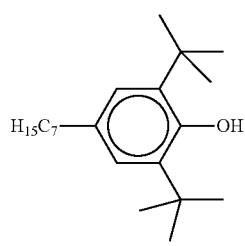
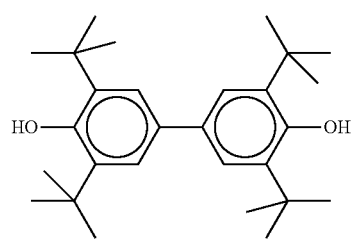

TABLE F-continued
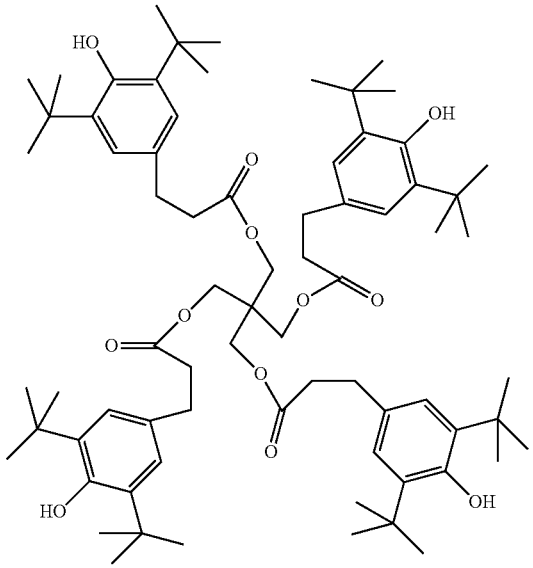 [SMILES: CC(C)(C)c1cc(CCC(=O)OCC(COC(=O)CCc2cc(C(C)(C)C)c(O)c(C(C)(C)C)c2)(COC(=O)CCc2cc(C(C)(C)C)c(O)c(C(C)(C)C)c2)COC(=O)CCc2cc(C(C)(C)C)c(O)c(C(C)(C)C)c2)cc(C(C)(C)C)c1O]
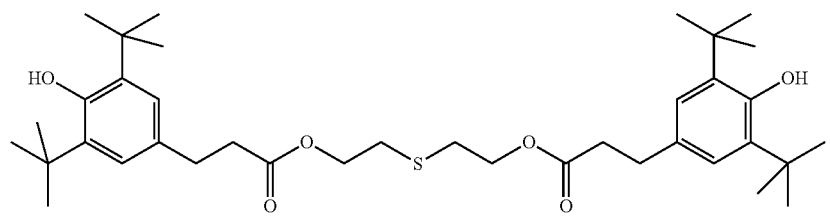 [SMILES: CC(C)(C)c1cc(CCC(=O)OCCSCCOC(=O)CCc2cc(C(C)(C)C)c(O)c(C(C)(C)C)c2)cc(C(C)(C)C)c1O]
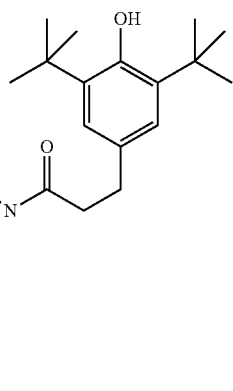
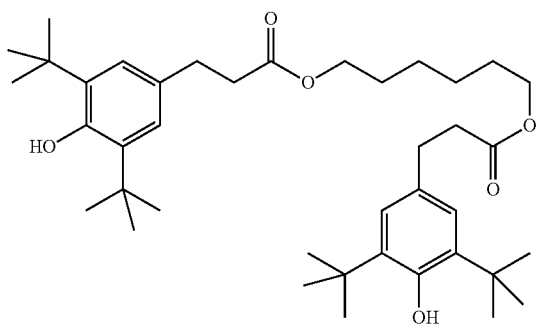 [SMILES: CC(C)(C)c1cc(CCC(=O)OCCCCCCOC(=O)CCc2cc(C(C)(C)C)c(O)c(C(C)(C)C)c2)cc(C(C)(C)C)c1O]

TABLE F-continued
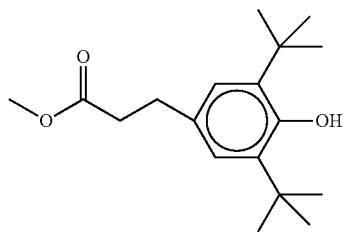
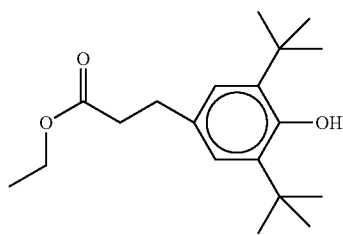
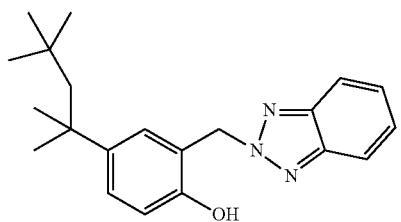 [SMILES: CC(C)(C)CC(C)(C)c1ccc(O)c(Cn2nc3ccccc3n2)c1]
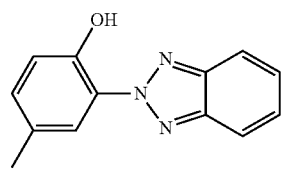 [SMILES: Cc1ccc(O)c(-n2nc3ccccc3n2)c1]
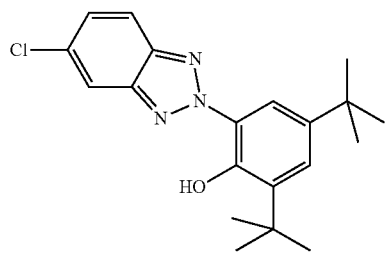 [SMILES: CC(C)(C)c1cc(-n2nc3ccc(Cl)cc3n2)c(O)c(C(C)(C)C)c1]
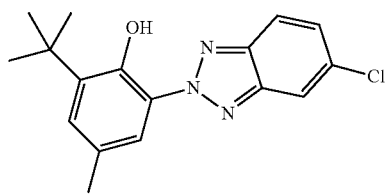 [SMILES: Cc1cc(-n2nc3ccc(Cl)cc3n2)c(O)c(C(C)(C)C)c1]

TABLE F-continued
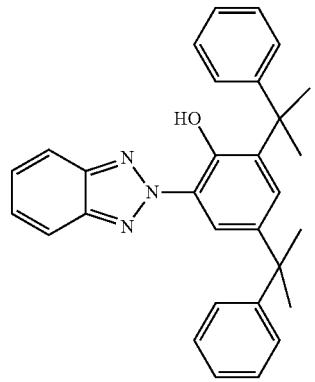 [SMILES: CC(C)(c1ccccc1)c1cc(-n2nc3ccccc3n2)c(O)c(C(C)(C)c2ccccc2)c1]
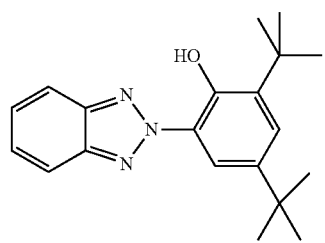 [SMILES: CC(C)(C)c1cc(-n2nc3ccccc3n2)c(O)c(C(C)(C)C)c1]
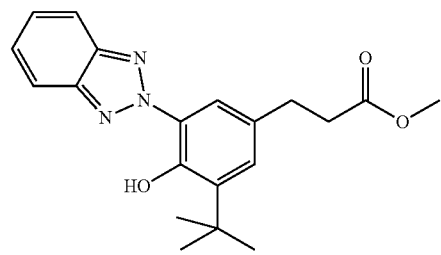 [SMILES: COC(=O)CCc1cc(-n2nc3ccccc3n2)c(O)c(C(C)(C)C)c1]
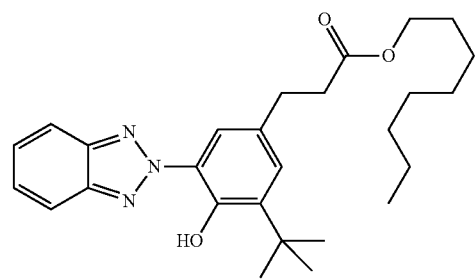 [SMILES: CCCCCCCCOC(=O)CCc1cc(-n2nc3ccccc3n2)c(O)c(C(C)(C)C)c1]

TABLE F-continued
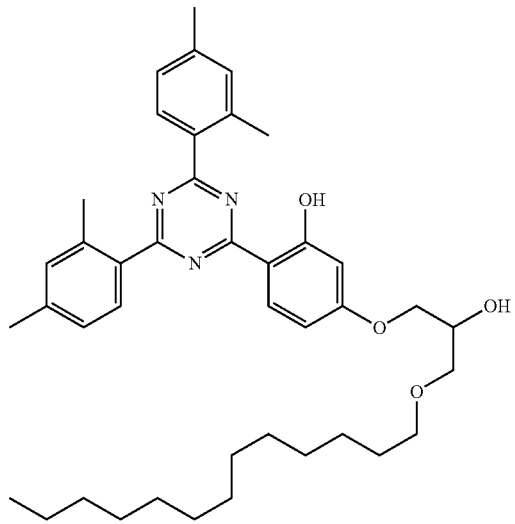 [SMILES: CCCCCCCCCCCCCOCC(O)COc1ccc(-c2nc(-c3ccc(C)cc3C)nc(-c3ccc(C)cc3C)n2)c(O)c1]
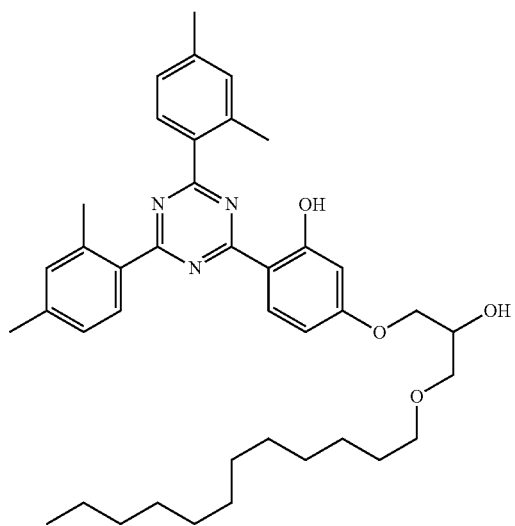 [SMILES: CCCCCCCCCCCCOCC(O)COc1ccc(-c2nc(-c3ccc(C)cc3C)nc(-c3ccc(C)cc3C)n2)c(O)c1]
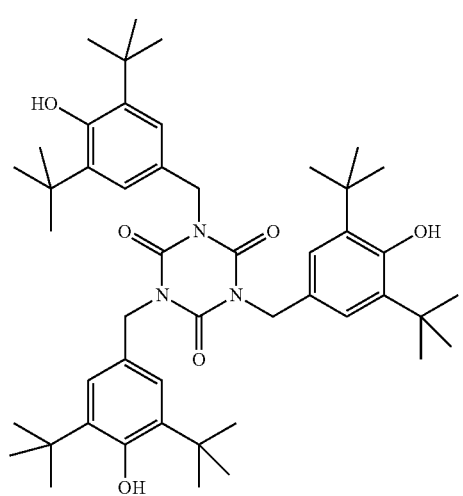 [SMILES: CC(C)(C)c1cc(Cn2c(=O)n(Cc3cc(C(C)(C)C)c(O)c(C(C)(C)C)c3)c(=O)n(Cc3cc(C(C)(C)C)c(O)c(C(C)(C)C)c3)c2=O)cc(C(C)(C)C)c1O]

TABLE F-continued

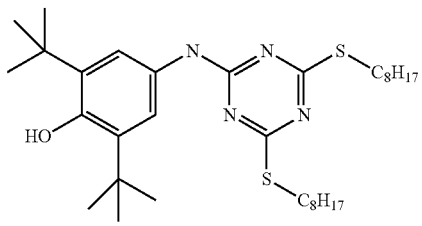

In a preferred embodiment of the present invention, the media according to the invention comprise one or more compounds selected from the group of the compounds from Table F, in particular one or more compounds selected from the group of the compounds of the two formulae

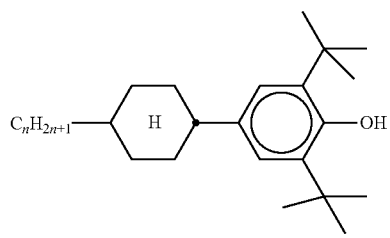

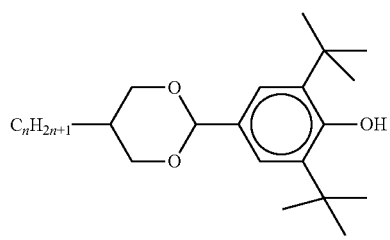

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 10 2017 000 812.4, filed Jan. 30, 2017, are incorporated by reference herein.

EXAMPLES

The following examples explain the present invention without restricting it in any way. However, the physical properties make it clear to the person skilled in the art what properties can be achieved and in what ranges they can be modified. In particular, the combination of the various properties which can preferably be achieved is thus well defined for the person skilled in the art.

SUBSTANCE EXAMPLES

The following substances are preferred substances of the formula I in accordance with the present application or substances of the formula I preferably to be employed in accordance with the present application.

1

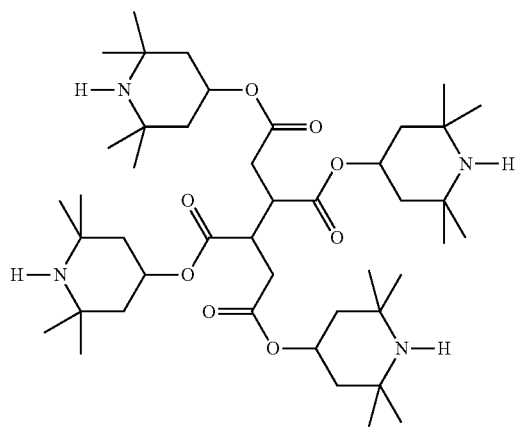

-continued
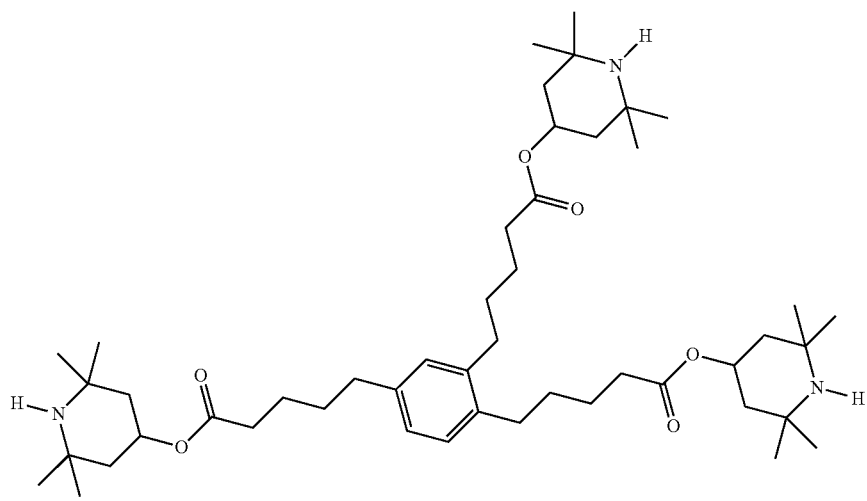
2
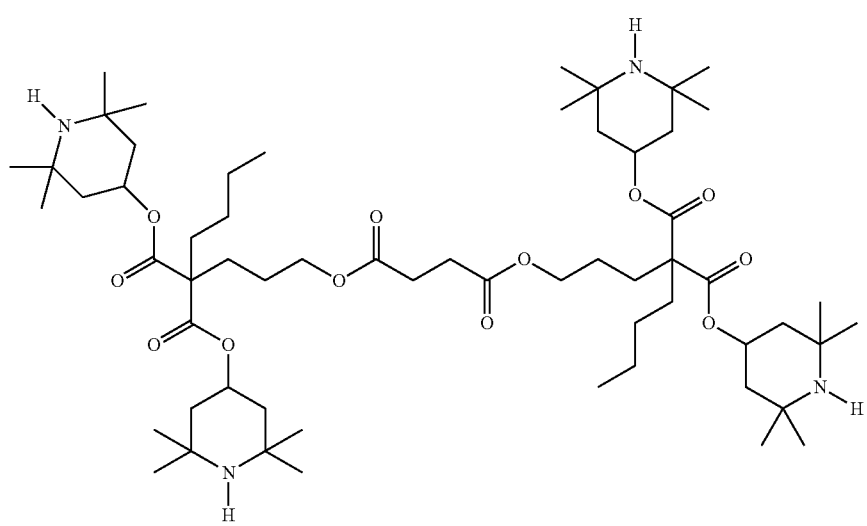
3

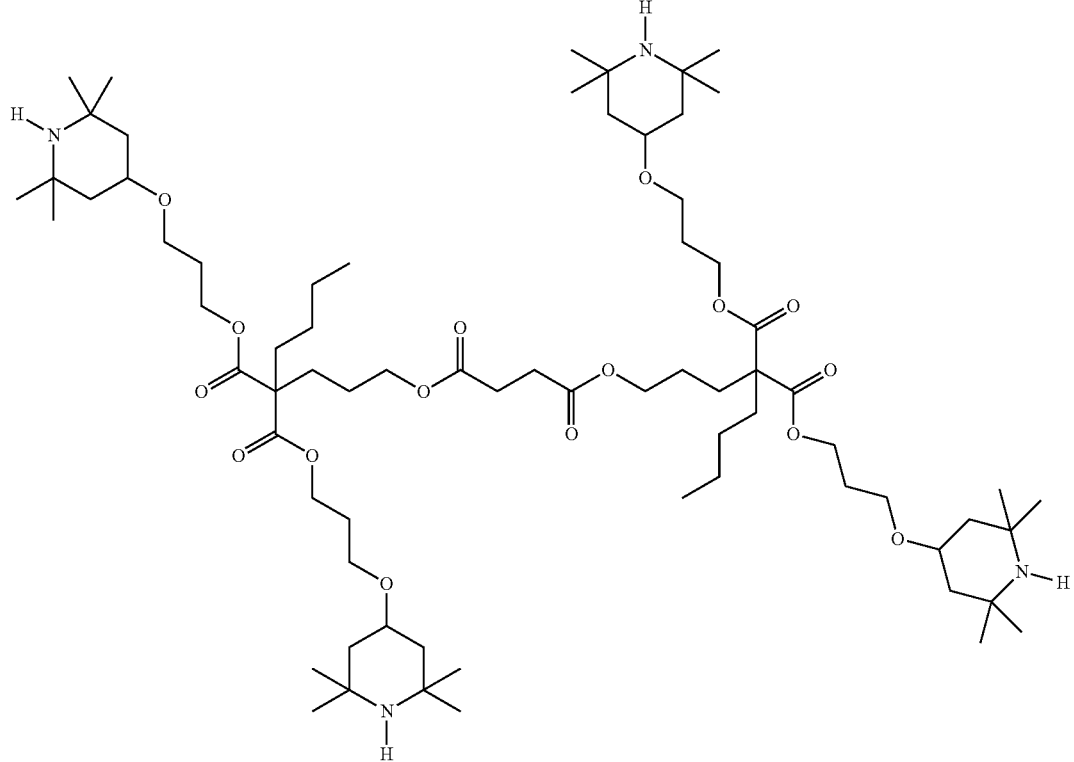
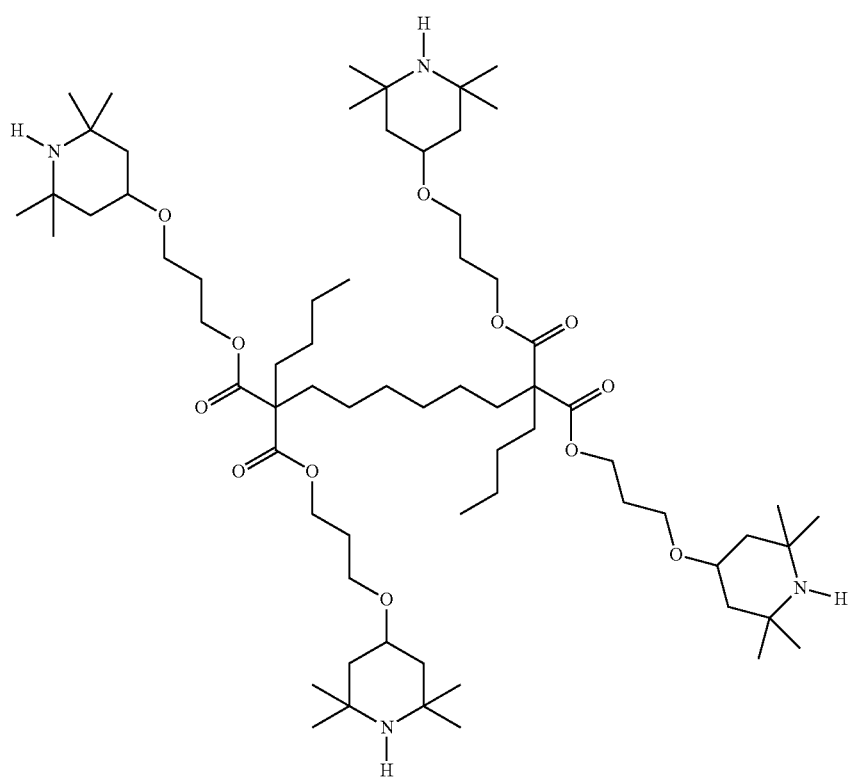

-continued
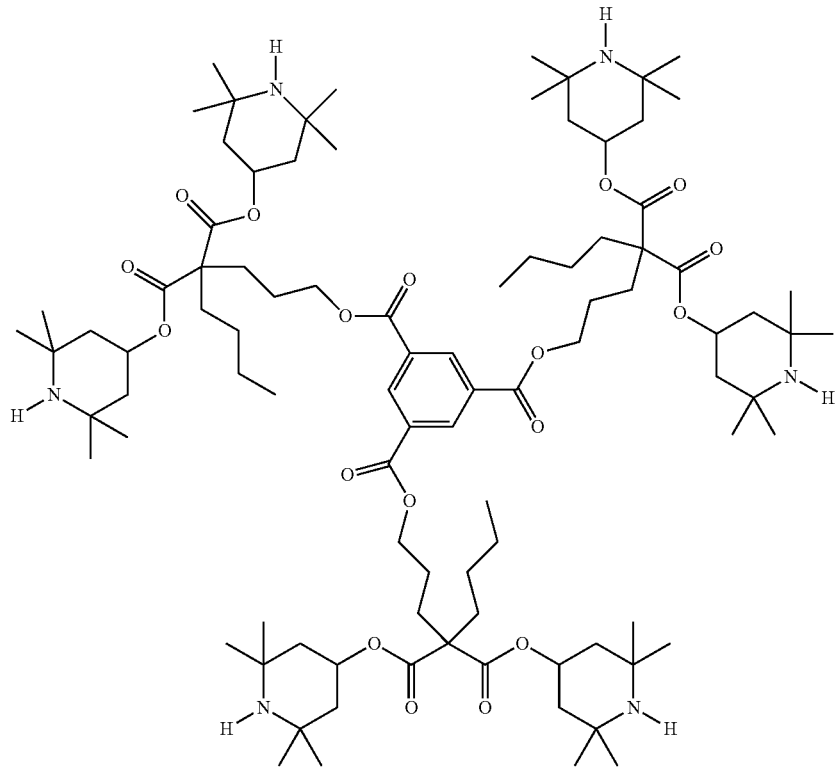
6
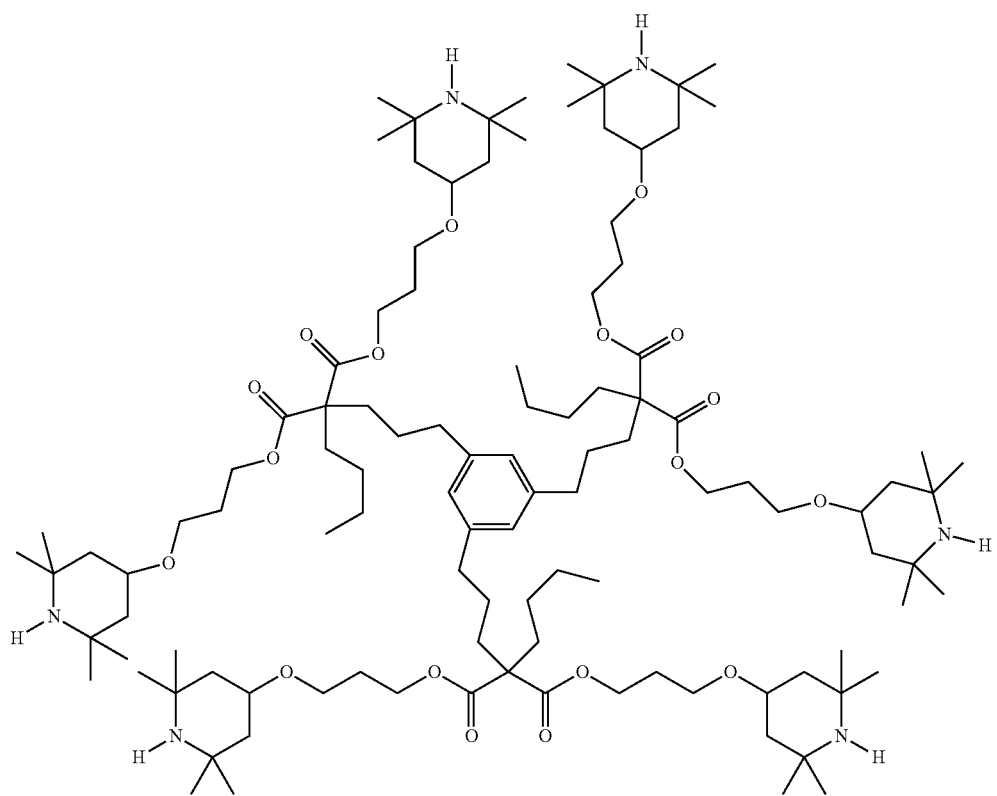
7

-continued
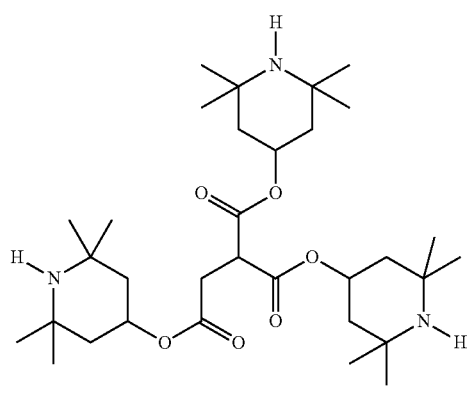
8
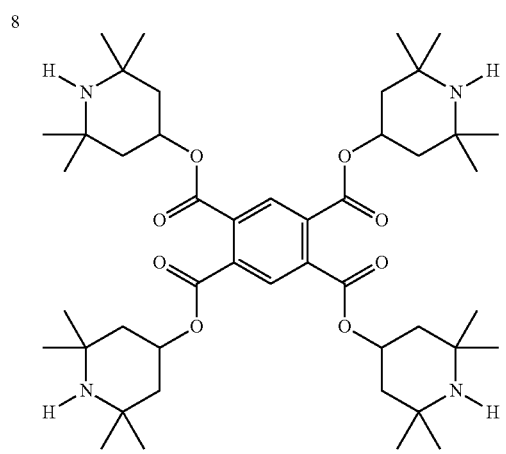
9
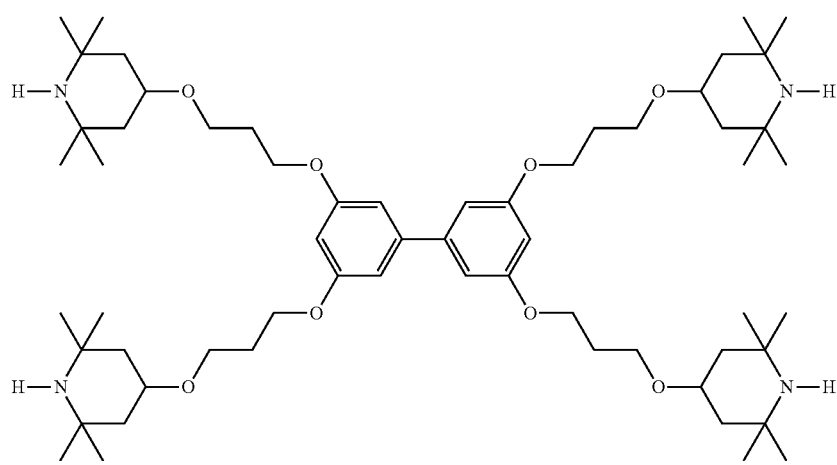
10
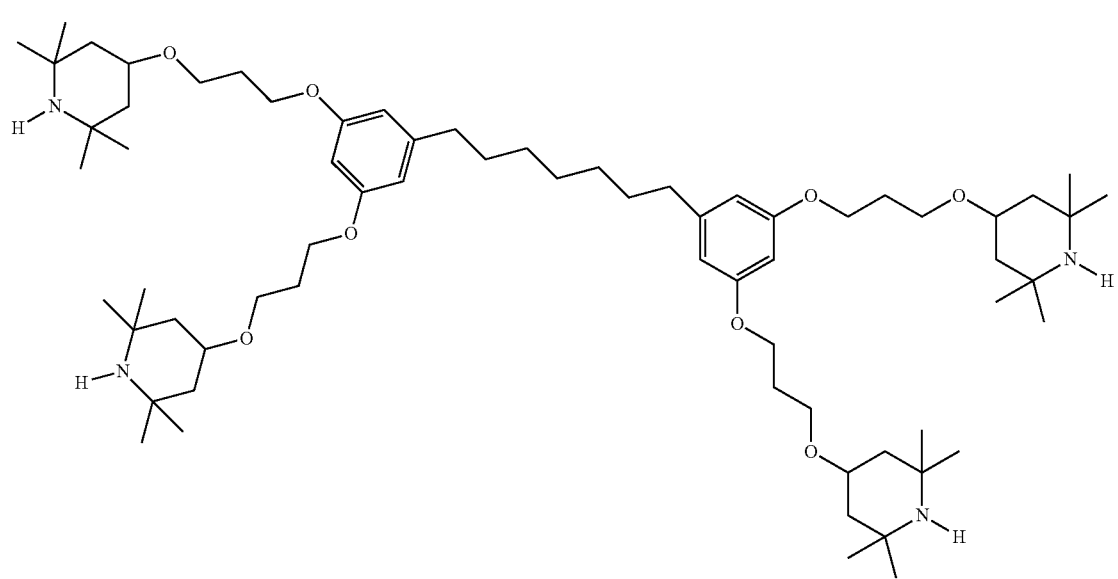
11

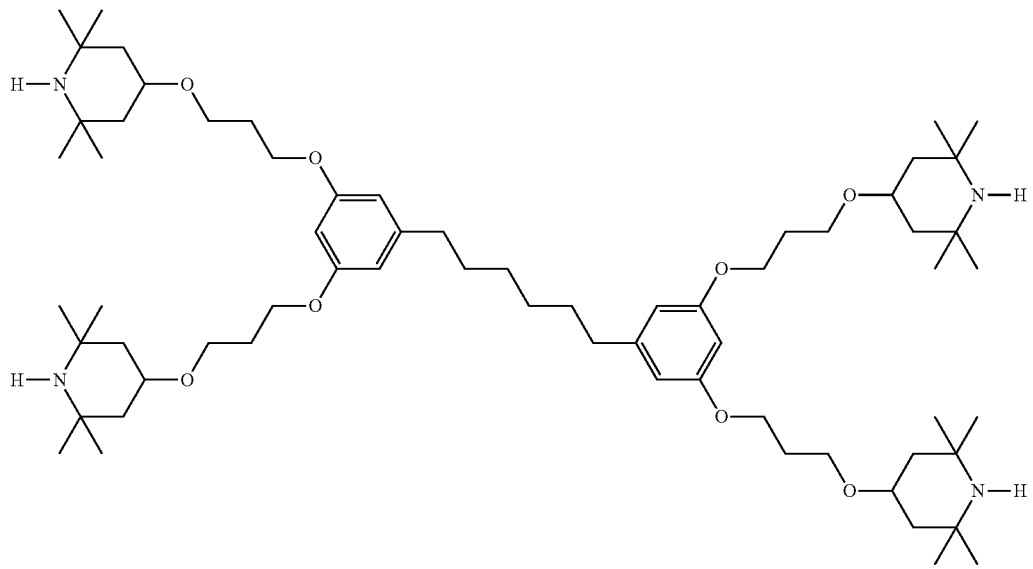

12

The following examples explain the present invention without limiting it in any way. However, the physical properties make it clear to the person skilled in the art which properties are to be achieved and in what ranges they can be modified. In particular, the combination of the various properties which can preferably be achieved is thus well defined for the person skilled in the art.

Synthesis Example 1

Synthesis of bis(2,2,6,6-tetramethylpiperidin-4-yl) 2-{3-[2,5-bis({4-butyl-5-[(2,2,6,6-tetramethylpiperidin-4-yl)oxy]-4-{[(2,2,6,6-tetramethylpiperidin-4-yl)oxy]carbonyl}-5-oxopentyl})phenyl]propyl}-2-butylpropanedioate 1

Substance Example 1

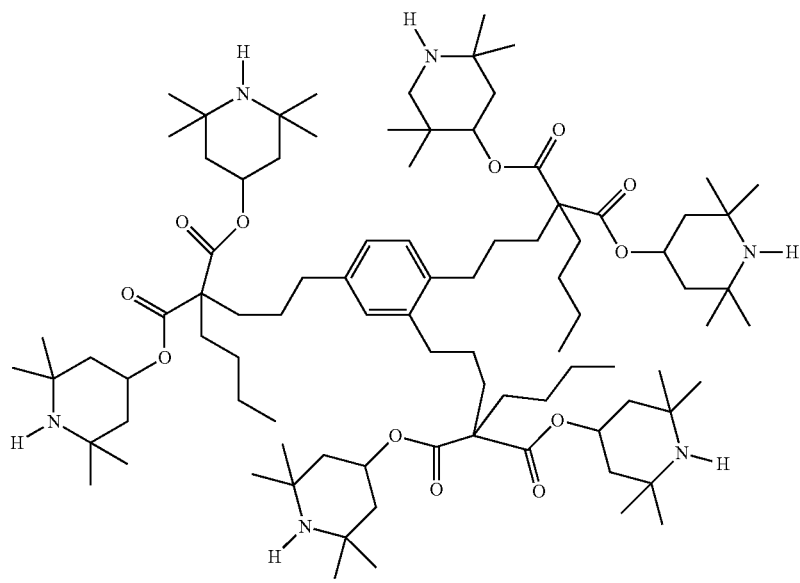

1

Step 1.1: Synthesis of 3-[3,4-bis(3-hydroxypropyl)phenyl]propan-1-ol A

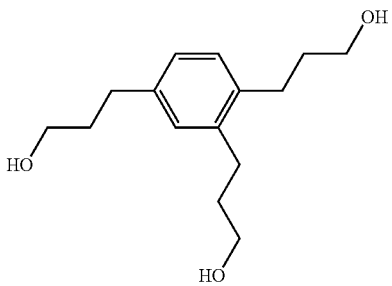

A 51.34 g (484.0 mmol) of anhydrous sodium carbonate are dissolved in 171.7 ml of water. A solution of 25.0 g (79.0 mmol) of 1,2,4-tribromo-benzene and 67.70 g (476.0 mmol) of 2-butoxy-1,2-oxaborolane in 965.2 ml of tetrahydrofuran (THF) is added, 1.65 ml (11.9 mmol) of triethylamine are added, and the mixture is stirred and degassed for 30 min. using a stream of argon. 1.40 g (7.49 mmol) of palladium(II) chloride (59% of palladium, anhydrous) and 1.85 g (3.97 mmol) of 2-dicyclohexylphoshino-2',6'-di-isopropoxy-1,1'-biphenyl are added, and the reaction mixture is stirred under reflux for 18 hours. The reaction mixture is allowed to cool to room temperature (RT), water and methyl tertiary-butyl ether (MTBE) are added, and the phases are separated. The water phase is extracted with MTBE, and the combined organic phases are washed with saturated NaCl solution, dried over sodium sulfate, filtered and evaporated in vacuo. The product is obtained as a yellowish oil and is filtered through silica gel with a mixture of ethyl acetate (EA) and methanol (9:1). The product fractions are combined and evaporated in vacuo, giving the reaction product as a pale-yellow oil. The product is characterised by means of NMR spectroscopy.

$^1$H NMR (500 MHz, DMSO-d6)

δ=1.66 (m$_c$, 6H, CH$_2$), 2.42-2.69 (m$_{(superimposed\ with\ DMSO)}$, 6H, CH$_2$,), 3.36-3.49 (m, 6H, CH$_2$), 4.44 (t, J=5.15 Hz, 1H), 4.48 (m$_c$, 2H), 6.92 (dd, J=1.7, 7.72 Hz, 1H), 6.95 (d, J=1.53 Hz, 1H), 7.03 (d, J=7.7 Hz, 1H).

Step 1.2: Synthesis of 1,2,4-tris(3-iodopropyl)benzene B

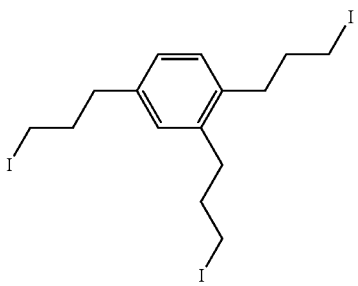

B 30.2 ml (138 mmol) of triphenylphosphine are dissolved in 513 ml of acetonitrile, and a solution of 34.92 g (138.0 mmol) of iodine in 513 ml of acetonitrile is added dropwise with gentle cooling. An orange suspension forms during this addition. When the addition is complete, the mixture is stirred for a further 10 min. 13.3 g (197 mmol) of imidazole are added, and a solution of 10.0 g (39.3 mmol) of triol A in 100 ml of acetonitrile is subsequently added dropwise (a clear, yellow solution forms during this addition). The reaction solution is stirred at RT for 3 hours (h) and carefully poured into a cold sodium thiosulfate solution (decolouration occurs), and heptane is added. After washing by stirring, the phases are separated, the water phase is extracted with heptane, and the combined organic phases are washed with water, dried over sodium sulfate, filtered and evaporated in vacuo. The crude product is filtered through silica gel with heptane (H) and ethyl acetate (8:2), and evaporation of the product fractions gives the product as a colourless oil. The product is characterised by means of mass spectrometry.

MS (EI)=582.0

Step 1.3: Synthesis of 2-butylpropanedioyl Dichloride C

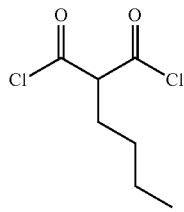

C 76.00 g (474.5 mmol) of 2-butylmalonic acid are initially introduced in the reaction apparatus and warmed to 40° C. 90.00 ml (1.240 mol) of thionyl chloride are then added dropwise over the course of about 30 min. (care, evolution of gas), and the mixture is stirred at room temperature (RT) for a further 5 hours (h). The evolution of gas decreases significantly within this time span. The reaction solution is then stirred at 50° C. for 18 h and subsequently at 70° C. for 5 h. On each increase in temperature, slight evolution of gas re-occurs. The reaction mixture is then cooled to room temperature and taken up in 300 ml of dry toluene, and excess thionyl chloride is separated off by distillation together with the toluene (8 mbar and RT to max. bath temperature of 80° C.), giving the crude product as a brownish liquid, which is employed directly in the next synthesis step.

Step 1.4: Synthesis of bis(1-oxyl-2,2,6,6-tetramethylpiperidin-4-yl) 2-butylpropanedioate D

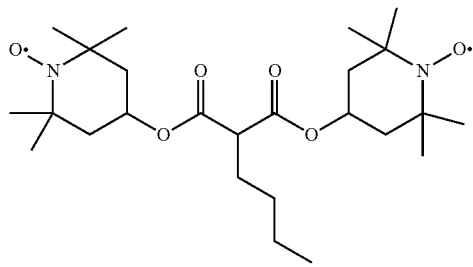

D 45.3 g (262.9 mmol) of 4-hydroxy-2,2,6,6-tetramethylpiperidine 1-oxyl (free radical) and 40.1 ml (289.15 mmol) of triethylamine are dissolved in 419 ml of dichloromethane (DCM) and cooled to −11° C. A solution of 25.9 g (131.4 mmol) of the acid chloride C in 252 ml of DCM is then added dropwise at −11° C. to −6° C. over the course of 1.5 hours (h). The reaction mixture is stirred at max. 0° C. for about 3 h, allowed to thaw slowly and stirred at room temperature (RT) for 18 h. Saturated NaHCO$_3$ solution is added at 3-6° C. with cooling, the mixture is stirred briefly, and the phases are separated. The water phase is extracted with DCM, and the organic phases are combined, washed with saturated NaCl solution, dried over sodium sulfate, filtered and evaporated in vacuo. The crude product obtained (orange solid) is filtered through silica gel with DCM/MTBE (9:1), and the product fractions are evaporated in vacuo, giving the product as orange crystals.

Step 1.5: Synthesis of bis(1-oxyl-2,2,6,6-tetramethylpiperidin-4-yl) 2-{3-[2,5-bis({4-butyl-5-[(1-oxyl-2,2,6,6-tetramethylpiperidin-4-yl)oxy]-4-{[(1-oxyl-2,2,6,6-tetramethylpiperidin-4-yl)oxy]carbonyl}-5-oxopentyl})phenyl]propyl}-2-butylpropanedioate 1'

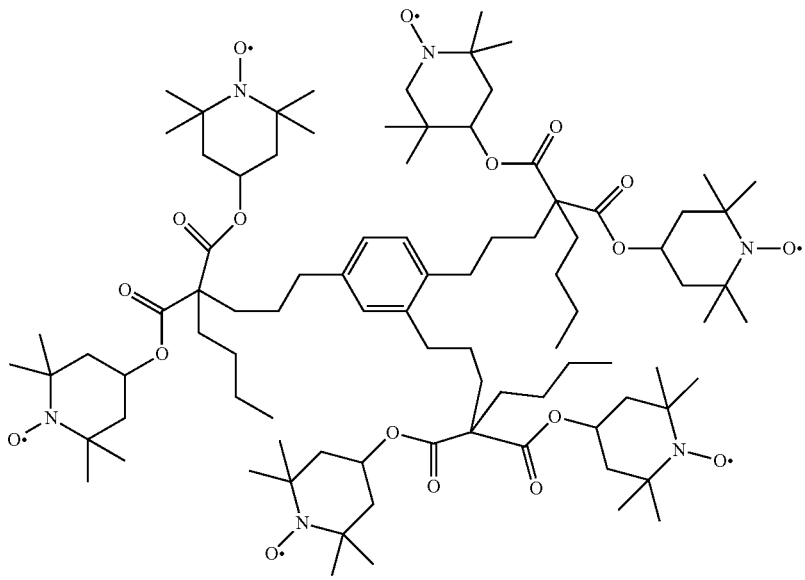

0.31 g (7.87 mmol) of sodium hydride (60% suspension in paraffin oil) is suspended in 9.7 ml of N,N-dimethylformamide (DMF). 3.75 g (7.87 mmol) of a solution of the bisradical D dissolved in 29.0 ml DMF are added dropwise with gentle cooling (evolution of gas), and the mixture is stirred at RT for 1 hour. 1.40 g (2.39 mmol) of trisiodide B are added dropwise to the reaction solution (5° C. evolution of heat over 5 minutes), and the mixture is stirred at RT for 3 h. The reaction mixture is carefully added to ammonium chloride solution and extracted with MTBE. The phases are separated, the water phase is extracted with MTBE, washed with saturated NaCl solution, dried over sodium sulfate, filtered and evaporated in vacuo. The orange crude product obtained is filtered through silica gel with ethyl acetate/heptane (1:1), and the product fractions are evaporated in vacuo, giving the product as an orange solid which foams up in a glass-like manner. The product has the following properties.

Phases: glass transition temperature (TG)=23.5° C., decomposition from 150° C.

MS (APCI)=1605.1 [M+H$^+$].

Step 1.6: Synthesis of bis(2,2,6,6-tetramethylpiperidin-4-yl) 2-{3-[2,5-bis({4-butyl-5-[(2,2,6,6-tetramethylpiperidin-4-yl)oxy]-4-{[(2,2,6,6-tetramethylpiperidin-4-yl)oxy]carbonyl}-5-oxopentyl})phenyl]propyl}-2-butylpropanedioate 1

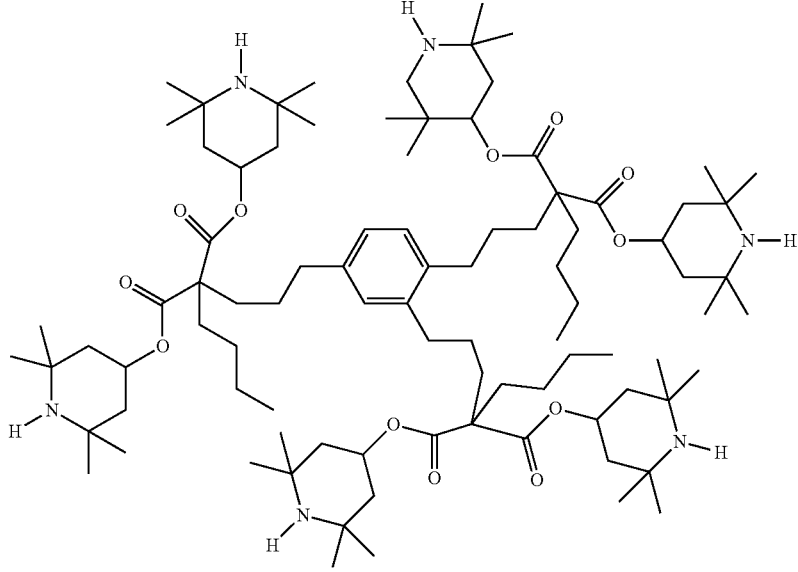

1.5 g (0.1 mmol) of hexaradical 1' are dissolved in 20 ml of THF, and 1.5 g of sponge nickel (Johnson-Matthey A-7000) are added. The mixture is stirred at a hydrogen pressure of 5 bar and 50° C. for 17 h. The reaction solution is allowed to cool to RT, filtered and evaporated in vacuo. The crude product obtained is purified by column chromatography on basic aluminium oxide (RediSep Rf) in a CombiFlash apparatus with dichloro-methane/methanol (95:5), and the product fractions are combined and evaporated in vacuo. The product is dried in a bulb-tube apparatus at 50° C. and $3.2 \times 10^{-1}$ mbar for 3 h, giving the product as a foaming, glass-like solid.

Phases: $T_g$ (glass transition temperature) 39° C. C (melting point) 41° C. I (isotropic).

MS (APCI)=1515.1 $[M+H]^+$.

$^1$H NMR (500 MHz, $CDCl_3$)

$\delta$=0.54-0.99 ($m_{(superimposed)}$, 16H, 6× NH, $CH_2$), 1.09-1.40 ($m_{(superimposed)}$, 97H, $CH_3$, $CH_2$), 1.48 ($m_c$, 6H, $CH_2$), 1.82-2.02 ($m_{(superimposed)}$, 24H, $CH_2$), 2.57 (t, J=7.63 Hz, 6H), 5.24 ($m_c$, 6H, $CH(CH_2)_2$), 6.93 ($d_{(superimposed\ with\ singlet)}$, J=7.87 Hz, 2H), 7.04 (d, J=7.72 Hz, 1H).

Synthesis Example 2

Synthesis of bis(1-oxyl-2,2,6,6-tetramethylpiperidin-4-yl) 2-(3-{3,5-bis[({4-butyl-5-[(1-oxyl-2,2,6,6-tetramethylpiperidin-4-yl)oxy]-4-{[(1-oxy-2,2,6,6-tetramethylpiperidin-4-yl)oxy]carbonyl}-5-oxopentyl}oxy)-carbonyl]benzoyloxy}propyl)-2-butylpropanedioate 2

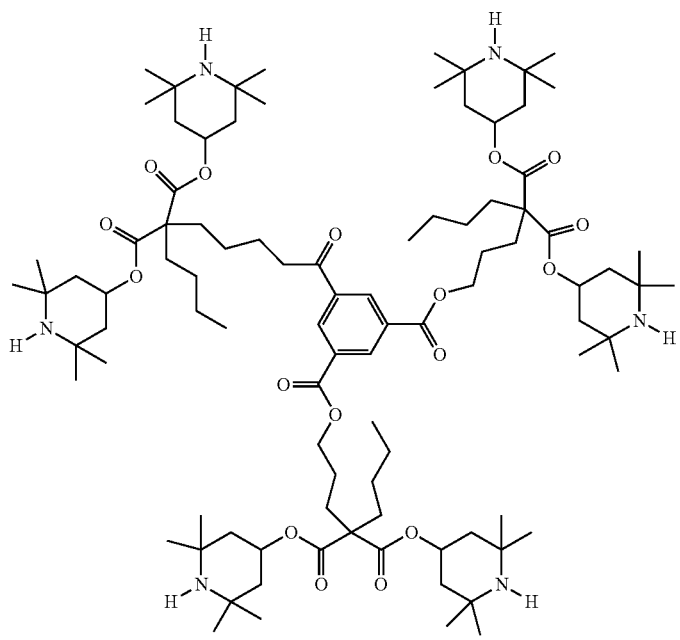

Step 2.1: Synthesis of bis(1-oxyl-2,2,6,6-tetramethylpiperidin-4-yl) 2-butyl-2-[3-(oxan-2-yloxy)propyl] propanedioate E

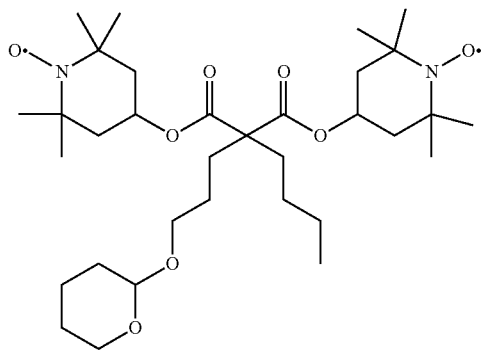

E 3.20 g (80.01 mmol) of sodium hydride (60% suspension in paraffin oil) are suspended in 30 ml of DMF. A solution of 32.40 g (69.14 mmol) of bisradical D (from the synthesis of compound 1) in 300 ml of DMF is added dropwise to the reaction solution with gentle cooling (evolution of gas), and the mixture is stirred at RT for 1 h. A solution of 19.0 g (85.16 mmol) of 2-(3-bromopropoxy)tetrahydropyran in 200 ml of DMF is then added dropwise at RT (0.5° C. evolution of heat). For degassing of the reaction mixture before an increase in temperature, a gentle stream of argon is passed through the reaction mixture by means of an immersed Pasteur pipette for 30 minutes, and the mixture is subsequently stirred at 35° C. for 18 h. The reaction solution is allowed to cool to RT, added to saturated NaCl solution and extracted with MTBE, and the phases are separated. The aqueous phase is extracted with MTBE, and the organic phases are combined, washed with saturated NaCl solution, dried over sodium sulfate, filtered and evaporated in vacuo, giving the crude product as a red oil, which, for purification, is filtered through silica gel with DCM/MTBE (9:1), giving the product as a red oil.

Step 2.2: Synthesis of bis(1-hydroxy-2,2,6,6-tetramethylpiperidin-4-yl) 2-butyl-2-(3-hydroxypropyl) propanedioate F

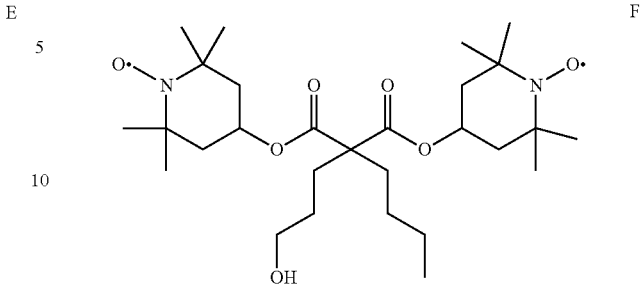

F 36.5 g (56.1 mmol) of bisradical E and 9.50 g (55.2 mmol) of toluene-4-sulfonic acid monohydrate are dissolved in a mixture of 500 ml of methanol and 50 ml of water, and the mixture is stirred at 40° C. for 5 h. The reaction solution is cooled to RT and adjusted to pH=9 using $NaHCO_3$ solution with cooling and evaporated in vacuo. The aqueous residue is extracted with MTBE, and the combined organic phases are washed with saturated NaCl solution, dried over sodium sulfate, filtered and evaporated in vacuo, giving a red oil, which is dissolved in 250 ml of DCM, 6.00 g (55.6 mmol) of $MnO_2$ are added, and the mixture is stirred at RT for 1 h. (In the case of removal of the THP protecting group, the free radical is in some cases also converted into the OH compound, which is reversed using $MnO_2$). The reaction mixture is filtered through silica gel with DCM and evaporated in vacuo. The crude product obtained is filtered through silica gel with DCM/MTBE (7:3), and the product fractions are evaporated in vacuo to give a red oil.

Step 2.3: Synthesis of bis(1-oxyl-2,2,6,6-tetramethylpiperidin-4-yl) 2-(3-{3,5-bis[({4-butyl-5-[(1-oxyl-2,2,6,6-tetramethylpiperidin-4-yl)oxy]-4-{[(1-oxy-2,2,6,6-tetramethylpiperidin-4-yl)oxy]carbonyl}-5-oxopentyl}oxy)carbonyl]-benzoyloxy}propyl)-2-butylpropanedioate 2'

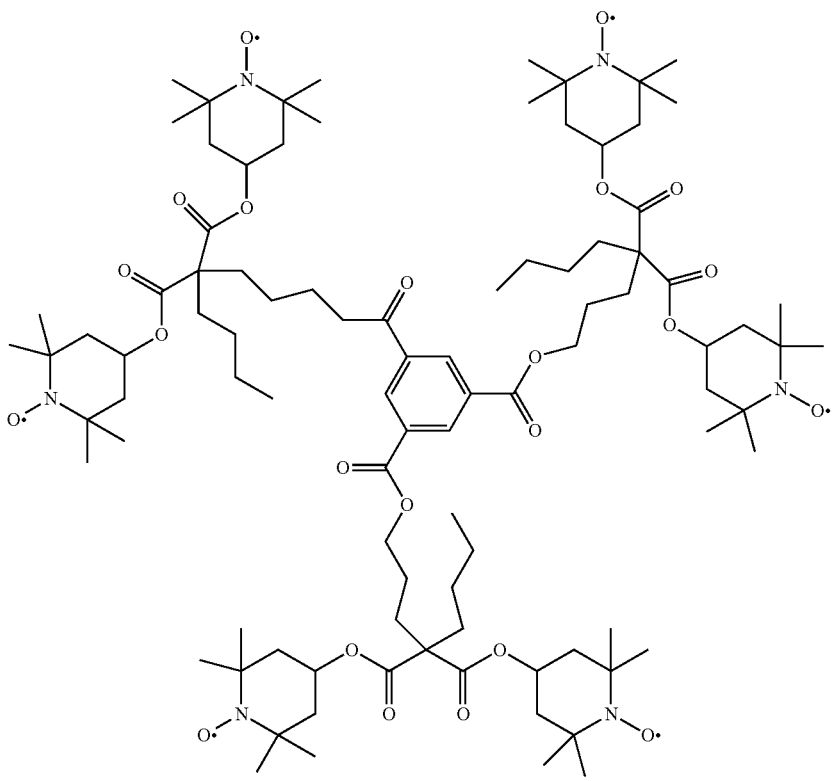

2'

6.70 g (11.7 mmol of F and 50.0 mg (0.41 mmol) of 4-(dimethylamino)-pyridine are dissolved in 100 ml of dichloromethane at RT, and the mixture is cooled to 4° C. 5.00 ml (36.1 mmol) of triethylamine are then added, and a solution of 1.00 g (3.77 mmol) of 1,3,5-benzenetricarbonyl chloride in 10 ml of DCM is subsequently added dropwise at 3-4° C. When the evolution of heat is complete, the mixture is allowed to warm to RT and is subsequently stirred at RT for 18 h. Ammonium chloride solution is then added with cooling, the mixture is stirred briefly, the phases are separated, and the aqueous phase is extracted with DCM. The combined organic phases are washed with dilute NaCl solution (better phase separation), dried over sodium sulfate, filtered and evaporated in vacuo, giving the reaction product as a red solidifying foam. For further purification, the product is filtered through silica gel with DCM/MTBE (9:1 to 85:15), and the product fractions are evaporated in vacuo. The reaction product obtained is a red, solidifying foam. It has the following properties.

Phases: $T_g$ (glass transition temperature) 52° C., C (melting point) 57° C. I, decomposition >175° C.

MS (APCI)=1734.

The following compounds are prepared analogously to the synthesis sequence(s) described.

Substance/Synthesis Example 2'

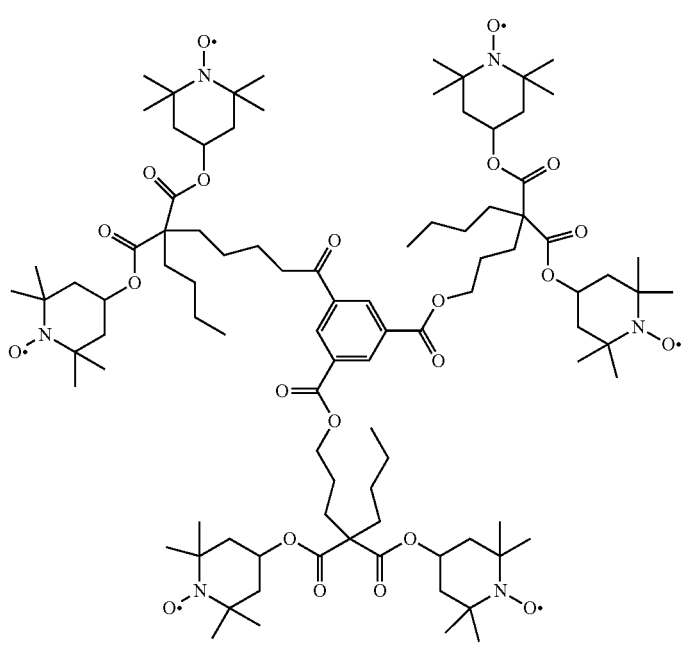

Substance/Synthesis Example 2

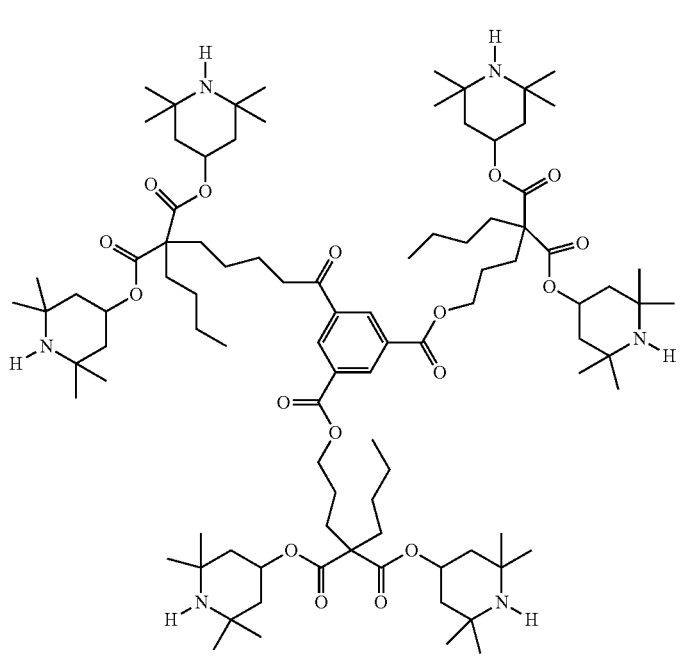

Substance/Synthesis Example 3'
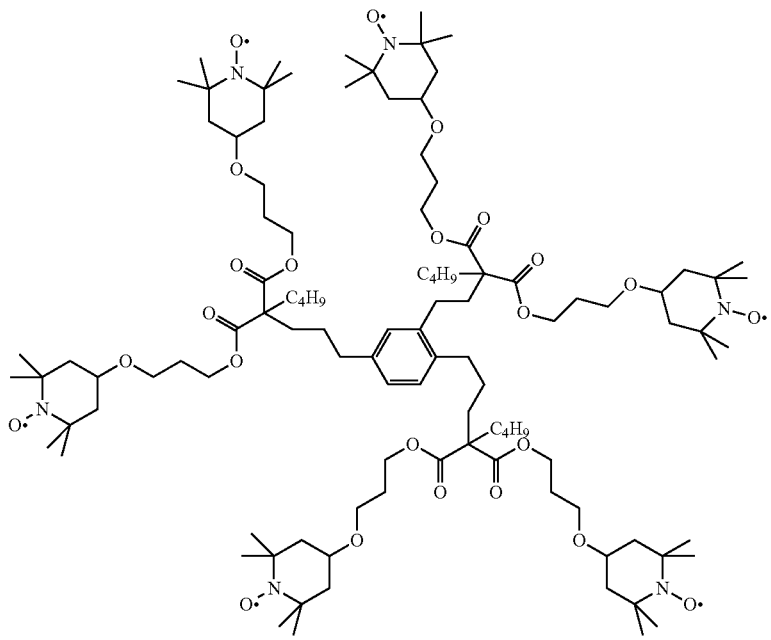
3'
30
Phases: $T_g$ (glass transition temperature) −3° C. I (isotropic), decomposition >100° C.
35
Substance/Synthesis Example 3
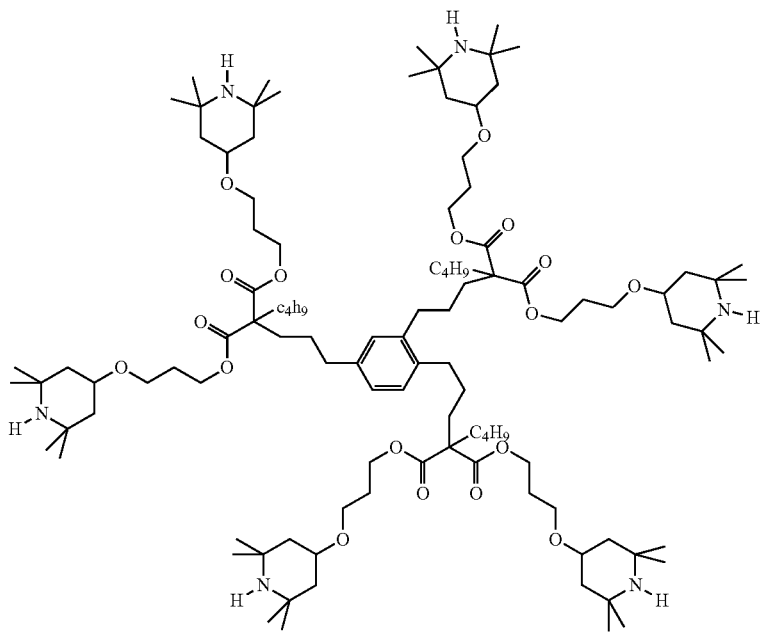
3

Substance/Synthesis Example 4'
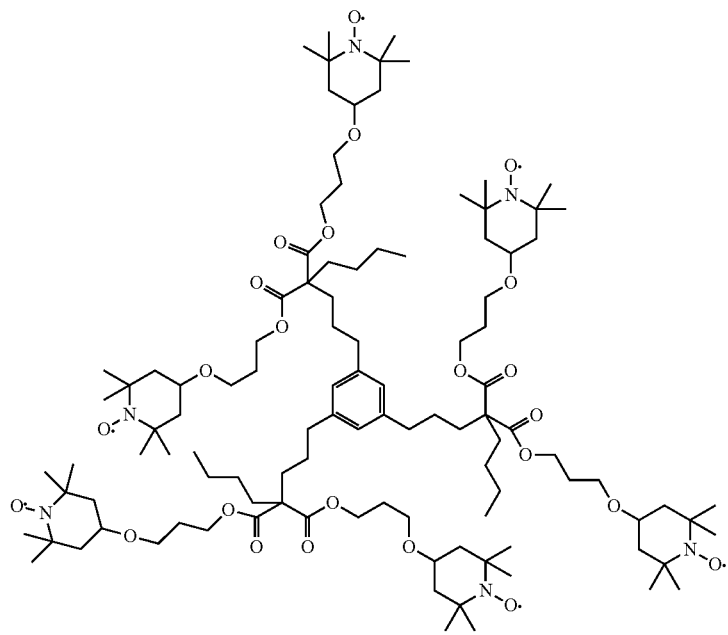
4'
Phases: $T_g$ (glass transition temperature) 5° C. I (isotropic), decomposition >180° C.
Substance/Synthesis Example 4
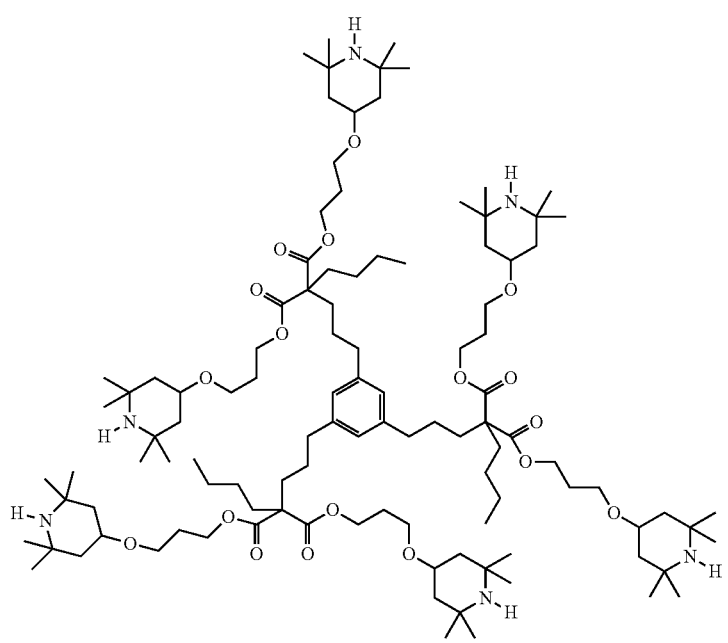
4

Substance/Synthesis Example 5'
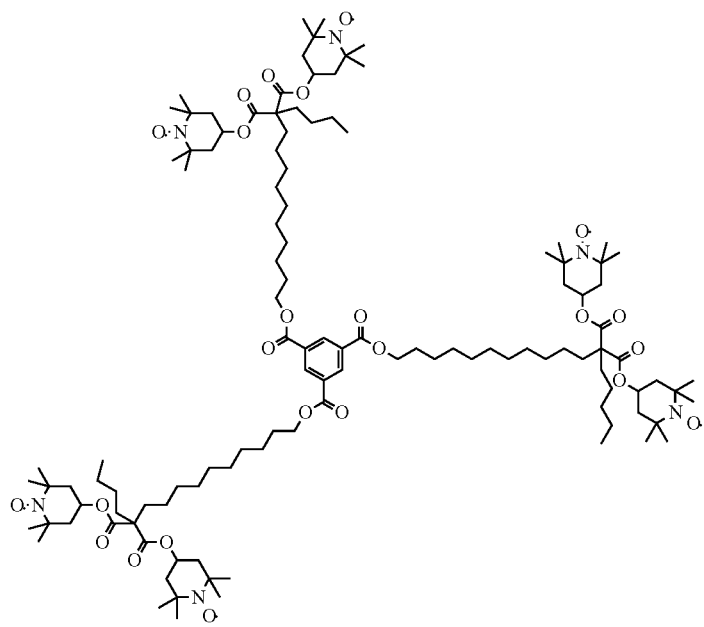
Phases: $T_g$ (glass transition temperature) 5° C. I (isotropic), decomposition >170° C.
Substance/Synthesis Example 5
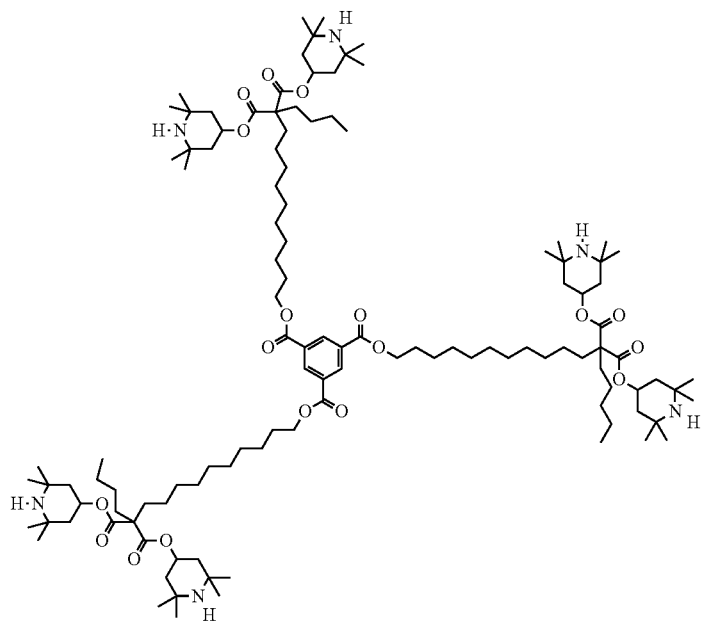

Substance/Synthesis Example 6'
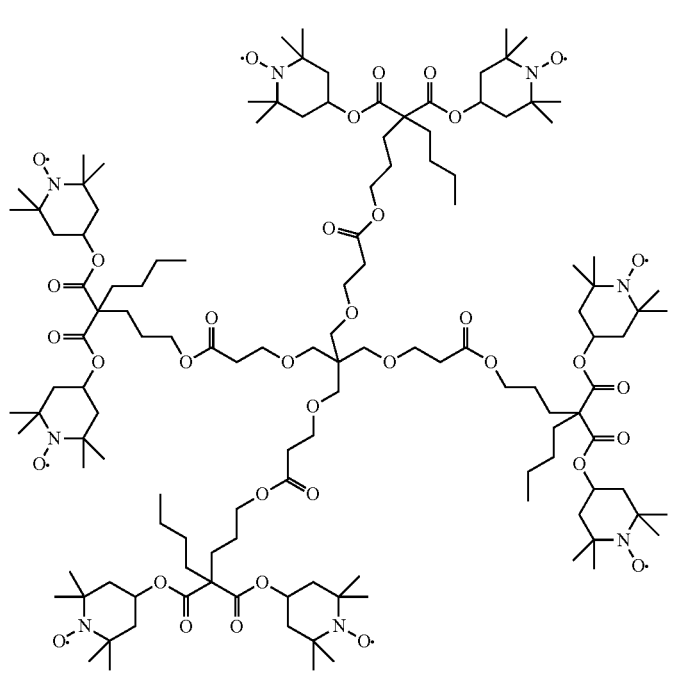
6'
Phases: $T_g$ (glass transition temperature) 27° C. I (isotropic).
Substance/Synthesis Example 6
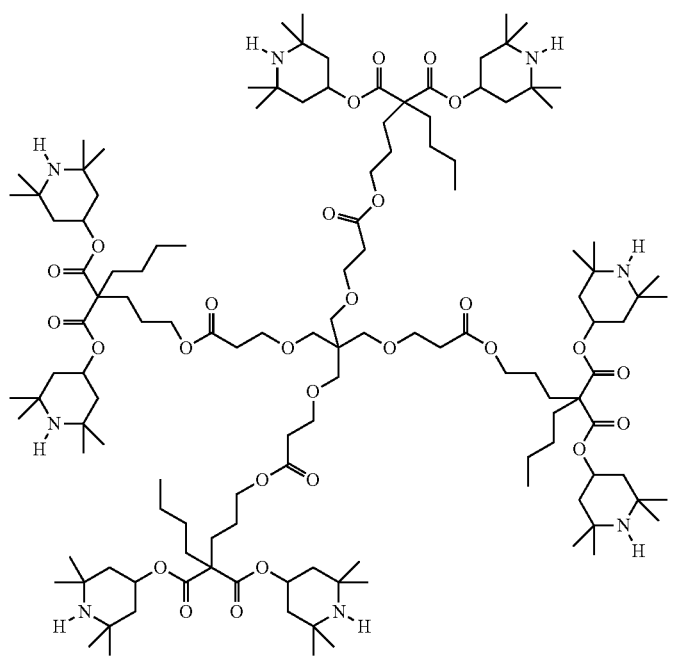
6

Substance/Synthesis Example 7
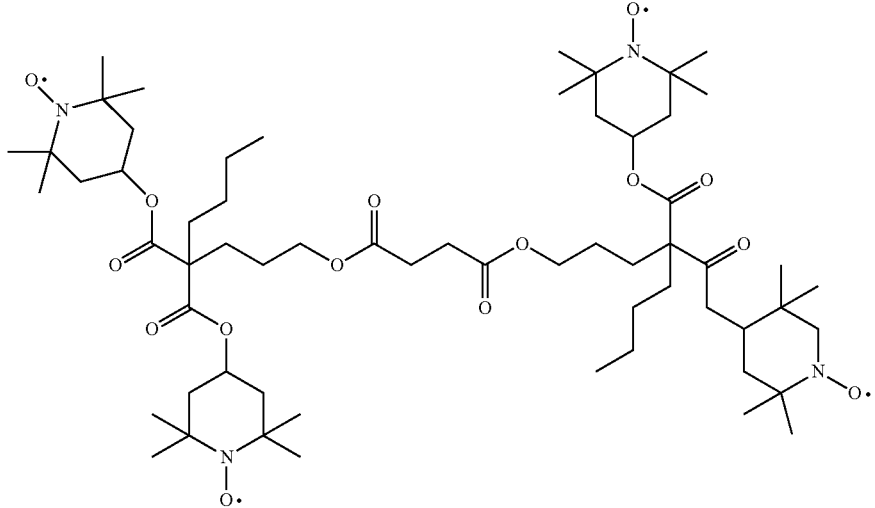
Substance/Synthesis Example 7
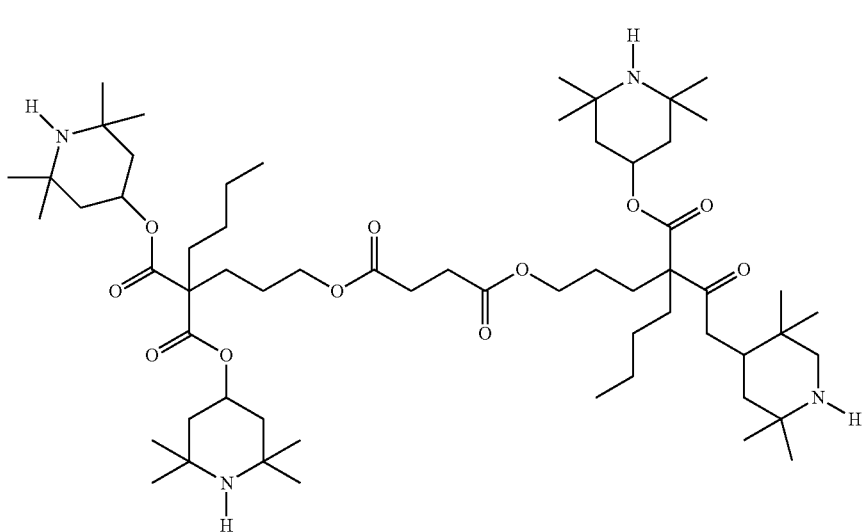
Phases: (glass transition temperature) 14° C. I (isotropic).

Substance/Synthesis Example 8'
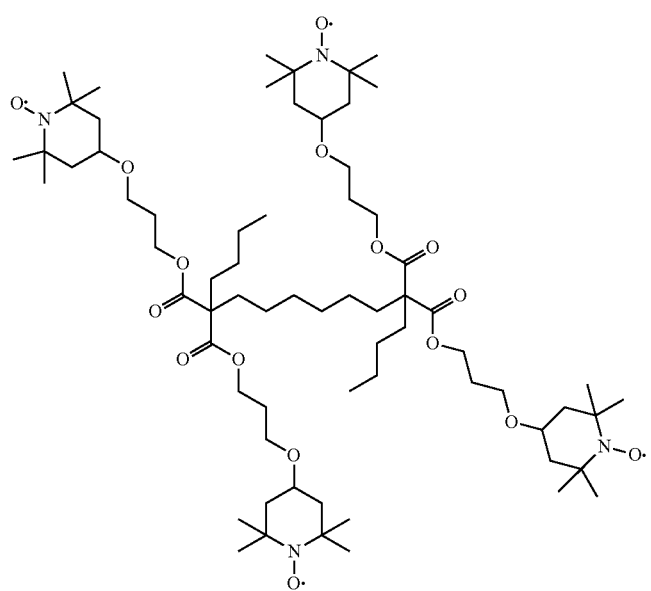
8'
Substance/Synthesis Example 8
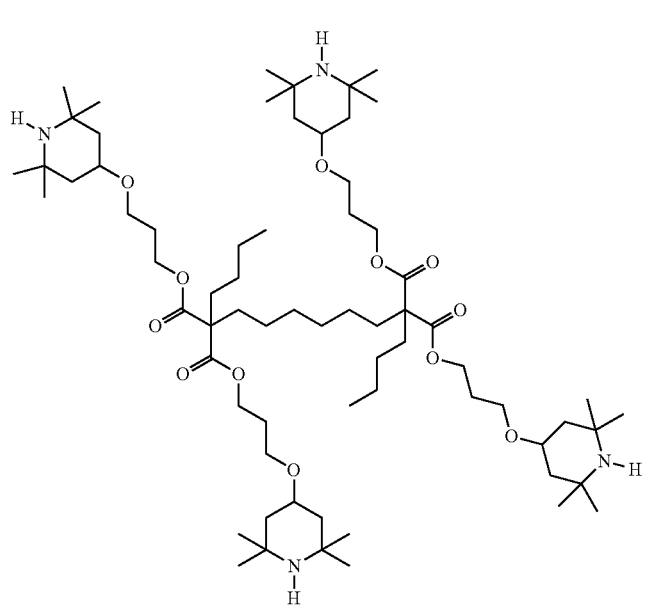
8
Phases: $T_g$ (glass transition temperature) −3° C. I (isotropic).

Substance/Synthesis Example 9'
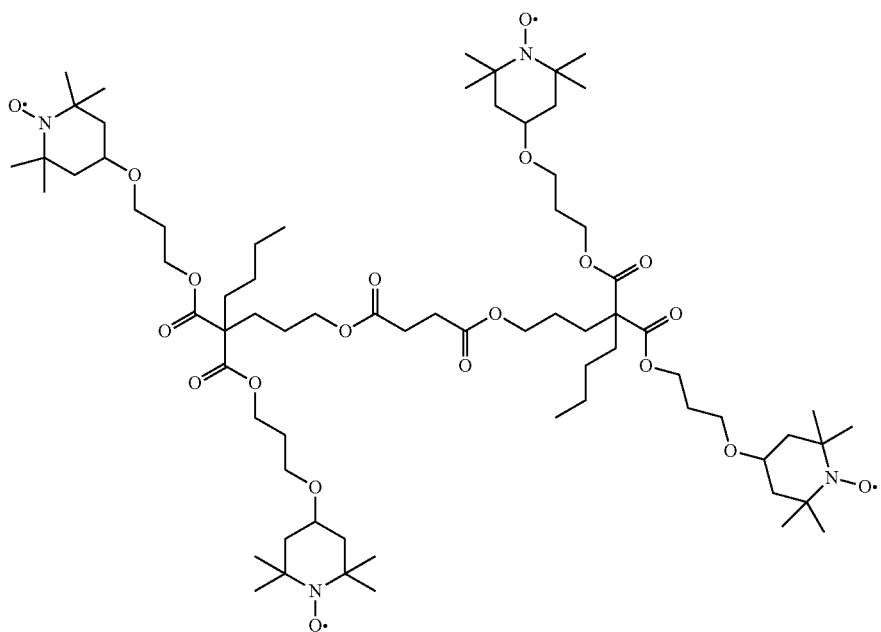
Substance/Synthesis Example 9
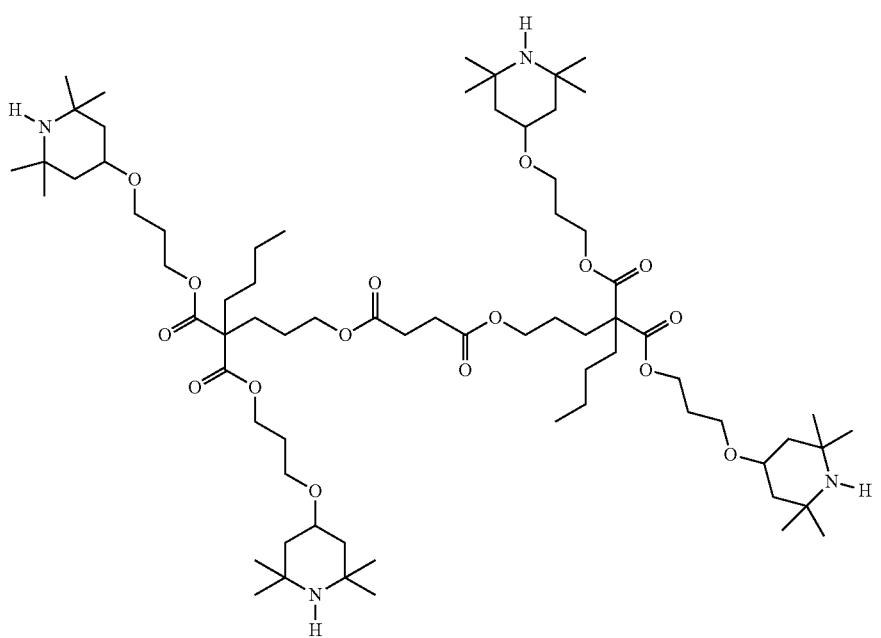
Phases: $T_g$ (glass transition temperature) −3° C. I (isotropic).

Substance/Synthesis Example 10: Synthesis of 4-(3-{3-[3,5-bis({3-[(2,2,6,6-tetramethylpiperidin-4-yl)oxy]propoxy})phenyl]-5-{3-[(2,2,6,6-tetramethylpiperidin-4-yl)oxy]propoxy}phenoxy}propoxy)-2,2,6,6-tetramethylpiperidine

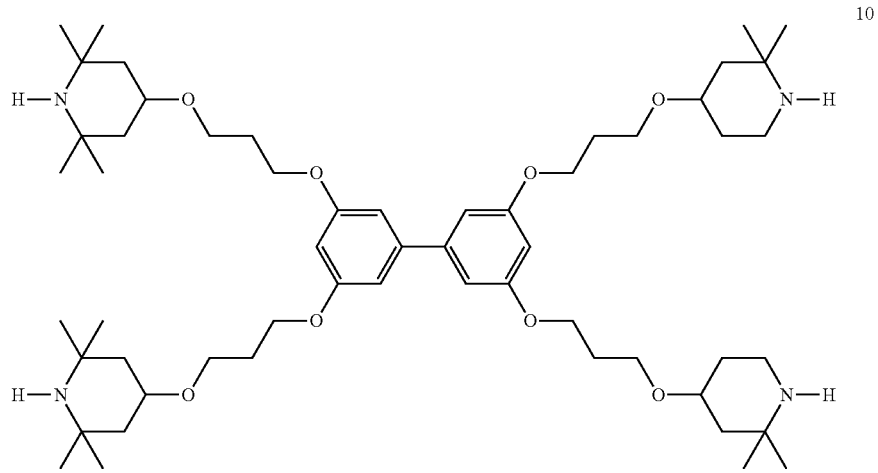 [SMILES: CC1(C)CC(OCCCOc2cc(OCCCOC3CCNC(C)(C)C3)cc(-c3cc(OCCCOC4CC(C)(C)NC(C)(C)C4)cc(OCCCOC4CC(C)(C)NC(C)(C)C4)c3)c2)CCN1]

Step 8.1: Synthesis of 1-benzyl-2,2,6,6-tetramethylpiperidin-4-ol A

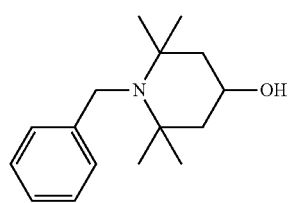

A 37.80 ml (318.2 mmol) of benzyl bromide and 100.0 g (635.9 mmol) of 2,2,6,6-tetramethylpiperidin-4-ol are dissolved in 500 ml of N,N-dimethylformamide (DMF), and the mixture is stirred at 120° C. for 18 hours (h). The reaction solution is cooled to room temperature (RT) and stirred into a mixture of water and ice. The mixture is stirred for 30 min., and the precipitated solid is filtered off with suction and extracted with methyl tertiary-butyl ether (MTB ether). The product solution is washed a number of times with saturated sodium chloride solution, and the organic phase is dried over sodium sulfate, filtered and evaporated in vacuo. The crystalline crude product obtained is recrystallised from heptane/isopropanol (5:1) at 5° C., and the crystals are filtered off with suction and dried in vacuo at 40° C. for 18 h, giving the reaction product as a colourless, crystalline solid.

Step 8.2: Synthesis of 1-benzyl-2,2,6,6-tetramethyl-4-[3-(oxan-2-yloxy)-propoxy]piperidine B

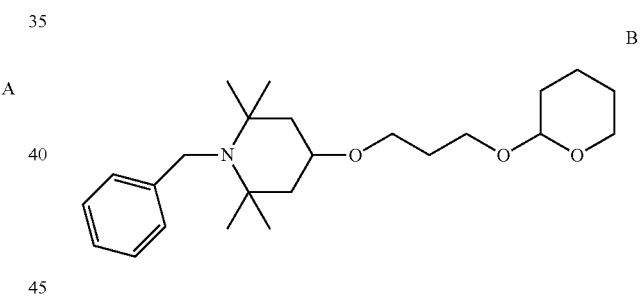

B 35.00 g (141.5 mmol) of tetramethylpiperidine A, 47.20 g (211.5 mmol) of 2-(3-bromopropoxytetrahydropyran) and 20.00 g (62.04 mmol) of tetra-n-butylammonium bromide are suspended in 270 ml of toluene, and 110 ml (2.10 mol) of sodium hydroxide solution (50%) are rapidly added dropwise at room temperature (RT). The reaction mixture is stirred at 60° C. for 16 hours (h) and subsequently allowed to cool to RT. The reaction mixture is carefully added to a mixture of ice-water and toluene, and the phases are separated. The aqueous phase is extracted with toluene, and the combined organic phases are washed with saturated sodium chloride solution, dried over sodium sulfate, filtered and evaporated in vacuo, giving a yellow, partially crystalline crude product, to which 300 ml of heptane are added, and the mixture is stirred and filtered. The reaction product is obtained in the mother liquor as a yellow oil, which is filtered through silica gel with toluene/ethyl acetate (9:1 to 3:1). The product fractions are combined and evaporated in vacuo, giving the product as a slightly yellow oil.

Step 8.3: Synthesis of 3-[(1-benzyl-2,2,6,6-tetramethylpiperidin-4-yl)oxy]propan-1-ol C

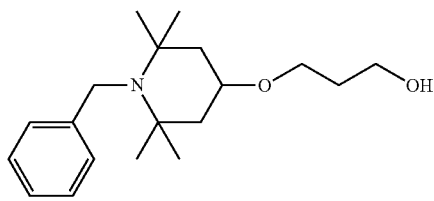

34.60 g (80.91 mmol) of B and 20.00 g (116.1 mmol) of toluene-4-sulfonic acid monohydrate are dissolved in 700 ml of methanol, and 100 ml of water are added at RT (exothermic/7 K). The reaction solution is stirred at 40° C. for 1 h, subsequently evaporated in vacuo and diluted with methyl tert-butyl ether (MTBE). The mixture is carefully washed with saturated NaHCO₃ solution, and the phases are separated. The organic phase is washed with saturated NaCl solution, dried over sodium sulfate, filtered and evaporated in vacuo, giving the crude product as a yellow oil, which is filtered through silica gel with dichloromethane (DCM) and MTBE (3:1). The product fractions are combined, giving the reaction product as a virtually colourless oil.

Step 8.4: Synthesis of 1-benzyl-4-[3-(3-{3-[(1-benzyl-2,2,6,6-tetramethylpiperidin-4-yl)oxy]propoxy}-5-bromophenoxy)propoxy]-2,2,6,6-tetramethylpiperidine D

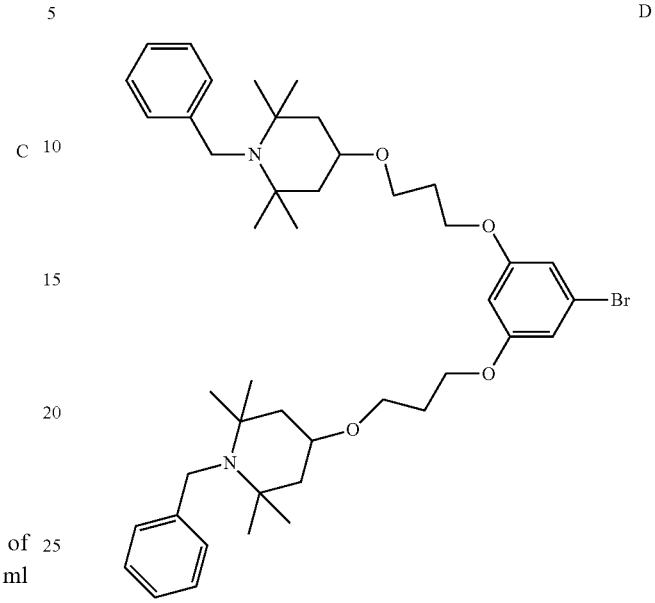

5.80 g (30.7 mmol) of 5-bromobenzene-1,3-diol, 21.50 g (70.4 mmol) of alcohol C from the preceding step and 18.51 g (70.58 mmol) of triphenylphosphine are dissolved in 120 ml of tetrahydrofuran (THF) and cooled to 0° C. 14.70 ml (70.58 mmol) of diisopropyl azodicarboxylate are added dropwise to the reaction solution, and the mixture is stirred at RT for 16 h. The reaction mixture is evaporated in vacuo, 200 ml of heptane are added, and the mixture is stirred vigorously. The precipitated triphenylphosphine oxide is filtered off, and the mother liquor is washed with 100 ml of heptane and evaporated in vacuo. The crude product obtained is filtered through silica gel with heptane/MTBE (7:3), and the combined product fractions are evaporated in vacuo, giving the reaction product as a viscous oil.

Step 8.5: Synthesis of 1-benzyl-4-[3-(3-{3-[(1-benzyl-2,2,6,6-tetramethylpiperidin-4-yl)oxy]propoxy}-5-[3,5-bis({3-[(1-benzyl-2,2,6,6-tetramethylpiperidin-4-yl)oxy]propoxy})-phenyl]phenoxy)propoxy]-2,2,6,6-tetramethylpiperidine E

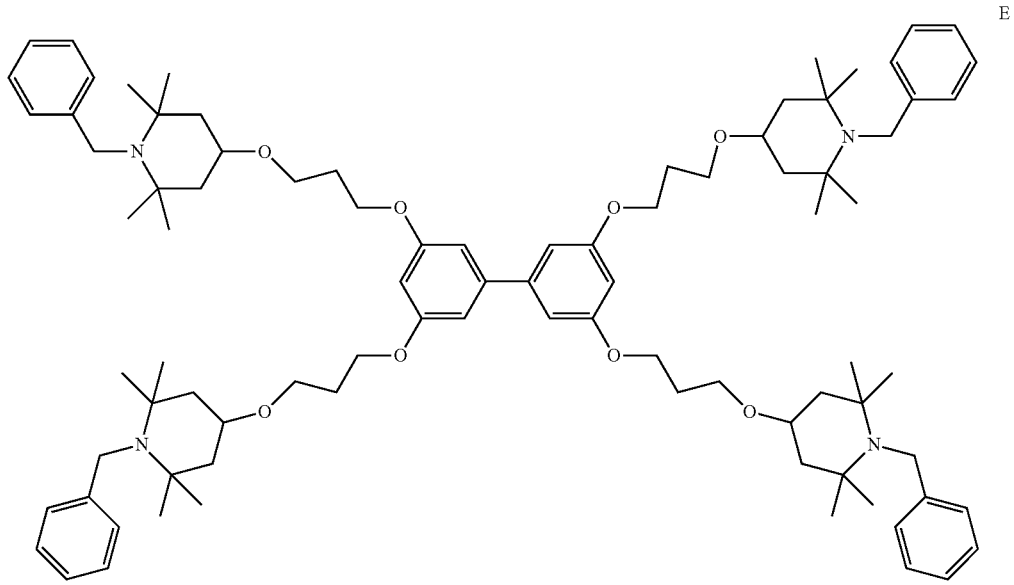 [SMILES: CC1(C)CC(OCCCOc2cc(OCCCOC3CC(C)(C)N(Cc4ccccc4)C(C)(C)C3)cc(-c3cc(OCCCOC4CC(C)(C)N(Cc5ccccc5)C(C)(C)C4)cc(OCCCOC4CC(C)(C)N(Cc5ccccc5)C(C)(C)C4)c3)c2)CC(C)(C)N1Cc1ccccc1]

14.60 g (19.11 mmol) of the bromide D from the preceding step, 2.54 g (10.0 mmol) of bis(pinacolato)diboron and 2.81 g (28.7 mmol) of potassium acetate are initially introduced in 150 ml of dioxane and degassed under an argon atmosphere for 30 min. 220.00 mg (0.30 mmol) of $PdCl_2$-dppf are added, and the reaction mixture is stirred at 100° C. for 1 h. It is then cooled to below the boiling point, a further 220.00 mg (0.30 mmol) of $PdCl_2$-dppf and 25 ml (50 mmol) of sodium carbonate solution (2 M) are added, and the mixture is stirred at 100° C. for 20 h. The reaction mixture is allowed to cool to RT, water and MTBE are added, and the phases are separated. The water phase is extracted with MTBE, and the organic phases are combined, washed with water, dried over sodium sulfate, filtered and evaporated in vacuo. The crude product is obtained as a black oil and is filtered through silica gel with heptane/MTBE (8:2 to 7:3).

The combined product fractions are evaporated in vacuo, giving the reaction product as a yellow resin.

MS (APCI)=1367.9 $[M]^+$ $^1$H NMR (500 MHz, $CDCl_3$)

δ=0.99 (s, 24H, $CH_3$), 1.13 (s, 24H, $CH_3$), 1.45 (t, J=11.7 Hz, 8H, $CH_2$), 1.94 (dd, J=12.25, 3.84 Hz, 4H, $CH_2$), 2.09 (quint, J=6.16 Hz, 4H, $CH_2$), 3.71 (t$_{(superimposed\ with\ multiplet)}$, J=6.21 Hz, 6H, $CH_2$, CH), 3.83 (s, 8H, $CH_2$), 4.15 (t, 6.15 Hz), 6.53 (t, 2.06 Hz, 2H), 6.76 (d, J=2.12 Hz, 4H), 7.16 (t, 7.26 Hz, 4H), 7.28 (t, 7.72 Hz, 8H), 7.43 (d, J=7.49 Hz, 8H).

Step 8.6: Synthesis of 4-(3-{3-[3.5-bis({3-[(2,2,6,6-tetramethylpiperidin-4-yl)oxy]propoxy})phenyl]-5-{3-[(2,2,6,6-tetramethylpiperidin-4-yl)oxy]propoxy}phenoxy}propoxy)-2,2,6,6-tetramethylpiperidine 10

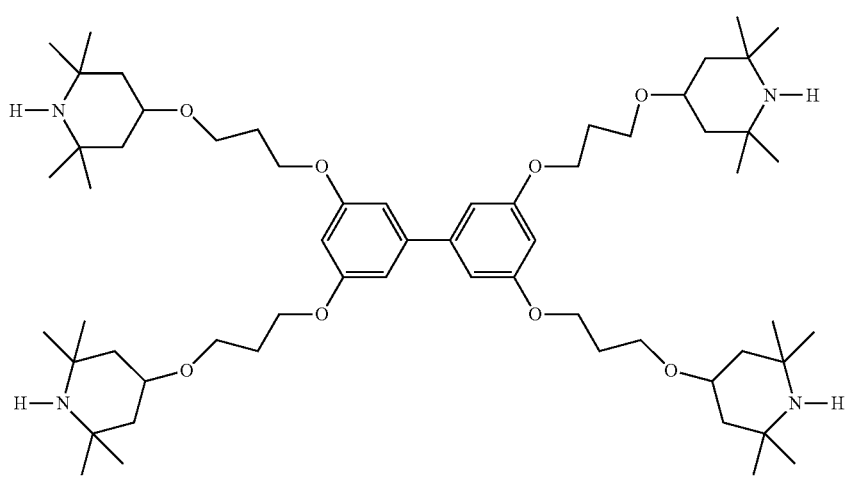

8.50 g (6.21 mmol) of the product E from the preceding step are dissolved in 107 ml of tetrahydrofuran, 3.00 g of 5% Pd/C (50% of water, Degussa) are added, and the mixture is stirred under a hydrogen atmosphere at atmospheric pressure and room temperature (RT) for 17 h. The reaction mixture is filtered and evaporated in vacuo. The residue is taken up in 100 ml of MTBE, 50 ml of 2 N hydrochloric acid are added, and the phases are separated. The aqueous phase is extracted with MTBE, and the aqueous phase is then adjusted to pH 12-13 using 32% sodium hydroxide solution and extracted with MTBE ether. The combined organic phases are washed with saturated sodium chloride solution, dried over sodium sulfate, filtered and evaporated in vacuo. The crude product obtained is filtered through $Al_2O_3$ ("basic aluminium oxide") with dichloromethane/methanol, and the product fractions are combined and evaporated in vacuo, giving the product as a slightly yellow oil, which solidifies.

Phases: $T_g$ (glass transition temperature) −4° C., T(C,I) (melting point) 64° C. I (isotropic).

MS (APCI)=1007.7 $[M+H]^+$ $^1$H NMR (500 MHz, $CDCl_3$)

δ=0.62 ($s_{(broad)}$, 4H, NH), 1.02 (t, J=11.76, 8H), 1.15 (s, 24H, $CH_3$), 1.19 (s, 24H, $CH_3$), 1.98 (dd, 12.49, 3.9 Hz 8H), 2.07 (quint., 6.13 Hz, 8H), 3.69 ($t_{(superimposed)}$, J=5.8 Hz, 12H), 4.12 (t, J=6.1 Hz, 8H), 6.50 ($s_{(broad)}$=2H), 6.73 (d, J=2.1 Hz, 4H).

Substance/Synthesis Example 11: Synthesis of

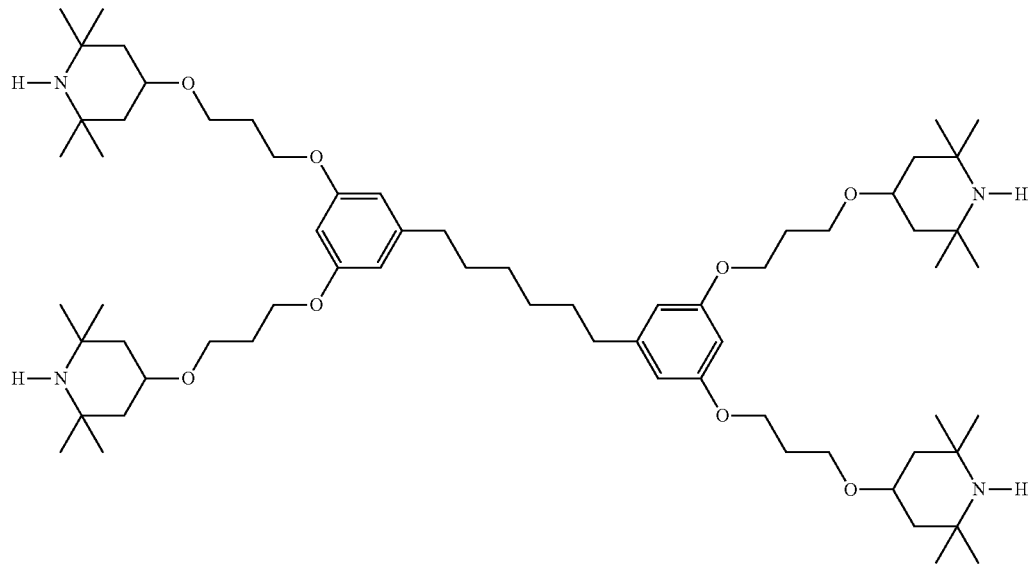 [SMILES: CC1(C)CC(OCCCOc2cc(CCCCCCc3cc(OCCCOC4CC(C)(C)NC(C)(C)C4)cc(OCCCOC4CC(C)(C)NC(C)(C)C4)c3)cc(OCCCOC3CC(C)(C)NC(C)(C)C3)c2)CC(C)(C)N1]

The compound is prepared analogously, giving a colourless oil.

Phases: $T_g$ (glass transition temperature) −118° C.

$^1$H NMR (500 MHz, $CDCl_3$)

δ=6.35 (dd, J=13.3, 2.2 Hz, 6H), 4.05 (t, J=6.1 Hz, 8H), 3.81-3.51 (m, 12), 2.57-2.48 (m, 4H), 2.04 (p, J=6.2 Hz, 8H), 1.98 (dd, J=12.5, 3.9 Hz, 8H), 1.67-1.56 (m, 4H), 1.36 (d, J=4.1 Hz, 6H), 1.18 (d J=19.7 Hz, 48H), 1.02 (t, J=11.7 Hz, 8H), 0.69 (s, 4H).

Mixture Examples

Liquid-crystal mixtures having the compositions and properties as indicated in the following tables are prepared and investigated. The improved stability of the mixtures comprising compounds of the formula I is shown by comparison with unstabilised base mixtures as reference (Ref.).

Examples 1.1.1 to 1.3.3 and Corresponding Comparative Examples

The following mixture (M-1) is prepared and investigated.

| Mixture M-1 | | |
|---|---|---|
| Composition | | |
| Compound | | Concentration |
| No. | Abbreviation | /% by weight |
| 1 | B-2O-O5 | 4.0 |
| 2 | CY-3-O2 | 10.0 |
| 3 | CY-5-O2 | 1.5 |
| 4 | CCY-3-O2 | 10.0 |
| 5 | CCY-5-O2 | 7.0 |
| 6 | CPY-2-O2 | 10.0 |
| 7 | CPY-3-O2 | 10.0 |
| 8 | PYP-2-3 | 5.5 |
| 9 | CC-3-V | 32.0 |
| 10 | CC-3-V1 | 10.0 |
| Σ | | 100.0 |

-continued

| Mixture M-1 | |
|---|---|
| Physical properties | |
| T(N, I) = | 85.0° C. |
| $n_e$(20° C., 589 nm) = | 1.5868 |
| Δn(20° C., 589 nm) = | 0.1047 |
| $ε_⊥$(20°, 1 kHz) = | 6.9 |
| Δε(20°, 1 kHz)= | −3.4 |
| $γ_1$(20° C.) = | 108 mPa · s |
| $k_{11}$(20° C.) = | 14.6 pN |
| $k_{33}$(20° C.) = | 17.4 pN |

-continued

Mixture M-1

| | |
|---|---|
| $V_0(20°\ C.) =$ | t.b.d. V |
| $V_{10}(20°\ C.) =$ | t.b.d. V |

Note:
Here, as throughout the present application, t.b.d. means to be determined, unless indicated otherwise.

Mixture M-1 is divided into several parts and investigated as described below.

Firstly, the stability of the voltage holding ratio of mixture (M-1) itself is determined. The stability of mixture M-1 to UV exposure is investigated in a test cell having an alignment material for planar alignment (polyimide AL-16301 from Japan Synthetic Rubber), with a layer thickness of 6.5 μm and flat ITO electrodes. To this end, corresponding test cells are irradiated in the Suntest for 30 min. The voltage holding ratio is then determined in each case after 5 minutes at a temperature of 100° C. The addressing frequency (or measurement frequency) here is 60 Hz, unless specifically indicated otherwise. The results are compiled in Table 1a.

Here, as below, six test cells are filled and investigated for each individual mixture. The values indicated are the mean of the six individual values.

100 ppm, 500 ppm and 1000 ppm of the reference compound (called R-1 here)

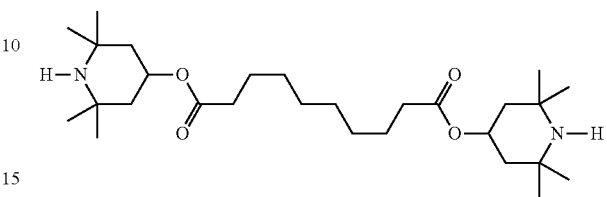

are then added to each of 3 further parts of mixture M-1, and the stability of the resultant mixtures (C-1-1.1, C-1-1.2 and C-1-1.3) is investigated as described above. The results are shown in the following table, Table 1a.

Next, 100 ppm, 500 ppm and 1000 ppm of in each case one of the compounds I-1 to I-3

I-1

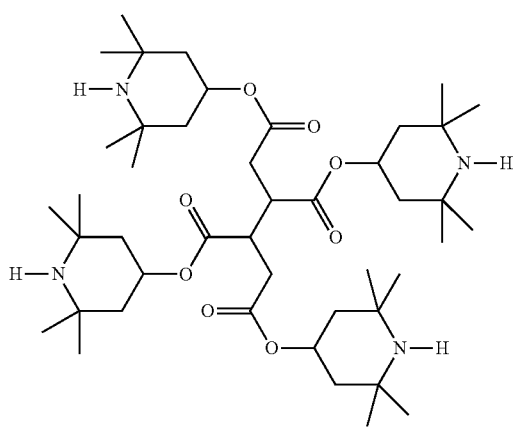

I-1

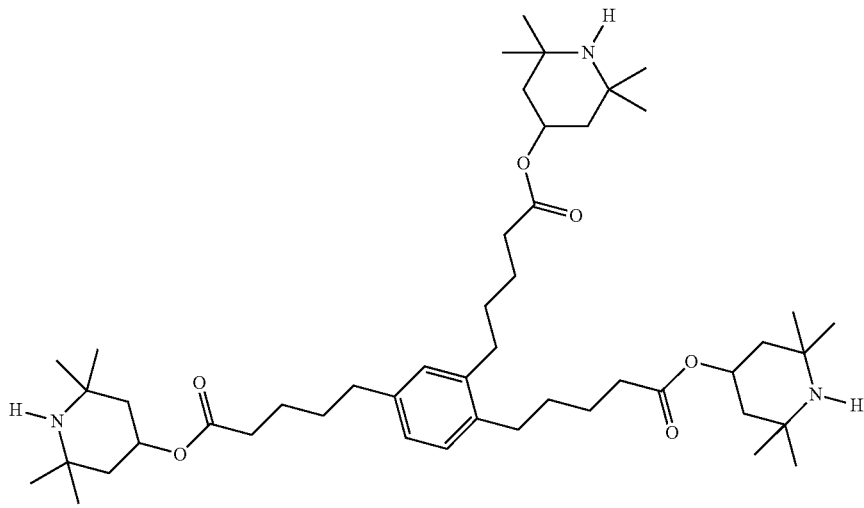

-continued

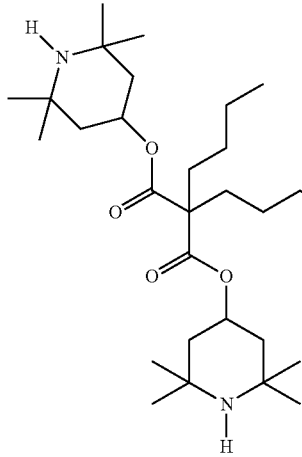

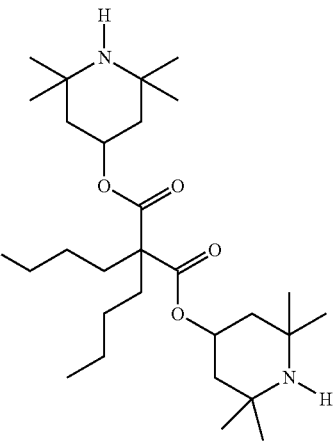

I-3 are added to sets of in each case three corresponding, remaining parts of mixture M-1, and the stability of the resultant mixtures (M-1-1.1 to M-1-1.3, M-2-2.1 to M-1-2.3 and M-1-3.1 to M-1-3.3) is investigated as described above. The results are shown in the following table, Table 1a.

The relative deviations of the "voltage holding ratio" values in various measurement series are typically in the range from about 3 to 4%.

TABLE 1a

| Ex. | Mixture | Stabiliser | c(stab.)/ ppm | VHR(t)/% @ 100° C., 60 Hz | |
|---|---|---|---|---|---|
| | | | | t = 0 h | t = 30 min |
| (Ref.) | M-1 | None | 0 | 69 | 52 |
| C1.1 | C-1-1.1 | R-1 | 100 | 76.5 | 70.0 |
| C1.2 | C-1-1.2 | R-1 | 500 | 81.0 | 75.5 |
| C1.3 | C-1-1.3 | R-1 | 1000 | 79.5 | 74.8 |
| M1.1.1 | M-1-1.1 | I-1 | 100 | 86.4 | 78.8 |
| M1.1.2 | M-1-1.2 | I-1 | 500 | 90.6 | 86.0 |
| M1.1.3 | M-1-1.3 | I-1 | 1000 | 90.7 | 86.9 |
| M1.2.1 | M-1-2.1 | I-2 | 100 | 84.5 | 76.2 |
| M1.2.2 | M-1-2.2 | I-2 | 500 | 87.7 | 82.4 |
| M1.2.3 | M-1-2.3 | I-2 | 1000 | 86.5 | 80.4 |
| M1.3.1 | M-1-3.1 | I-3 | 100 | 81.7 | 74.5 |
| M1.3.2 | M-1-3.2 | I-3 | 500 | 89.5 | 86.6 |
| M1.3.3 | M-1-3.3 | I-3 | 1000 | 87.8 | 85.5 |

It is readily evident here that compounds I-1 to I-3 exhibit clearly stabilising properties, even in relatively low concentrations.

The investigations described above are repeated at an addressing/measurement frequency of 10 Hz. The results are compiled in the following table, Table 1 b.

TABLE 1b

| Ex. | Mixture | Stabiliser | c(stab.)/ ppm | VHR(t)/% @ 100° C., 10 Hz | |
|---|---|---|---|---|---|
| | | | | t = 0 h | t = 30 min |
| (Ref.) | M-1 | None | 0 | 44 | 26 |
| C1.1 | C-1-1.1 | R-1 | 100 | 60.2 | 50.4 |
| C1.2 | C-1-1.2 | R-1 | 500 | 59.3 | 53.0 |
| C1.3 | C-1-1.3 | R-1 | 1000 | 50.9 | 50.4 |

TABLE 1b-continued

| Ex. | Mixture | Stabiliser | c(stab.)/ ppm | VHR(t)/% @ 100° C., 10 Hz | |
|---|---|---|---|---|---|
| | | | | t = 0 h | t = 30 min |
| M1.1.1 | M-1-1.1 | I-1 | 100 | 66.9 | 54.5 |
| M1.1.2 | M-1-1.2 | I-1 | 500 | 79.6 | 71.9 |
| M1.1.3 | M-1-1.3 | I-1 | 1000 | 77.7 | 72.5 |
| M1.2.1 | M-1-2.1 | I-2 | 100 | t.b.d. | t.b.d. |
| M1.2.2 | M-1-2.2 | I-2 | 500 | t.b.d. | t.b.d. |
| M1.2.3 | M-1-2.3 | I-2 | 1000 | t.b.d. | t.b.d. |
| M1.3.1 | M-1-3.1 | I-3 | 100 | t.b.d. | t.b.d. |
| M1.3.2 | M-1-3.2 | I-3 | 500 | t.b.d. | t.b.d. |
| M1.3.3 | M-1-3.3 | I-3 | 1000 | t.b.d. | t.b.d. |

The investigations described above are repeated at an addressing/measurement frequency of 3 Hz. The results are compiled in the following table, Table 1c.

TABLE 1c

| Ex. | Mixture | Stabiliser | c(stab.)/ ppm | VHR(t)/% @ 100° C., 3 Hz | |
|---|---|---|---|---|---|
| | | | | t = 0 h | t = 30 min |
| (Ref.) | M-1 | None | 0 | 28 | 19 |
| C1.1 | C-1-1.1 | R-1 | 100 | 38.7 | 34.0 |
| C1.2 | C-1-1.2 | R-1 | 500 | 36.6 | 34.3 |
| C1.3 | C-1-1.3 | R-1 | 1000 | 30.7 | 31.8 |
| M1.1.1 | M-1-1.1 | I-1 | 100 | 45.7 | 37.7 |
| M1.1.2 | M-1-1.2 | I-1 | 500 | 59.9 | 53.9 |
| M1.1.3 | M-1-1.3 | I-1 | 1000 | 60.5 | 52.8 |
| M1.2.1 | M-1-2.1 | I-2 | 100 | t.b.d. | t.b.d. |
| M1.2.2 | M-1-2.2 | I-2 | 500 | t.b.d. | t.b.d. |
| M1.2.3 | M-1-2.3 | I-2 | 1000 | t.b.d. | t.b.d. |
| M1.3.1 | M-1-3.1 | I-3 | 100 | t.b.d. | t.b.d. |
| M1.3.2 | M-1-3.2 | I-3 | 500 | t.b.d. | t.b.d. |
| M1.3.3 | M-1-3.3 | I-3 | 1000 | t.b.d. | t.b.d. |

The investigations are additionally repeated at a lower temperature, here at a temperature of 60° C. Addressing voltages/measurement frequencies of 3 Hz and 1 Hz are used here. The results are compiled in the two following tables, Table 1 d and Table 1e.

TABLE 1d

| Ex. | Mixture | Stabiliser | c(stab.)/ppm | VHR(t)/% @ 60° C., 3 Hz t = 0 h | t = 30 min |
|---|---|---|---|---|---|
| (Ref.) | M-1 | None | 0 | 66.3 | 45.8 |
| C1.1 | C-1-1.1 | R-1 | 100 | 87.0 | 76.3 |
| C1.2 | C-1-1.2 | R-1 | 500 | 86.2 | 78.4 |
| C1.3 | C-1-1.3 | R-1 | 1000 | 85.0 | 78.7 |
| M1.1.1 | M-1-1.1 | I-1 | 100 | 90.8 | 82.9 |
| M1.1.2 | M-1-1.2 | I-1 | 500 | 93.8 | 89.6 |
| M1.1.3 | M-1-1.3 | I-1 | 1000 | 92.3 | 88.7 |
| M1.2.1 | M-1-2.1 | I-2 | 100 | t.b.d. | t.b.d. |
| M1.2.2 | M-1-2.2 | I-2 | 500 | t.b.d. | t.b.d. |
| M1.2.3 | M-1-2.3 | I-2 | 1000 | t.b.d. | t.b.d. |
| M1.3.1 | M-1-3.1 | I-3 | 100 | t.b.d. | t.b.d. |
| M1.3.2 | M-1-3.2 | I-3 | 500 | t.b.d. | t.b.d. |
| M1.3.3 | M-1-3.3 | I-3 | 1000 | t.b.d. | t.b.d. |

TABLE 1e

| Ex. | Mixture | Stabiliser | c(stab.)/ppm | VHR(t)/% @ 60° C., 1 Hz t = 0 h | t = 30 min |
|---|---|---|---|---|---|
| (Ref.) | M-1 | None | 0 | 45.3 | 33.8 |
| C1.1 | C-1-1.1 | R-1 | 100 | 72.6 | 63.3 |
| C1.2 | C-1-1.2 | R-1 | 500 | 70.2 | 64.3 |
| C1.3 | C-1-1.3 | R-1 | 1000 | 65.8 | 63.3 |
| M1.1.1 | M-1-1.1 | I-1 | 100 | 81.3 | 74.1 |
| M1.1.2 | M-1-1.2 | I-1 | 500 | 86.6 | 82.3 |
| M1.1.3 | M-1-1.3 | I-1 | 1000 | 83.3 | 80.6 |
| M1.2.1 | M-1-2.1 | I-2 | 100 | t.b.d. | t.b.d. |
| M1.2.2 | M-1-2.2 | I-2 | 500 | t.b.d. | t.b.d. |
| M1.2.3 | M-1-2.3 | I-2 | 1000 | t.b.d. | t.b.d. |
| M1.3.1 | M-1-3.1 | I-3 | 100 | t.b.d. | t.b.d. |
| M1.3.2 | M-1-3.2 | I-3 | 500 | t.b.d. | t.b.d. |
| M1.3.3 | M-1-3.3 | I-3 | 1000 | t.b.d. | t.b.d. |

In addition, the mixtures are subjected to a test for exposure to a backlight. To this end, the stability of corresponding test cells having an alignment layer for planar alignment (PI: AL16301, as described above) and flat ITO electrodes to illumination with a cold cathode (CCFL) LCD backlight is investigated. To this end, corresponding test cells are filled and sealed. These cells are then exposed to illumination with a commercial LED backlight for LCDs for various times (48 h, 336 h and 1000 h). There is no additional heating, besides the heat generated by the backlight. The "voltage holding ratio" is then in each case determined after 5 minutes at a temperature of 100° C. The results are compiled in the following tables, Tables 2a to 2c.

TABLE 2a

| Ex. | Mixture | Stabiliser | c(stab.)/ppm | VHR(t)/% @ 100° C., 60 Hz t = 0 h | t = 48 h |
|---|---|---|---|---|---|
| (Ref.) | M-1 | None | 0 | 72.4 | 61.2 |
| C1.1 | C-1-1.1 | R-1 | 100 | 85.7 | 82.3 |
| C1.2 | C-1-1.2 | R-1 | 500 | 84.2 | 84.3 |
| C1.3 | C-1-1.3 | R-1 | 1000 | 83.7 | 84.5 |
| M1.1.1 | M-1-1.1 | I-1 | 100 | 90.5 | 89.7 |
| M1.1.2 | M-1-1.2 | I-1 | 500 | 93.7 | 92.9 |
| M1.1.3 | M-1-1.3 | I-1 | 1000 | 92.2 | 93.0 |
| M1.2.1 | M-1-2.1 | I-2 | 100 | 87.2 | 84.5 |
| M1.2.2 | M-1-2.2 | I-2 | 500 | 88.9 | 89.6 |
| M1.2.3 | M-1-2.3 | I-2 | 1000 | 89.4 | 89.2 |
| M1.3.1 | M-1-3.1 | I-3 | 100 | t.b.d. | t.b.d. |
| M1.3.2 | M-1-3.2 | I-3 | 500 | t.b.d. | t.b.d. |
| M1.3.3 | M-1-3.3 | I-3 | 1000 | t.b.d. | t.b.d. |

TABLE 2b

| Ex. | Mixture | Stabiliser | c(stab.)/ppm | VHR(t)/% @ 100° C., 60 Hz t = 0 h | t = 336 h |
|---|---|---|---|---|---|
| (Ref.) | M-1 | None | 0 | 72.4 | 53.9 |
| C1.1 | C-1-1.1 | R-1 | 100 | 85.7 | 72.6 |
| C1.2 | C-1-1.2 | R-1 | 500 | 84.2 | 79.7 |
| C1.3 | C-1-1.3 | R-1 | 1000 | 83.7 | 79.3 |
| M1.1.1 | M-1-1.1 | I-1 | 100 | 90.5 | 82.4 |
| M1.1.2 | M-1-1.2 | I-1 | 500 | 93.7 | 89.2 |
| M1.1.3 | M-1-1.3 | I-1 | 1000 | 92.2 | 90.5 |
| M1.2.1 | M-1-2.1 | I-2 | 100 | 87.2 | 80.9 |
| M1.2.2 | M-1-2.2 | I-2 | 500 | 88.9 | 86.2 |
| M1.2.3 | M-1-2.3 | I-2 | 1000 | 89.4 | 86.6 |
| M1.3.1 | M-1-3.1 | I-3 | 100 | t.b.d. | t.b.d. |
| M1.3.2 | M-1-3.2 | I-3 | 500 | t.b.d. | t.b.d. |
| M1.3.3 | M-1-3.3 | I-3 | 1000 | t.b.d. | t.b.d. |

TABLE 2c

| Ex. | Mixture | Stabiliser | c(stab.)/ppm | VHR(t)/% @ 100° C., 60 Hz t = 0 h | t = 1000 h |
|---|---|---|---|---|---|
| (Ref.) | M-1 | None | 0 | 72.4 | 53.6 |
| C1.1 | C-1-1.1 | R-1 | 100 | 85.7 | 69.6 |
| C1.2 | C-1-1.2 | R-1 | 500 | 84.2 | 78.0 |
| C1.3 | C-1-1.3 | R-1 | 1000 | 83.7 | 77.0 |
| M1.1.1 | M-1-1.1 | I-1 | 100 | 90.5 | 77.4 |
| M1.1.2 | M-1-1.2 | I-1 | 500 | 93.7 | 85.4 |
| M1.1.3 | M-1-1.3 | I-1 | 1000 | 92.2 | 87.5 |
| M1.2.1 | M-1-2.1 | I-2 | 100 | 87.2 | 76.6 |
| M1.2.2 | M-1-2.2 | I-2 | 500 | 88.9 | 83.4 |
| M1.2.3 | M-1-2.3 | I-2 | 1000 | 89.4 | 85.0 |
| M1.3.1 | M-1-3.1 | I-3 | 100 | t.b.d. | t.b.d. |
| M1.3.2 | M-1-3.2 | I-3 | 500 | t.b.d. | t.b.d. |
| M1.3.3 | M-1-3.3 | I-3 | 1000 | t.b.d. | t.b.d. |

In addition, the ion densities are determined for the mixtures. The results are compiled in the following table, Table 3.

The exposure is carried out in a commercial "UV/Suntest" instrument from Hereaus, Hanau. The irradiation is carried out using a Hoya lamp with a "cut-off" filter with a wavelength of 340 nm (i.e. T=50% at 340 nm). The spectral distribution of the radiation from this lamp is similar to the spectral distribution of natural sunlight. The irradiation intensity is 3 J/cm$^2$, measured using an appropriate detector at a wavelength of 365 nm. The irradiation is carried out at an ambient temperature of typically 20° C. for about ½ hour.

The ion density (ID for short) is determined in closed test cells. The test cells have, as described above, an alignment layer of the polyimide AL-16301. However, they have a layer thickness of 6.0 μm. The measurements are carried out at 3 V, 0.03 Hz and 60° C.

TABLE 3

| Ex. | Mixture | Stabiliser | c(stab.)/ ppm | Ion density/pC | |
|---|---|---|---|---|---|
| | | | | t = 0 h | t = 30 min, Suntest |
| (Ref.) | M-1 | None | 0 | 605 | 1519 |
| C1.1 | C-1-1.1 | R-1 | 100 | 238 | 458 |
| C1.2 | C-1-1.2 | R-1 | 500 | 261 | 438 |
| C1.3 | C-1-1.3 | R-1 | 1000 | 357 | 500 |
| M1.1.1 | M-1-1.1 | I-1 | 100 | 175 | 376 |
| M1.1.2 | M-1-1.2 | I-1 | 500 | 117 | 216 |
| M1.1.3 | M-1-1.3 | I-1 | 1000 | 106 | 205 |
| M1.2.1 | M-1-2.1 | I-2 | 100 | t.b.d. | t.b.d. |
| M1.2.2 | M-1-2.2 | I-2 | 500 | t.b.d. | t.b.d. |
| M1.2.3 | M-1-2.3 | I-2 | 1000 | t.b.d. | t.b.d. |
| M1.3.1 | M-1-3.1 | I-3 | 100 | t.b.d. | t.b.d. |
| M1.3.2 | M-1-3.2 | I-3 | 500 | t.b.d. | t.b.d. |
| M1.3.3 | M-1-3.3 | I-3 | 1000 | t.b.d. | t.b.d. |

It is readily evident here that compound I-1, even in relatively low concentrations, exhibits clearly stabilising properties which are clearly superior both to those of the starting mixture and also to those of the comparative mixture. In addition, the ion density is very greatly reduced compared with the undoped mixture.

The compounds of the formulae I-1 to I-3 have a stabilising activity which is superior to the comparative compound R-1 in all concentrations employed. This leads, inter alia, to a reduction in the risk of image sticking on exposure to the backlight.

Examples 2.1.1 to 2.3.3 and Corresponding Comparative Examples

The following mixture (M-2) is prepared and investigated.

| Mixture M-2 | | |
|---|---|---|
| Composition | | |
| Compound | | Concentration |
| No. | Abbreviation | /% by weight |
| 1 | CC-3-V | 32.0 |
| 2 | CC-3-V1 | 11.0 |
| 3 | CC-3-2V1 | 4.5 |
| 4 | PP-1-2V1 | 2.0 |
| 5 | CCP-3-OT | 7.5 |
| 6 | CCP-5-OT | 1.5 |
| 7 | DPGU-4-F | 5.0 |
| 8 | PUQU-3-F | 1.5 |
| 9 | APUQU-2-F | 7.0 |
| 10 | APUQU-3-F | 7.0 |
| 11 | PGUQU-3-F | 3.0 |
| 12 | PGUQU-4-F | 8.0 |
| 13 | PGUQU-5-F | 2.0 |
| 14 | DGUQU-4-F | 8.0 |
| Σ | | 100.0 |
| Physical properties | | |
| $T(N, I) =$ | | 85.0° C. |
| $n_e(20°\ C., 589\ nm) =$ | | 1.5865 |
| $\Delta n(20°\ C., 589\ nm) =$ | | 0.1089 |
| $\varepsilon_\parallel(20°, 1\ kHz) =$ | | 19.0 |
| $\Delta\varepsilon(20°, 1\ kHz) =$ | | 15.3 |
| $\gamma_1(20°\ C.) =$ | | 89 mPa·s |
| $k_{11}(20°\ C.) =$ | | 14.4 pN |
| $k_{33}(20°\ C.) =$ | | 15.1 pN |
| $V_0(20°\ C.) =$ | | t.b.d. V |
| $V_{10}(20°\ C.) =$ | | t.b.d. V |

Note:
t.b.d.: to be determined.

The corresponding compounds are added to mixture M-2, divided into several parts are described in Example 1 in the case of mixture M-1, and investigated as described therein. The results are compiled in the following tables.

TABLE 4a

| Ex. | Mixture | Stabiliser | c(stab.)/ ppm | VHR(t)/% @ 100° C., 60 Hz | |
|---|---|---|---|---|---|
| | | | | t = 0 h | t = 30 min |
| (Ref.) | C1 | None | 0 | 96.3 | 77.6 |
| C2.1 | C-2-1.1 | R-1 | 100 | 98.6 | 90.1 |
| C2.2 | C-2-1.2 | R-1 | 500 | 98.5 | 85.4 |
| C2.3 | C-2-1.3 | R-1 | 1000 | 98.3 | 85.1 |
| M2.1.1 | M-2-1.1 | I-1 | 100 | 99.0 | 91.8 |
| M2.1.2 | M-2-1.2 | I-1 | 500 | 99.2 | 91.5 |
| M2.1.3 | M-2-1.3 | I-1 | 1000 | 99.0 | 89.7 |
| M2.2.1 | M-2-2.1 | I-2 | 100 | 98.7 | 89.7 |
| M2.2.2 | M-2-2.2 | I-2 | 500 | 98.6 | 81.3 |
| M2.2.3 | M-2-2.3 | I-2 | 1000 | 98.4 | 74.4 |
| M2.3.1 | M-2-3.1 | I-3 | 100 | 97.1 | 90.5 |
| M2.3.2 | M-2-3.2 | I-3 | 500 | 98.0 | 88.4 |
| M2.3.3 | M-2-3.3 | I-3 | 1000 | 97.6 | 86.9 |
| M2.4.1 | M-2-4.1 | I-4 | 100 | 97.3 | 84.4 |
| M2.4.2 | M-2-4.2 | I-4 | 500 | 98.7 | 79.8 |
| M2.4.3 | M-2-4.3 | I-4 | 1000 | 98.8 | 72.7 |

It is readily evident here that compounds I-1 to I-4 and in particular I-1 to I-3 have clearly stabilising properties, even in relatively low concentrations.

Compound I-1 has an excellent stabilising activity in a concentration of 100 ppm. This leads to a reduction in the risk of image sticking on exposure to the backlight.

The investigations described above are repeated at an addressing/measurement frequency of 10 Hz. The results are compiled in the following table, Table 4b.

TABLE 4b

| Ex. | Mixture | Stabiliser | c(stab.)/ ppm | VHR(t)/% @ 100° C., 10 Hz | |
|---|---|---|---|---|---|
| | | | | t = 0 h | t = 30 min |
| (Ref.) | M-2 | None | 0 | 96.4 | 56.3 |
| C2.1 | C-2-1.1 | R-1 | 100 | t.b.d. | t.b.d. |
| C2.2 | C-2-1.2 | R-1 | 500 | t.b.d. | t.b.d. |
| C2.3 | C-2-1.3 | R-1 | 1000 | 97.7 | 58.5 |
| M2.1.1 | M-2-1.1 | I-1 | 100 | t.b.d. | t.b.d. |
| M2.1.2 | M-2-1.2 | I-1 | 500 | t.b.d. | t.b.d. |
| M2.1.3 | M-2-1.3 | I-1 | 1000 | 98.7 | 71.0 |
| M2.2.1 | M-2-2.1 | I-2 | 100 | t.b.d. | t.b.d. |
| M2.2.2 | M-2-2.2 | I-2 | 500 | t.b.d. | t.b.d. |
| M2.2.3 | M-2-2.3 | I-2 | 1000 | t.b.d. | t.b.d. |
| M2.3.1 | M-2-3.1 | I-3 | 100 | t.b.d. | t.b.d. |
| M2.3.2 | M-2-3.2 | I-3 | 500 | t.b.d. | t.b.d. |
| M2.3.3 | M-2-3.3 | I-3 | 1000 | t.b.d. | t.b.d. |
| M2.4.1 | M-2-3.1 | I-4 | 100 | t.b.d. | t.b.d. |
| M2.4.2 | M-2-3.2 | I-4 | 500 | t.b.d. | t.b.d. |
| M2.4.3 | M-2-3.3 | I-4 | 1000 | t.b.d. | t.b.d. |

The investigations described above are repeated at an addressing/measurement frequency of 3 Hz. The results are compiled in the following table, Table 4c.

TABLE 4c

| Ex. | Mixture | Stabiliser | c(stab.)/ppm | VHR(t)/% @ 100° C., 3 Hz t = 0 h | VHR(t)/% @ 100° C., 3 Hz t = 30 min |
|---|---|---|---|---|---|
| (Ref.) | M-2 | None | 0 | 96.4 | 43.3 |
| C2.1 | C-2-1.1 | R-1 | 100 | t.b.d. | t.b.d. |
| C2.2 | C-2-1.2 | R-1 | 500 | t.b.d. | t.b.d. |
| C2.3 | C-2-1.3 | R-1 | 1000 | 97.7 | 39.0 |
| M2.1.1 | M-2-1.1 | I-1 | 100 | t.b.d. | t.b.d. |
| M2.1.2 | M-2-1.2 | I-1 | 500 | t.b.d. | t.b.d. |
| M2.1.3 | M-2-1.3 | I-1 | 1000 | 98.7 | 51.8 |
| M2.2.1 | M-2-2.1 | I-2 | 100 | t.b.d. | t.b.d. |
| M2.2.2 | M-2-2.2 | I-2 | 500 | t.b.d. | t.b.d. |
| M2.2.3 | M-2-2.3 | I-2 | 1000 | t.b.d. | t.b.d. |
| M2.3.1 | M-2-3.1 | I-3 | 100 | t.b.d. | t.b.d. |
| M2.3.2 | M-2-3.2 | I-3 | 500 | t.b.d. | t.b.d. |
| M2.3.3 | M-2-3.3 | I-3 | 1000 | t.b.d. | t.b.d. |
| M2.4.1 | M-2-3.1 | I-4 | 100 | t.b.d. | t.b.d. |
| M2.4.2 | M-2-3.2 | I-4 | 500 | t.b.d. | t.b.d. |
| M2.4.3 | M-2-3.3 | I-4 | 1000 | t.b.d. | t.b.d. |

The investigations are additionally repeated at a temperature of 60° C. Addressing voltages/measurement frequencies of 3 Hz and 1 Hz are used here. The results are compiled in the two following tables, Table 4d and Table 4e.

In addition, the mixtures are subjected to a test for exposure to a backlight. To this end, the stability of corresponding test cells having an alignment layer for planar alignment (PI: AL16301, as described above) and flat ITO electrodes to illumination with a cold cathode (CCFL) LCD backlight is investigated. To this end, corresponding test cells are exposed to the illumination for various times (48 h, 336 h and 1000 h). The voltage holding ratio is then in each case determined after 5 minutes at the temperature of 100° C. The results are compiled in the following tables, Tables 5a to 5c.

TABLE 5a

| Ex. | Mixture | Stabiliser | c(stab.)/ppm | VHR(t)/% @ 100° C., 60 Hz t = 0 h | VHR(t)/% @ 100° C., 60 Hz t = 48 h |
|---|---|---|---|---|---|
| (Ref.) | M-2 | None | 0 | 95.4 | 79.6 |
| C2.1 | C-2-1.1 | R-1 | 100 | 98.1 | 95.7 |
| C2.2 | C-2-1.2 | R-1 | 500 | 97.7 | 96.3 |
| C2.3 | C-2-1.3 | R-1 | 1000 | 97.7 | 96.6 |
| M2.1.1 | M-2-1.1 | I-1 | 100 | 98.6 | 97.7 |
| M2.1.2 | M-2-1.2 | I-1 | 500 | 98.8 | 98.2 |
| M2.1.3 | M-2-1.3 | I-1 | 1000 | 98.8 | 98.0 |
| M2.2.1 | M-2-2.1 | I-2 | 100 | 98.2 | 97.2 |
| M2.2.2 | M-2-2.2 | I-2 | 500 | 98.2 | 96.7 |
| M2.2.3 | M-2-2.3 | I-2 | 1000 | 97.8 | 96.2 |
| M2.3.1 | M-2-3.1 | I-3 | 100 | t.b.d. | t.b.d. |
| M2.3.2 | M-2-3.2 | I-3 | 500 | t.b.d. | t.b.d. |
| M2.3.3 | M-2-3.3 | I-3 | 1000 | t.b.d. | t.b.d. |
| M2.4.1 | M-2-3.1 | I-4 | 100 | t.b.d. | t.b.d. |
| M2.4.2 | M-2-3.2 | I-4 | 500 | t.b.d. | t.b.d. |
| M2.4.3 | M-2-3.3 | I-4 | 1000 | t.b.d. | t.b.d. |

TABLE 5b

| Ex. | Mixture | Stabiliser | c(stab.)/ppm | VHR(t)/% @ 100° C., 60 Hz t = 0 h | VHR(t)/% @ 100° C., 60 Hz t = 336 h |
|---|---|---|---|---|---|
| (Ref.) | M-2 | None | 0 | 95.4 | 63.5 |
| C2.1 | C-2-1.1 | R-1 | 100 | 98.1 | 85.8 |
| C2.2 | C-2-1.2 | R-1 | 500 | 97.7 | 88.4 |
| C2.3 | C-2-1.3 | R-1 | 1000 | 97.7 | 90.5 |
| M2.1.1 | M-2-1.1 | I-1 | 100 | 98.6 | 92.0 |
| M2.1.2 | M-2-1.2 | I-1 | 500 | 98.8 | 94.9 |
| M2.1.3 | M-2-1.3 | I-1 | 1000 | 98.8 | 94.7 |
| M2.2.1 | M-2-2.1 | I-2 | 100 | 98.2 | 90.9 |
| M2.2.2 | M-2-2.2 | I-2 | 500 | 98.2 | 90.5 |
| M2.2.3 | M-2-2.3 | I-2 | 1000 | 97.8 | 89.6 |
| M2.3.1 | M-2-3.1 | I-3 | 100 | t.b.d. | t.b.d. |
| M2.3.2 | M-2-3.2 | I-3 | 500 | t.b.d. | t.b.d. |
| M2.3.3 | M-2-3.3 | I-3 | 1000 | t.b.d. | t.b.d. |
| M2.4.1 | M-2-3.1 | I-4 | 100 | t.b.d. | t.b.d. |
| M2.4.2 | M-2-3.2 | I-4 | 500 | t.b.d. | t.b.d. |
| M2.4.3 | M-2-3.3 | I-4 | 1000 | t.b.d. | t.b.d. |

TABLE 5c

| Ex. | Mixture | Stabiliser | c(stab.)/ppm | VHR(t)/% @ 100° C., 60 Hz t = 0 h | VHR(t)/% @ 100° C., 60 Hz t = 1000 h |
|---|---|---|---|---|---|
| (Ref.) | M-2 | None | 0 | 95.4 | 58.6 |
| C2.1 | C-2-1.1 | R-1 | 100 | 98.1 | 73.9 |
| C2.2 | C-2-1.2 | R-1 | 500 | 97.7 | 77.3 |
| C2.3 | C-2-1.3 | R-1 | 1000 | 97.7 | 83.3 |
| M2.1.1 | M-2-1.1 | I-1 | 100 | 98.6 | 83.8 |
| M2.1.2 | M-2-1.2 | I-1 | 500 | 98.8 | 88.5 |
| M2.1.3 | M-2-1.3 | I-1 | 1000 | 98.8 | 89.1 |
| M2.2.1 | M-2-2.1 | I-2 | 100 | 98.2 | 80.1 |
| M2.2.2 | M-2-2.2 | I-2 | 500 | 98.2 | 83.3 |
| M2.2.3 | M-2-2.3 | I-2 | 1000 | 97.8 | 84.4 |
| M2.3.1 | M-2-3.1 | I-3 | 100 | t.b.d. | t.b.d. |
| M2.3.2 | M-2-3.2 | I-3 | 500 | t.b.d. | t.b.d. |
| M2.3.3 | M-2-3.3 | I-3 | 1000 | t.b.d. | t.b.d. |
| M2.4.1 | M-2-3.1 | I-4 | 100 | t.b.d. | t.b.d. |
| M2.4.2 | M-2-3.2 | I-4 | 500 | t.b.d. | t.b.d. |
| M2.4.3 | M-2-3.3 | I-4 | 1000 | t.b.d. | t.b.d. |

As can be seen from Table 5, even a low concentration of compounds I-1 and I-2 leads to a considerable improvement in the final value of the VHR after exposure to light from an LCD backlight.

In addition, the ion densities are determined for the mixtures. The results are compiled in the following table, Table 6.

TABLE 6

| Ex. | Mixture | Stabiliser | c(stab.)/ppm | Ion density/pC t = 0 h | Ion density/pC t = 30 min, Suntest |
|---|---|---|---|---|---|
| (Ref.) | M-2 | None | 0 | 152 | 681 |
| C2.1 | C-2-1.1 | R-1 | 100 | 57 | 275 |
| C2.2 | C-2-1.2 | R-1 | 500 | 40 | 449 |
| C2.3 | C-2-1.3 | R-1 | 1000 | 43 | 579 |
| M2.1.1 | M-2-1.1 | I-1 | 100 | 37 | 193 |
| M2.1.2 | M-2-1.2 | I-1 | 500 | 21 | 217 |
| M2.1.3 | M-2-1.3 | I-1 | 1000 | 23 | 254 |
| M2.2.1 | M-2-2.1 | I-2 | 100 | 37 | 233 |
| M2.2.2 | M-2-2.2 | I-2 | 500 | 39 | 433 |
| M2.2.3 | M-2-2.3 | I-2 | 1000 | 43 | 634 |
| M2.3.1 | M-2-3.1 | I-3 | 100 | t.b.d. | t.b.d. |
| M2.3.2 | M-2-3.2 | I-3 | 500 | t.b.d. | t.b.d. |
| M2.3.3 | M-2-3.3 | I-3 | 1000 | t.b.d. | t.b.d. |
| M2.4.1 | M-2-3.1 | I-4 | 100 | t.b.d. | t.b.d. |
| M2.4.2 | M-2-3.2 | I-4 | 500 | t.b.d. | t.b.d. |
| M2.4.3 | M-2-3.3 | I-4 | 1000 | t.b.d. | t.b.d. |

It is readily evident here that the compound of the formula I-1, even in relatively low concentrations, exhibits clearly stabilising properties which are clearly superior both to those of the starting mixture and also to those of the comparative mixture. In addition, the ion density is very greatly reduced compared with the undoped mixture.

In addition, the VHR values are determined for the mixtures after heating in test cells for 120 hours. The closed test cells are stored here in an oven at a temperature of 100° C. for the times indicated.

The results are compiled in the following table, Table 7.

TABLE 7

| Ex. | Mixture | Stabiliser | c(stab.)/ ppm | VHR(t)/% @ 100° C., 60 Hz | |
|---|---|---|---|---|---|
| | | | | t = 0 h | t = 120 h |
| (Ref.) | M-2 | None | 0 | 96.3 | 91.1 |
| C2.1 | C-2-1.1 | R-1 | 100 | 97.7 | 90.2 |
| C2.2 | C-2-1.2 | R-1 | 500 | 98.5 | 94.0 |
| C2.3 | C-2-1.3 | R-1 | 1000 | 97.8 | 84.9 |
| M2.1.1 | M-2-1.1 | I-1 | 100 | 98.7 | 93.1 |
| M2.1.2 | M-2-1.2 | I-1 | 500 | 99.1 | 94.0 |
| M2.1.3 | M-2-1.3 | I-1 | 1000 | 99.1 | 92.9 |
| M2.2.1 | M-2-2.1 | I-2 | 100 | t.b.d. | t.b.d. |
| M2.2.2 | M-2-2.2 | I-2 | 500 | t.b.d. | t.b.d. |
| M2.2.3 | M-2-2.3 | I-2 | 1000 | t.b.d. | t.b.d. |
| M2.3.1 | M-2-3.1 | I-3 | 100 | t.b.d. | t.b.d. |
| M2.3.2 | M-2-3.2 | I-3 | 500 | t.b.d. | t.b.d. |
| M2.3.3 | M-2-3.3 | I-3 | 1000 | t.b.d. | t.b.d. |
| M2.4.1 | M-2-3.1 | I-4 | 100 | t.b.d. | t.b.d. |
| M2.4.2 | M-2-3.2 | I-4 | 500 | t.b.d. | t.b.d. |
| M2.4.3 | M-2-3.3 | I-4 | 1000 | t.b.d. | t.b.d. |

In addition, the ion densities are determined for the mixtures. The results are compiled in the following table, Table 8.

The exposure is carried out, as described above, in a commercial "UV/Suntest" instrument from Hereaus, Hanau. The irradiation is carried out using a Hoya lamp with a "cut-off" filter with a wavelength of 340 nm (i.e. T=50% at 340 nm). The spectral distribution of the radiation from this lamp is similar to the spectral distribution of natural sunlight. The irradiation intensity is 3 J/cm², measured using an appropriate detector at a wavelength of 365 nm. The irradiation is carried out at an ambient temperature of typically 20° C. for about ½ hour.

The ion density (ID for short) is determined in closed test cells. The test cells have, like those described above, an alignment layer of the polyimide AL-16301. However, they have a layer thickness of 5.5 μm. The measurements are carried out at 3 V, 0.03 Hz and 60° C.

TABLE 8

| Ex. | Mixture | Stabiliser | c(stab.)/ ppm | Ion density/pC | |
|---|---|---|---|---|---|
| | | | | t = 0 h | t = 30 min, Suntest |
| (Ref.) | M-2 | None | 0 | 152 | 681 |
| C2.1 | C-2-1.1 | R-1 | 100 | 57 | 275 |
| C2.2 | C-2-1.2 | R-1 | 500 | 40 | 449 |
| C2.3 | C-2-1.3 | R-1 | 1000 | 43 | 579 |
| M2.1.1 | M-2-1.1 | I-1 | 100 | 37 | 193 |
| M2.1.2 | M-2-1.2 | I-1 | 500 | 21 | 217 |
| M2.1.3 | M-2-1.3 | I-1 | 1000 | 23 | 254 |
| M2.2.1 | M-2-2.1 | I-2 | 100 | 37 | 233 |
| M2.2.2 | M-2-2.2 | I-2 | 500 | 39 | 433 |
| M2.2.3 | M-2-2.3 | I-2 | 1000 | 43 | 634 |
| M2.3.1 | M-2-3.1 | I-3 | 100 | t.b.d. | t.b.d. |
| M2.3.2 | M-2-3.2 | I-3 | 500 | t.b.d. | t.b.d. |
| M2.3.3 | M-2-3.3 | I-3 | 1000 | t.b.d. | t.b.d. |
| M2.4.1 | M-2-3.1 | I-4 | 100 | t.b.d. | t.b.d. |
| M2.4.2 | M-2-3.2 | I-4 | 500 | t.b.d. | t.b.d. |
| M2.4.3 | M-2-3.3 | I-4 | 1000 | t.b.d. | t.b.d. |

Examples 3.1.1 to 3.3.3

The following mixture (M-3) is prepared and investigated.

| Mixture M-3 | | |
|---|---|---|
| Composition | | |
| Compound | | Concentration |
| No. | Abbreviation | /% by weight |
| 1 | CY-3-O2 | 12.0 |
| 2 | CY-3-O4 | 2.0 |
| 3 | CY-5-O2 | 12.0 |
| 4 | CCY-3-O1 | 6.0 |
| 5 | CCY-3-O2 | 8.0 |
| 6 | CCY-4-O2 | 8.0 |
| 7 | CPY-2-O2 | 9.0 |
| 8 | CPY-3-O2 | 9.0 |
| 9 | PYP-2-3 | 5.0 |
| 10 | CC-3-V1 | 5.0 |
| 11 | CC-3-V | 19.0 |
| 12 | CPP-3-2 | 5.0 |
| Σ | | 100.0 |
| Physical properties | | |
| T(N, I) = | | 86.5° C. |
| $n_e$(20° C., 589 nm) = | | 1.5924 |
| $\Delta n$(20° C., 589 nm) = | | 0.1092 |
| $\varepsilon_\perp$(20°, 1 kHz) = | | 7.9 |
| $\Delta\varepsilon$(20°, 1 kHz) = | | −4.2 |
| $\gamma_1$(20° C.) = | | 155 mPa·s |
| $k_{11}$(20° C.) = | | 14.6 pN |
| $k_{33}$(20° C.) = | | 16.6 pN |
| $V_0$(20° C.) = | | 2.08 V |

Mixture M-3 is divided into several parts and investigated as described in the case of Example 1.

Firstly, the stability of the voltage holding ratio of mixture (M-3) itself is determined. The stability of mixture M-3 to UV exposure is investigated in a test cell having an alignment material for planar alignment and flat ITO electrodes. To this end, corresponding test cells are irradiated in the Suntest for 30 min. The voltage holding ratio is then determined in each case after 5 minutes at a temperature of 100° C. The results are compiled below, in Table 9. Here, as below, six test cells are filled and investigated for each individual mixture. The values indicated are the mean of the six individual values.

Next, 300 ppm of compound R-1 (C-3-1) are added to the remaining three parts of mixture M-3, and 100 ppm, 300 ppm and 600 ppm concentrations of compounds I-1 to I-3 are in each case added to further sets of in each case three parts of mixture M-3, and the stability of the resultant mixtures (C-3-1 and M-3-1.1 to M-3-3.3) is investigated as described above. The results are shown in Table 9 below.

The relative deviations of the voltage holding ratio values in various measurement series is typically in the range from about 3 to 4%.

TABLE 9

| Ex. | Mixture | Stabiliser | c(stab.)/ ppm | VHR(t)/% @ 100° C., 60 Hz t = 0 h | t = 30 min |
|---|---|---|---|---|---|
| (Ref.) | M-3 | None | 0 | 60.6 ± 1.2 | 57.1 ± 0.9 |
| C3.1 | C-3-1 | R-1 | 300 | 70.3 ± 1.1 | 72.7 ± 0.8 |
| M3.1.1 | M-3-1.1 | I-1 | 100 | 88.2 ± 1.2 | 83.0 ± 0.7 |
| M3.1.2 | M-3-1.2 | I-1 | 300 | 90.7 ± 1.4 | 86.5 ± 0.8 |
| M3.1.3 | M-3-1.3 | I-1 | 600 | 90.0 ± 0.6 | 88.5 ± 0.4 |
| M3.2.1 | M-3-2.1 | I-2 | 100 | 85.6 ± 1.6 | 79.9 ± 1.6 |
| M3.2.2 | M-3-2.2 | I-2 | 300 | 82.6 ± 0.7 | 81.4 ± 0.9 |
| M3.2.3 | M-3-2.3 | I-2 | 600 | 81.8 ± 1.0 | 79.7 ± 0.9 |
| M3.3.1 | M-3-3.1 | I-3 | 100 | 79.9 ± 1.2 | 75.2 ± 1.2 |
| M3.3.2 | M-3-3.2 | I-3 | 300 | 86.2 ± 2.0 | 84.1 ± 1.3 |
| M3.3.3 | M-3-3.3 | I-3 | 600 | 84.3 ± 2.1 | 85.9 ± 1.5 |

Examples 4.1.1 to 4.2.2

The following mixture (M-4) is prepared and investigated.

Mixture M-4

Composition

| No. | Compound Abbreviation | Concentration /% by weight |
|---|---|---|
| 1 | CPP-3-2 | 4.5 |
| 2 | CC-3-V | 23.5 |
| 3 | CCH-301 | 4.0 |
| 4 | CCY-3-O2 | 4.0 |
| 5 | CCY-3-O3 | 7.0 |
| 6 | CCY-4-O2 | 8.0 |
| 7 | CLY-3-O2 | 8.0 |
| 8 | CPY-2-O2 | 7.0 |
| 9 | CPY-3-O2 | 11.0 |
| 10 | CY-3-O2 | 11.0 |
| 11 | PY-3-O2 | 12.0 |
| Σ | | 100.0 |

Physical properties

| T(N, I) = | 86° C. |
|---|---|
| $n_e(20° C., 589 nm)$ = | 1.5962 |
| $\Delta n(20° C., 589 nm)$ = | 0.1118 |
| $\varepsilon_\perp(20°, 1 kHz)$ = | 8.0 |
| $\Delta\varepsilon(20°, 1 kHz)$ = | -4.3 |
| $\gamma_1(20° C.)$ = | 143 mPa·s |
| $k_{11}(20° C.)$ = | 15.0 pN |
| $k_{33}(20° C.)$ = | 16.7 pN |
| $V_0(20° C.)$ = | 2.08 V |

Mixture M-4 is divided into several parts. Firstly, the stability of the voltage holding ratio of mixture (M-4) itself is determined. The stability of mixture M-4 to exposure to an LCD backlight is investigated as described above in a test cell having an alignment material for planar alignment and flat ITO electrodes. To this end, corresponding test cells are irradiated with an LCD backlight for 30 min. The voltage holding ratio is then in each case determined after 5 minutes at a temperature of 100° C. The results are compiled below, in Table 10. Here, as below, six test cells are filled and investigated for each individual mixture. The values indicated are the mean of the six individual values.

500 ppm of compound R-1 are then added to one part of mixture M-4 (mixture C-4-1) and 500 ppm or 1000 ppm of compound I-2 or 500 ppm of compound I-3 are added to each of three further parts of mixture M-4, and the stability of all mixtures to exposure to the LCD backlight is investigated analogously to the procedure described in Examples 1 to 3 in test cells, here with alignment layer SE5811 from Nissan Chemicals, Japan. The results of the VHR measurements after irradiation for 500 hours are compiled in Table 10.

TABLE 10

| Ex. | Mixture | Stabiliser | c(stab.)/ ppm | VHR(t)/% @ 100° C., 60 Hz t = 0 h | t = 500 h |
|---|---|---|---|---|---|
| (Ref.) | M-4 | None | 0 | 65.7 ± 2.5 | 51.8 ± 3.0 |
| C4.1 | C-4-1 | R-1 | 500 | 58.9 ± 2.0 | 62.0 ± 2.0 |
| M4.1.1 | M-4-1.1 | I-1 | 500 | 70.6 ± 3.0 | 74.6 ± 1.9 |
| M4.1.2 | M-4-1.2 | I-1 | 1000 | 69.4 ± 1.7 | 72.9 ± 3.1 |
| M4.2.1 | M-4-2.1 | I-3 | 500 | 70.0 ± 1.6 | 73.9 ± 1.7 |
| M4.2.2 | M-4-2.2 | I-3 | 1000 | t.b.d. | t.b.d. |

Note:
t.b.d.: to be determined.

As can be seen from Table 10, even a low concentration of compounds I-1 and I-3 leads to a considerable improvement in the final value of the VHR after the exposure.

Examples 5.1 to 5.3

The following mixture (M-5) is prepared and investigated.

Mixture M-5

Composition

| No. | Compound Abbreviation | Concentration /% by weight |
|---|---|---|
| 1 | CY-3-O2 | 12.0 |
| 2 | CY-5-O2 | 10.5 |
| 3 | CCY-3-O1 | 6.0 |
| 4 | CCY-3-O2 | 7.0 |
| 5 | CCY-5-O2 | 5.0 |
| 6 | CPY-2-O2 | 12.0 |
| 7 | CPY-3-O2 | 12.0 |
| 8 | PYP-2-3 | 7.5 |
| 9 | CC-3-V1 | 4.0 |
| 10 | CC-3-V | 24.0 |
| Σ | | 100.0 |

Physical properties

| T(N, I) = | 85.0° C. |
|---|---|
| $n_e(20° C., 589 nm)$ = | 1.5956 |
| $\Delta n(20° C., 589 nm)$ = | 0.112 |
| $\varepsilon_\perp(20°, 1 kHz)$ = | 7.9 |
| $\Delta\varepsilon(20°, 1 kHz)$ = | -4.2 |
| $\gamma_1(20° C.)$ = | 145 mPa·s |
| $k_{11}(20° C.)$ = | 14.2 pN |
| $k_{33}(20° C.)$ = | 16.7 pN |
| $V_0(20° C.)$ = | 2.08 V |

As described in Example 4, mixture M-5 is also divided into several parts, and its stability to exposure to an LCD backlight is investigated as such and with various added compounds in a test cell having an alignment material for planar alignment and flat ITO electrodes.

TABLE 11

| Ex. | Mixture | Stabiliser | c(stab.)/ ppm | VHR(t)/% @ 100° C., 60 Hz t = 0 h | VHR(t)/% @ 100° C., 60 Hz t = 500 h |
|---|---|---|---|---|---|
| (Ref.) | M-5 | None | 0 | 88.5 ± 1.0 | 73.4 ± 1.2 |
| C5.1 | C-5-1 | R-1 | 300 | t.b.d. | t.b.d. |
| M5.1 | M-5-1 | I-1 | 300 | 88.8 ± 0.9 | 84.2 ± 2.2 |
| M5.2 | M-5-2 | I-2 | 300 | t.b.d. | t.b.d. |
| M5.3 | M-5-2 | I-3 | 300 | t.b.d. | t.b.d. |

Note:
t.b.d.: to be determined.

As can be seen from Table 11, even a low concentration of compound I-1 leads to a considerable improvement in the final value of the VHR after exposure to a backlight, both compared with the unstabilised reference mixture.

Examples 6.1 to 6.3

The following mixture (M-6) is prepared and investigated.

| Mixture M-6 | | |
|---|---|---|
| Composition | | |
| Compound | | Concentration |
| No. | Abbreviation | /% by weight |
| 1 | B-2O-O5 | 4.0 |
| 2 | CY-3-O2 | 12.0 |
| 3 | CCH-34 | 2.5 |
| 4 | CCP-V-1 | 1.5 |
| 5 | CCY-3-O2 | 10.0 |
| 6 | CCY-5-O2 | 2.0 |
| 7 | CLY-3-O2 | 8.0 |
| 8 | CPY-2-O2 | 6.0 |
| 9 | CPY-3-O2 | 10.0 |
| 10 | PGIY-2-O4 | 4.0 |
| 11 | CC-3-V | 30.0 |
| 12 | CC-3-V1 | 10.0 |
| Σ | | 100.0 |
| Physical properties | | |
| T(N, I) = | | 87.0° C. |
| $n_e$(20° C., 589 nm) = | | 1.5829 |
| $\Delta n$(20° C., 589 nm) = | | 0.1019 |
| $\varepsilon_\perp$(20°, 1 kHz) = | | 7.1 |
| $\Delta\varepsilon$(20°, 1 kHz) = | | −3.7 |
| $\gamma_1$(20° C.) = | | 112 mPa · s |
| $k_{11}$(20° C.) = | | 15.2 pN |
| $k_{33}$(20° C.) = | | 18.0 pN |

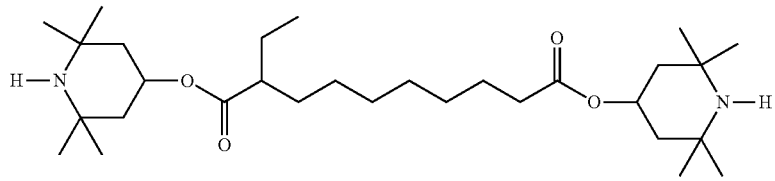

Compound R-2 as reference substance and, for comparison, compound I-9

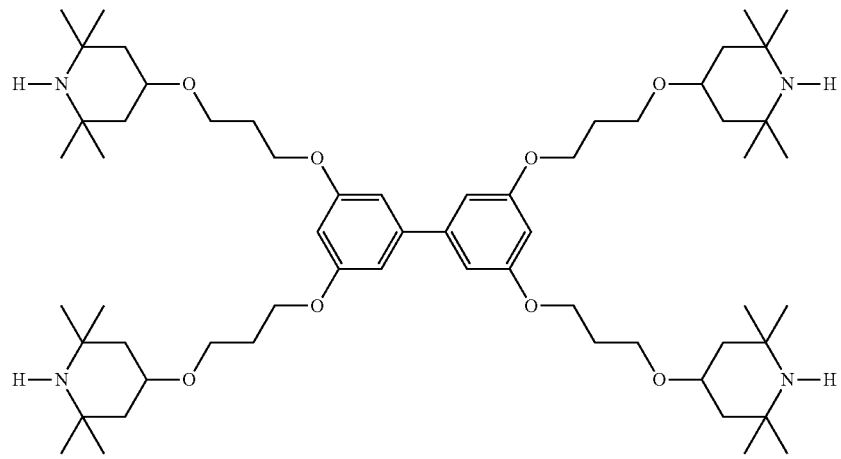

are added to this mixture. The results for test cells having the alignment layer AL-16301 are compiled in the following tables.

TABLE 12a

| Ex. | Mixture | Stabiliser | c(stab.)/ ppm | VHR(t)/% @ 60° C., 60 Hz t = 0 h | t = 30 min |
|---|---|---|---|---|---|
| (Ref.) | M-6 | None | 0 | 96.2 | 89.1 |
| C6.1 | C-6-1 | R-2 | 100 | 98.8 | 97.5 |
| C6.2 | C-6-2 | R-2 | 500 | 98.7 | 97.8 |
| C6.3 | C-6-3 | R-2 | 1000 | 98.5 | 98.0 |
| M6.1 | M-6-1 | I-4 | 100 | 98.1 | 94.9 |
| M6.2 | M-6-2 | I-4 | 500 | 99.6 | 99.4 |
| M6.3 | M-6-3 | I-4 | 1000 | 99.5 | 99.2 |

TABLE 12b

| Ex. | Mixture | Stabiliser | c(stab.)/ ppm | VHR(t)/% @ 60° C., 1 Hz t = 0 h | t = 30 min |
|---|---|---|---|---|---|
| (Ref.) | M-6 | None | 0 | 58.5 | 35.4 |
| C6.1 | C-6-1 | R-2 | 100 | 69.8 | 65.0 |
| C6.2 | C-6-2 | R-2 | 500 | 63.9 | 62.8 |
| C6.3 | C-6-3 | R-2 | 1000 | 60.9 | 61.5 |
| M6.1 | M-6-1 | I-9 | 100 | 73.2 | 51.9 |
| M6.2 | M-6-2 | I-9 | 500 | 91.5 | 87.5 |
| M6.3 | M-6-3 | I-9 | 1000 | 90.4 | 85.9 |

TABLE 12c

| Ex. | Mixture | Stabiliser | c(stab.)/ ppm | VHR(t)/% @ 100° C., 60 Hz t = 0 h | t = 30 min |
|---|---|---|---|---|---|
| (Ref.) | M-6 | None | 0 | 68.6 | 51.4 |
| C6.1 | C-6-1 | R-2 | 100 | 78.1 | 75.2 |
| C6.2 | C-6-2 | R-2 | 500 | 79.8 | 76.5 |
| C6.3 | C-6-3 | R-2 | 1000 | 79.3 | 77.4 |
| M6.1 | M-6-1 | I-9 | 100 | 83.4 ± . . . | 76.2 ± . . . |
| M6.2 | M-6-2 | I-9 | 500 | 93.1 ± . . . | 92.9 ± . . . |
| M6.3 | M-6-3 | I-9 | 1000 | 94.6 ± . . . | 93.6 ± . . . |

TABLE 12d

| Ex. | Mixture | Stabiliser | c(stab.)/ ppm | VHR(t)/% @ 100° C., 3 Hz t = 0 h | t = 30 min |
|---|---|---|---|---|---|
| (Ref.) | M-6 | None | 0 | 23.7 | 17.3 |
| C6.1 | C-6-1 | R-2 | 100 | 27.5 | 28.0 |
| C6.2 | C-6-2 | R-2 | 500 | 27.8 | 27.6 |
| C6.3 | C-6-3 | R-2 | 1000 | 26.3 | 26.9 |
| M6.1 | M-6-1 | I-9 | 100 | 35.0 | 30.7 |
| M6.2 | M-6-2 | I-9 | 500 | 55.5 | 56.0 |
| M6.3 | M-6-3 | I-9 | 1000 | 61.3 | 56.7 |

TABLE 12e

| Ex. | Mixture | Stabiliser | c(stab.)/ ppm | VHR(t)/% @ 100° C., 60 Hz t = 0 h | t = 48 h |
|---|---|---|---|---|---|
| (Ref.) | M-6 | None | 0 | 71.8 | 61.8 |
| C6.1 | C-6-1 | R-2 | 100 | 81.2 | 79.0 |
| C6.2 | C-6-2 | R-2 | 500 | 80.7 | 81.3 |
| C6.3 | C-6-3 | R-2 | 1000 | 79.3 | 81.4 |
| M6.1 | M-6-1 | I-9 | 100 | 86.2 | 81.9 |
| M6.2 | M-6-2 | I-9 | 500 | 94.4 | 94.5 |
| M6.3 | M-6-3 | I-9 | 1000 | 93.5 | 94.0 |

TABLE 12f

| Ex. | Mixture | Stabiliser | c(stab.)/ ppm | VHR(t)/% @ 100° C., 60 Hz t = 0 h | t = 360 h |
|---|---|---|---|---|---|
| (Ref.) | M-6 | None | 0 | 71.8 | 52.6 |
| C6.1 | C-6-1 | R-2 | 100 | 81.2 | 73.5 |
| C6.2 | C-6-2 | R-2 | 500 | 80.7 | 78.8 |
| C6.3 | C-6-3 | R-2 | 1000 | 79.3 | 80.1 |
| M6.1 | M-6-1 | I-9 | 100 | 86.2 | 84.2 |
| M6.2 | M-6-2 | I-9 | 500 | 94.4 | 92.4 |
| M6.3 | M-6-3 | I-9 | 1000 | 93.5 | 91.7 |

TABLE 12g

| Ex. | Mixture | Stabiliser | c(stab.)/ ppm | VHR(t)/% @ 100° C., 60 Hz t = 0 h | t = 1.000 h |
|---|---|---|---|---|---|
| (Ref.) | M-6 | None | 0 | 71.8 | 52.7 |
| C6.1 | C-6-1 | R-2 | 100 | 81.2 | 72.1 |
| C6.2 | C-6-2 | R-2 | 500 | 80.7 | 77.2 |
| C6.3 | C-6-3 | R-2 | 1000 | 79.3 | 78.7 |
| M6.1 | M-6-1 | I-9 | 100 | 86.2 | 80.6 |
| M6.2 | M-6-2 | I-9 | 500 | 94.4 | 83.6 |
| M6.3 | M-6-3 | I-9 | 1000 | 93.5 | 80.8 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A liquid crystalline medium comprising
   a. one or more compounds of the formulae I-9, I-10 or I-11

I-9
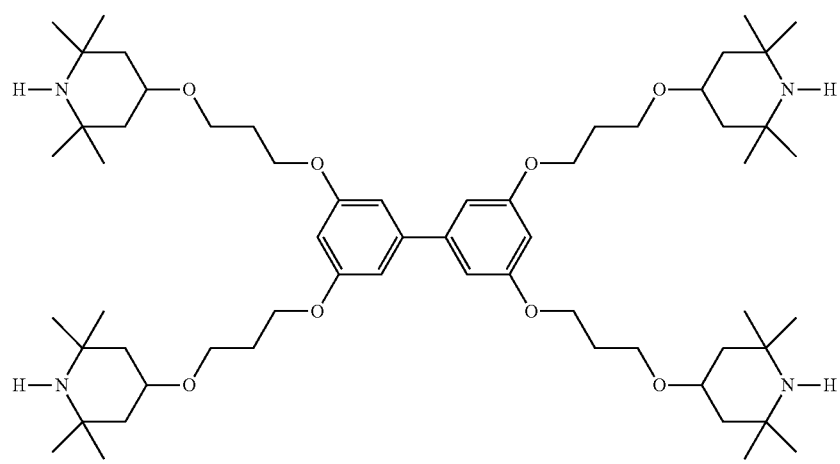
I-10
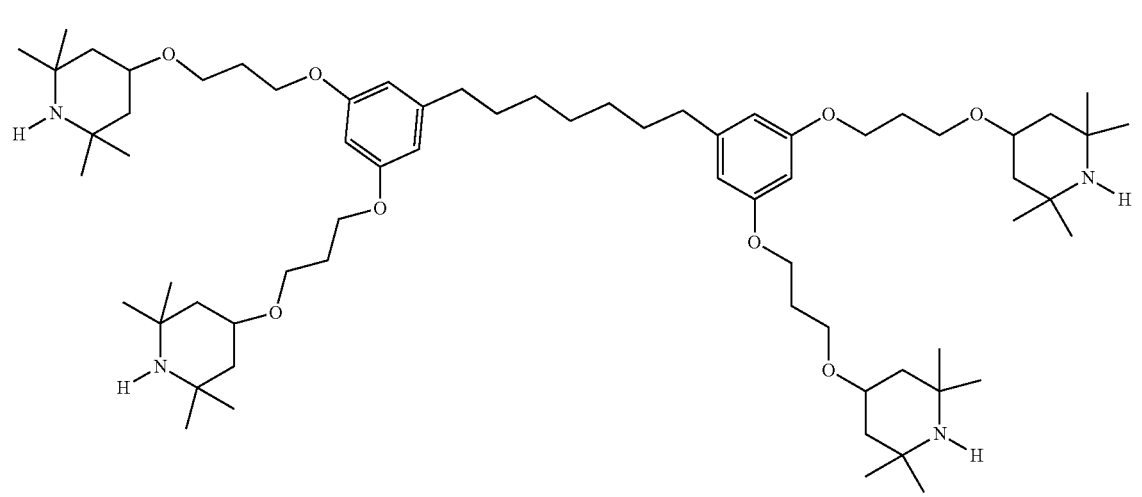
I-11
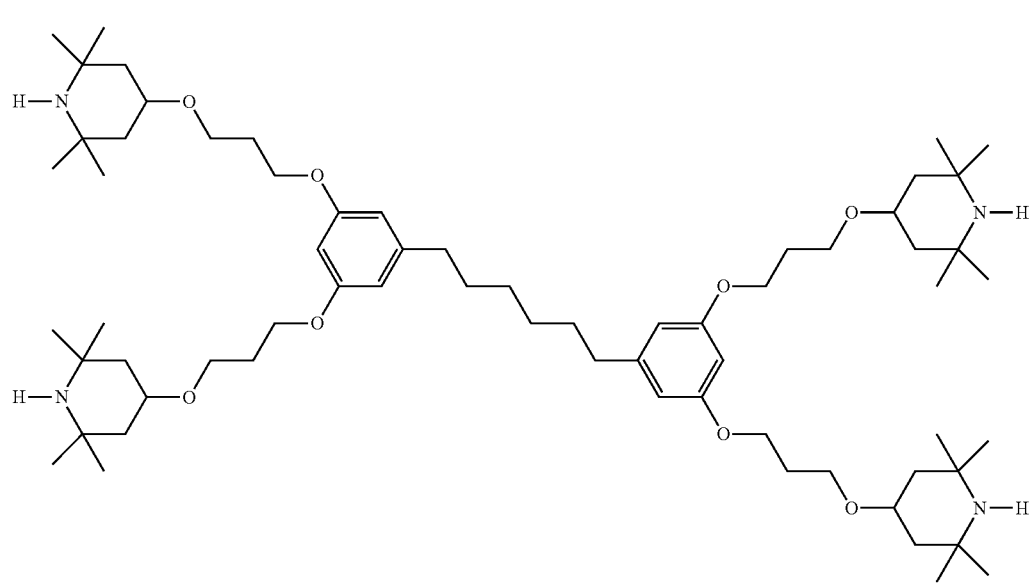
2. A medium according to claim 1, wherein the total concentration of the one or more compounds of the formulae I-9, I-10 or I-11 in the medium as a whole is from 1 ppm to 2500 ppm.

3. A medium according to claim 1, which further comprises a compound of the formula II

II in which
$R^{22}$ denotes an unsubstituted alkenyl radical having 2 to 7 C atoms
and $R^{21}$ denotes n-propyl and $R^{22}$ denotes vinyl.

4. A medium according to claim 3, wherein the total concentration of the compounds of the formula II in the medium as a whole is from 25% to 45%.

5. A medium according to claim 1, which further comprises one or more compounds of the formula III-4

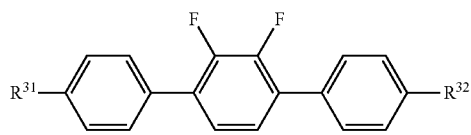

III-4 in which
$R^{31}$ denotes an unsubstituted alkyl radical having 1 to 7 C atoms,
$R^{32}$ denotes an unsubstituted alkyl radical having 1 to 7 C atoms or an unsubstituted alkoxy radical having 1 to 6 C atoms.

6. A medium according to claim 1, which additionally comprises one or more chiral compounds.

7. A compound of the formulae I-9, I-10 or I-11

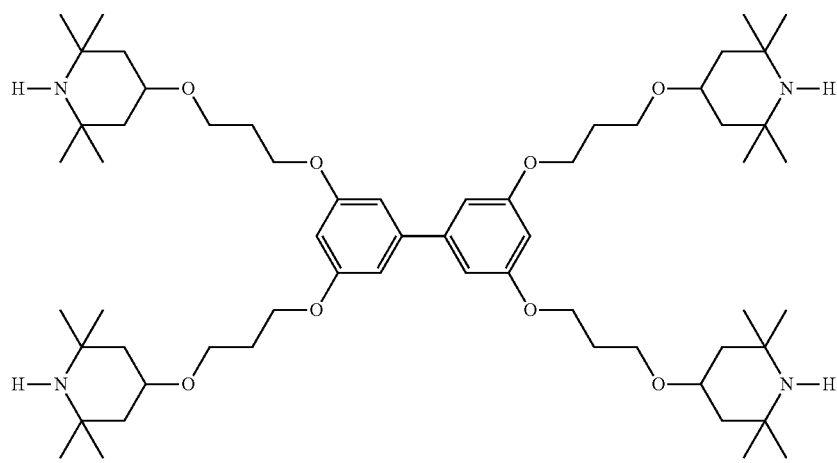 [SMILES: CC1(C)CC(OCCCOc2cc(OCCCOC3CC(C)(C)NC(C)(C)C3)cc(-c3cc(OCCCOC4CC(C)(C)NC(C)(C)C4)cc(OCCCOC4CC(C)(C)NC(C)(C)C4)c3)c2)CC(C)(C)N1]

I-9

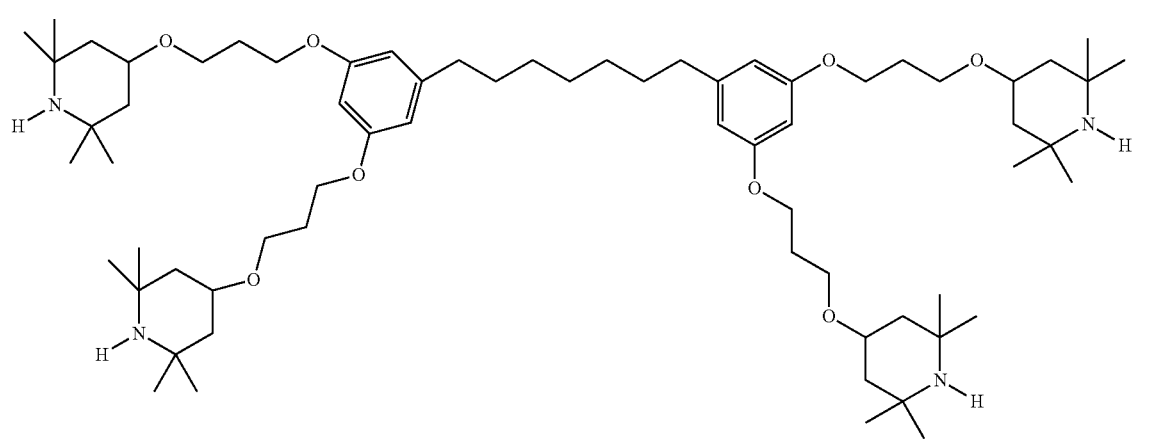

I-10

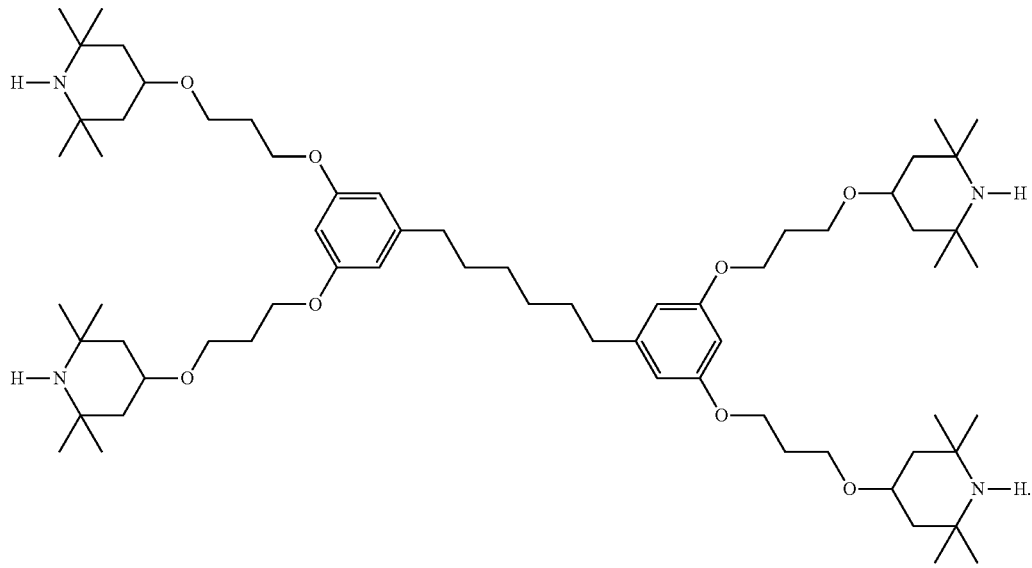
I-11

8. An electro-optical display electro-optical component, which contains a liquid-crystalline medium according to claim 1.

9. A display according to claim 8, which utilize a IPS, FFS, VA or ECB effect.

10. A display according to claim 8, which contains an active-matrix addressing device.

11. A method which comprises including a compound of claim 7 in a liquid-crystalline medium.

12. A method which comprises including a liquid-crystalline medium according to claim 1 in an electro-optical display or in an electro-optical component.

13. A process for the preparation of a liquid-crystalline medium according to claim 1, comprising mixing one or more compounds of the formulae I-9, I-10 or I-11 with one or more compounds of the formula B

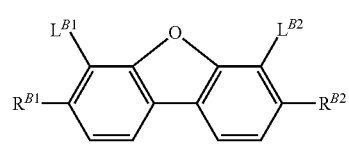

B in which $R^{B1}$ and $R^{B2}$ each, independently of one another, denote an unsubstituted alkyl radical, alkoxy radical, oxaalkyl radical or alkoxyalkyl radical having 1 to 7 C atoms, or an alkenyl radical or alkenyloxy radical having 2 to 7 C atoms, and $L^{B1}$ and $L^{B2}$ each, independently of one another, denote F or Cl.

14. A process for the stabilization of a liquid-crystalline medium which comprises adding to said liquid-crystalline medium one or more compounds of claim 7, and optionally one or more compounds of the formulae OH-1 to OH-6,

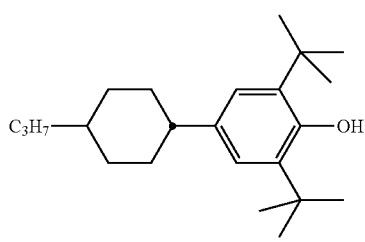
OH-1

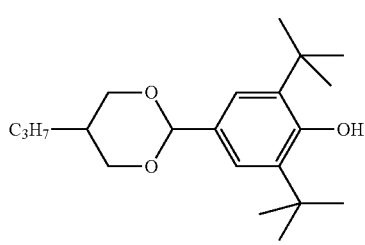
OH-2

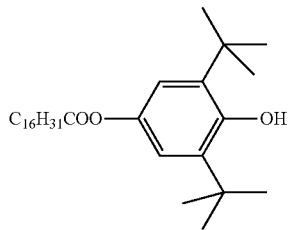
OH-3

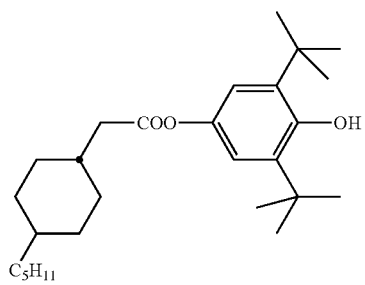
OH-4

-continued

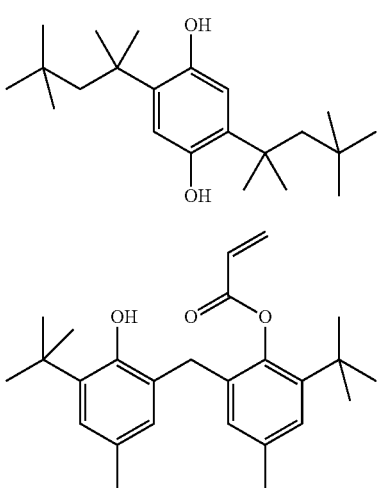

OH-5

OH-6

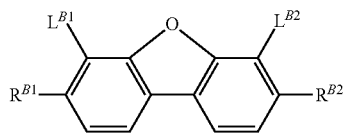

15. A process for the preparation of a compound according to claim 7, which comprises hydrogenating the corresponding 2,2,6,6-tetramethylpiperidine 1-oxyl or 1-benzyl precursor.

16. A process for the preparation of a liquid-crystalline medium according to claim 3, comprising mixing one or more compounds of the formulae I-9, I-10 or I-11 with one or more compounds of the formula B

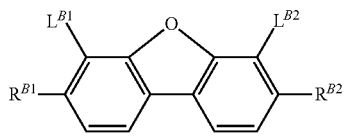
B in which
$R^{B1}$ and $R^{B2}$ each, independently of one another, denote an unsubstituted alkyl radical, alkoxy radical, oxaalkyl radical or alkoxyalkyl radical having 1 to 7 C atoms, or an alkenyl radical or alkenyloxy radical having 2 to 7 C atoms, and $L^{B1}$ and $L^{B2}$ each, independently of one another, denote F or Cl and one or more compounds of the formula II.

17. A process for the preparation of a liquid-crystalline medium according to claim 5, comprising mixing one or more compounds of the Formulae I-9, I-10 or I-11 with one or more compounds of the formula B

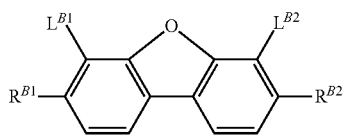
B in which
$R^{B1}$ and $R^{B2}$ each, independently of one another, denote an unsubstituted alkyl radical, alkoxy radical, oxaalkyl radical or alkoxyalkyl radical having 1 to 7 C atoms, or an alkenyl radical or alkenyloxy radical having 2 to 7 C atoms, and $L^{B1}$ and $L^{B2}$ each, independently of one another, denote F or Cl and one or more compounds of the formula III-4.

18. A medium according to claim 3, which further comprises a compound of the formula II and one or more compounds of formula B, in which

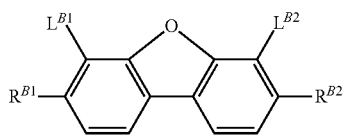
B $R^{B1}$ and $R^{B2}$ each, independently of one another, denote an unsubstituted alkyl radical, alkoxy radical, oxaalkyl radical or alkoxyalkyl radical having 1 to 7 C atoms, or an alkenyl radical or alkenyloxy radical having 2 to 7 C atoms, and $L^{B1}$ and $L^{B2}$ each, independently of one another, denote F or Cl.

* * * * *